(12) United States Patent
Marik et al.

(10) Patent No.: US 9,139,566 B2
(45) Date of Patent: *Sep. 22, 2015

(54) FLUORINE-18 AND CARBON-11 LABELED RADIOLIGANDS FOR POSITRON EMISSION TOMOGRAPHY (PET) IMAGING FOR LRRK2

(71) Applicant: Genentech, Inc., South San Francisco, CA (US)

(72) Inventors: Jan Marik, Hillsborough, CA (US); Zachary Kevin Sweeney, Redwood City, CA (US); Bryan K. Chan, San Carlos, CA (US); Anthony Estrada, San Carlos, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/687,441

(22) Filed: Nov. 28, 2012

(65) Prior Publication Data

US 2013/0156700 A1    Jun. 20, 2013

Related U.S. Application Data

(60) Provisional application No. 61/565,324, filed on Nov. 30, 2011, provisional application No. 61/720,870, filed on Oct. 31, 2012.

(51) Int. Cl.
| | |
|---|---|
| *A61K 51/00* | (2006.01) |
| *A61M 36/14* | (2006.01) |
| *C07D 403/12* | (2006.01) |
| *A61K 51/04* | (2006.01) |
| *C07D 239/48* | (2006.01) |

(52) U.S. Cl.
CPC .......... *C07D 403/12* (2013.01); *A61K 51/0453* (2013.01); *A61K 51/0455* (2013.01); *A61K 51/0459* (2013.01); *C07D 239/48* (2013.01)

(58) Field of Classification Search
CPC .................... C07D 403/12; C07D 239/48
See application file for complete search history.

(56) References Cited

U.S. PATENT DOCUMENTS

| | | | |
|---|---|---|---|
| 8,354,420 | B2 | 1/2013 | Baker-Glenn et al. |
| 2012/0157427 | A1 | 6/2012 | Baker-Glenn et al. |

FOREIGN PATENT DOCUMENTS

| | | | |
|---|---|---|---|
| WO | WO 2009127642 A2 | * | 10/2009 |
| WO | WO 2011038572 A1 | * | 4/2011 |

OTHER PUBLICATIONS

Zhang et al. Curr. Top. Med. Chem. 2007,7,1817-1828.*
Hernandez et al. Ann Neurol 2005;57:453-456.*
Marek et al. Ann. Neurol. 2008; 64; S111-S121.*

* cited by examiner

*Primary Examiner* — Michael G Hartley
*Assistant Examiner* — Sean R Donohue
(74) *Attorney, Agent, or Firm* — Robert C. Hall

(57) ABSTRACT

A method for positron emission tomography (PET) imaging of LRRK2 in tissue of a subject, the method comprising: administering a compound of formula I, formula II or formula III, or a pharmaceutically acceptable salt thereof to the subject, wherein the compound includes at least one $C^{11}$ or $F^{18}$ label thereon; allowing the compound to penetrate into the tissue of the subject; and collecting a PET image of the CNS or brain tissue of the subject.

12 Claims, 4 Drawing Sheets

FIG. 1 PET imaging in CNS – POC in Pgp/bcrp KO mice
- Increasing dose of G1023 (ip) administered 30 min before imaging resulted in dose dependent uptake blocking of imaging tracer ¹⁸FE-G1023 in brain.
- The image derived dose for 50% target engagement is 1.8 mg/kg in Pgp/bcrp KO mice.
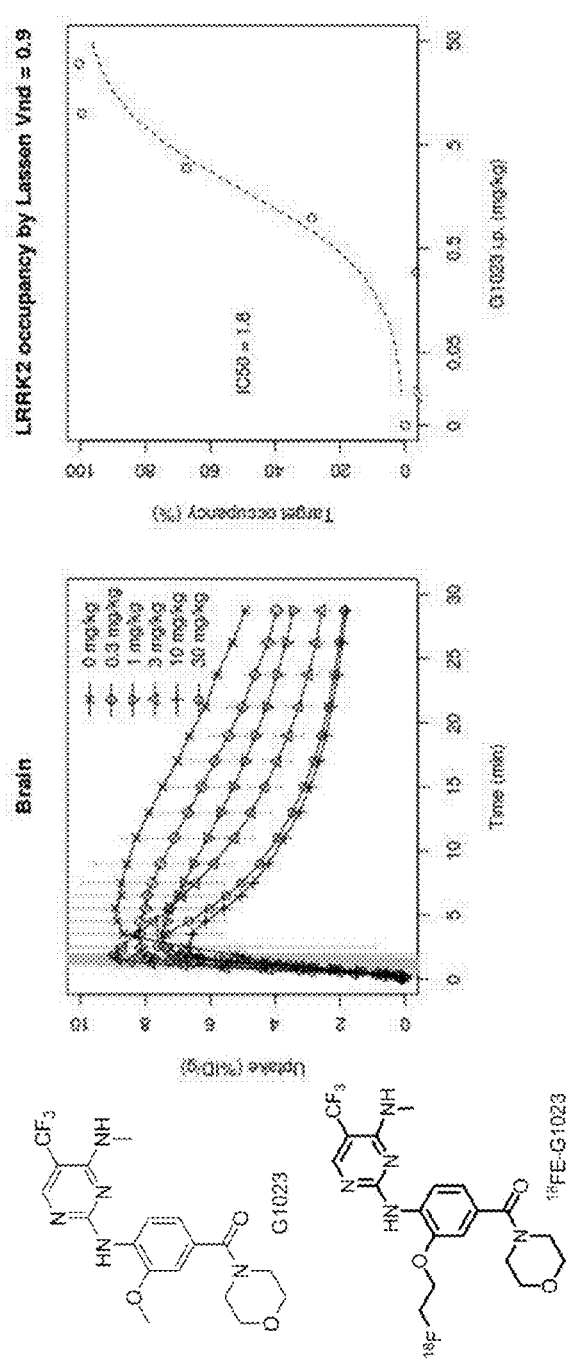
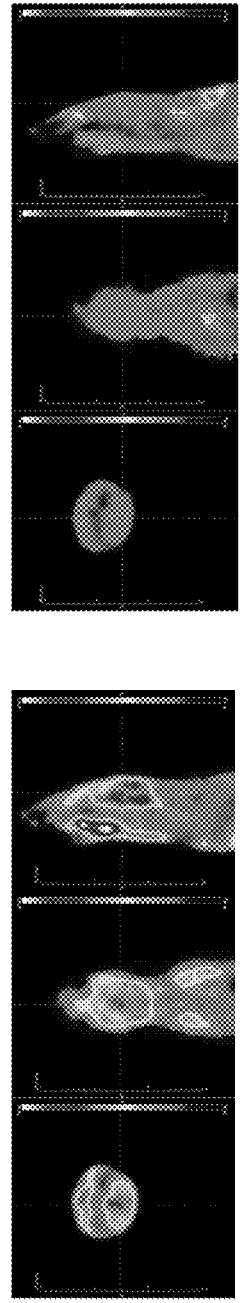

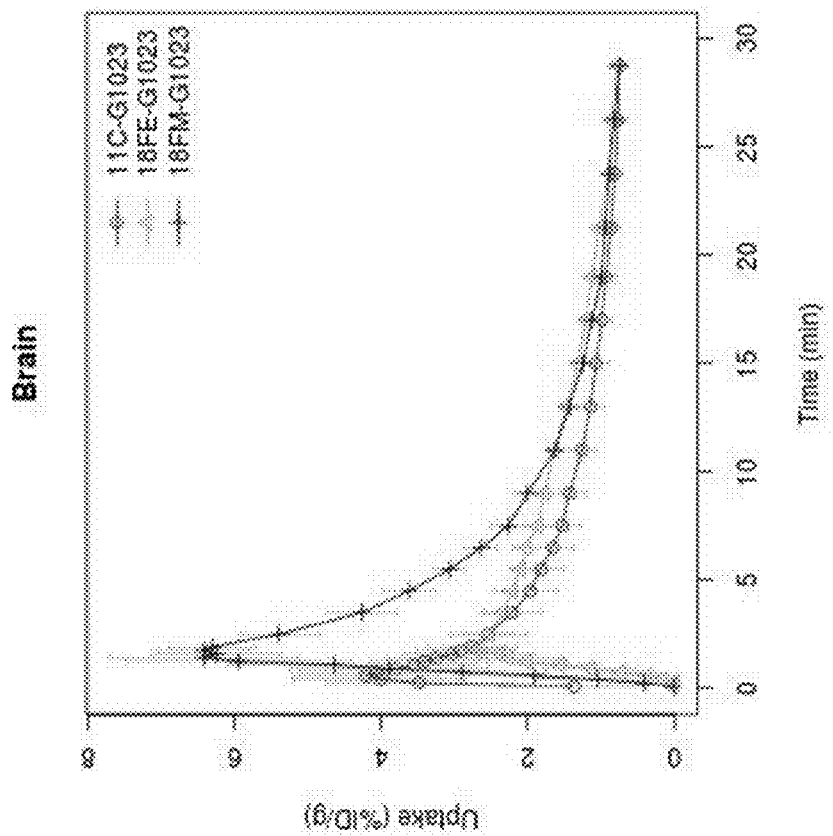
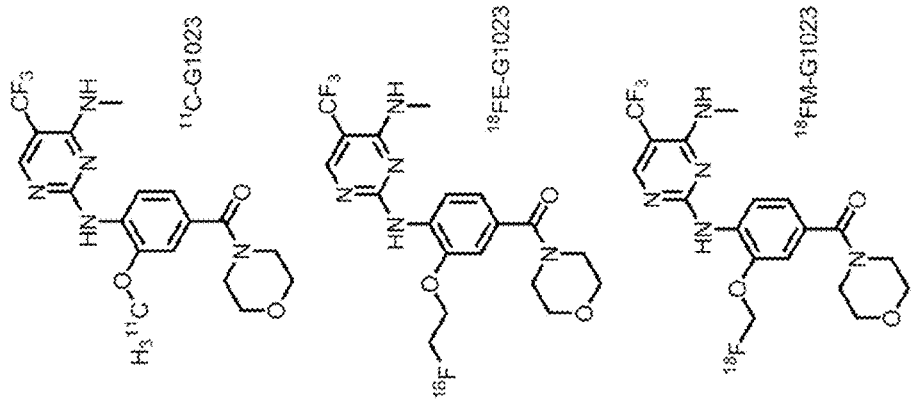
FIG. 2A CNS uptake in mice of ¹¹C-methoxy, ¹⁸F-ethoxy and ¹⁸F-methoxy analogs of G1023

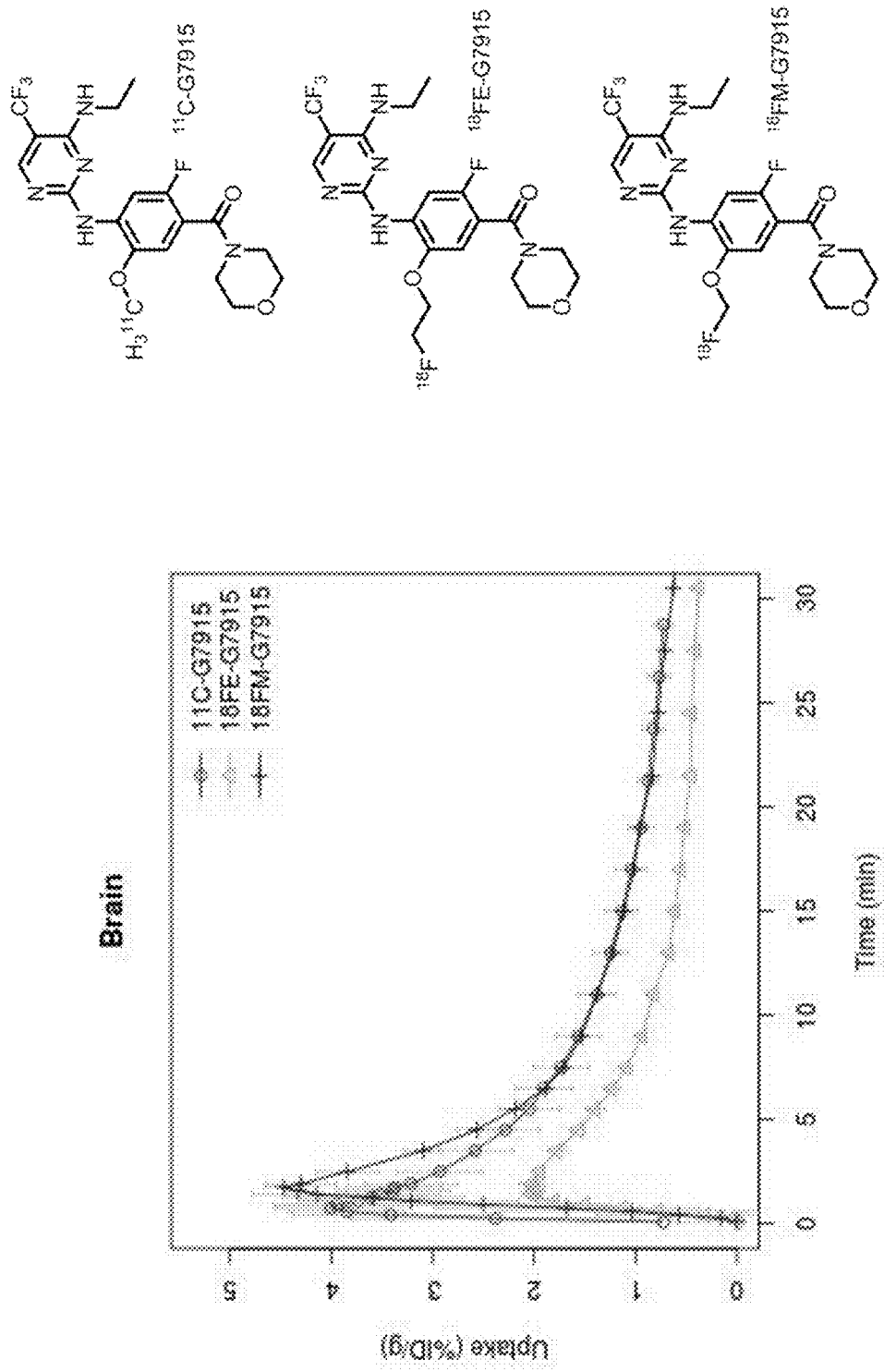
FIG. 2B CNS uptake in mice of ¹¹C-methoxy, ¹⁸F-ethoxy and ¹⁸F-methoxy analogs of G7915

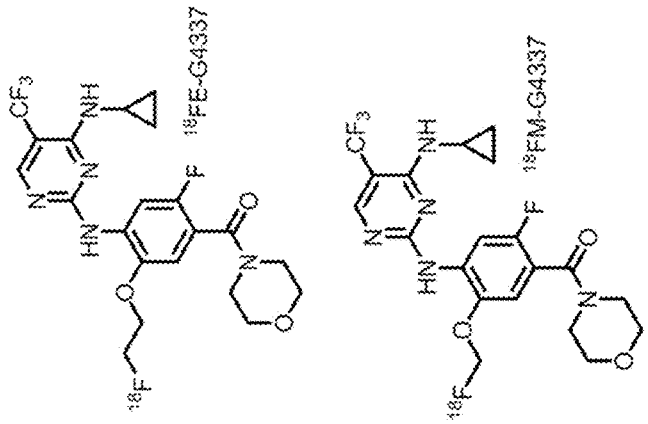
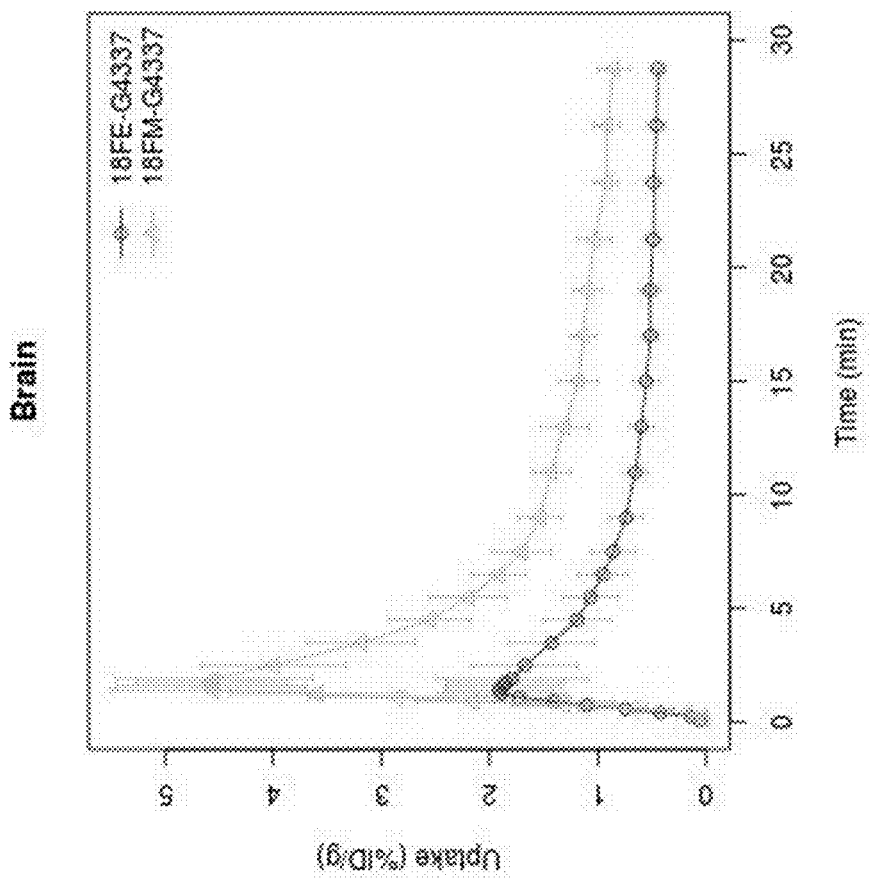
FIG. 2C CNS uptake in mice of $^{18}$F-ethoxy and $^{18}$F-methoxy analogs of G4337

FLUORINE-18 AND CARBON-11 LABELED RADIOLIGANDS FOR POSITRON EMISSION TOMOGRAPHY (PET) IMAGING FOR LRRK2

CROSS REFERENCE TO RELATED APPLICATION

This application claims the benefit under 35 USC §119 of U.S. Provisional Application Ser. No. 61/565,324 filed on Nov. 30, 2011, and U.S. Provisional Application Ser. No. 61/720,870 filed on Oct. 31, 2012, the disclosures of which is incorporated herein by reference.

FIELD OF THE INVENTION

This invention pertains to compounds having affinity for LRRK2 and are useful as PET (Positron Emission Tomography) ligands for study and treatment of LRRK2-mediated diseases and conditions such as Parkinson's disease.

BACKGROUND OF THE INVENTION

Neurodegenerative diseases such as Parkinson's disease, Lewy body dementia and Huntington's disease affect millions of individuals. Parkinson's disease is a chronic, progressive motor system disorder that afflicts approximately one out of every 1000 people, with hereditary Parkinson's disease accounting for 5-10% of all of patients. Parkinson's disease is caused by progressive loss of mid-brain dopamine neurons, leaving patients with impaired ability to direct and control their movements. The primary Parkinson's disease symptoms are trembling, rigidity, slowness of movement, and impaired balance. Many Parkinson's disease patients also experience other symptoms such as emotional changes, memory loss, speech problems, and sleeping disorders.

The gene encoding the leucine-rich repeat kinase 2 protein (LRRK2) has been identified in association with hereditary Parkinson's disease (Paisan-Ruiz et al., *Neuron*, Vol. 44(4), 2004, pp 595-600; Zimprich et al., *Neuron*, Vol. 44(4), 2004, 601-607). In-vitro studies show that Parkinson's disease-associated mutation leads to increased LRRK2 kinase activity and decreased rate of GTP hydrolysis compared to wild-type (Guo et al., *Experimental Cell Research, Vol.* 313(16), 2007, pp. 3658-3670. Anti-LRRK2 antibodies have been used to label brainstem Lewy bodies associated with Parkinson's disease and cortical antibodies associated with Lewis body dementia suggesting that LRRK2 may play an important role in Lewie body formation and pathogenesis associated with these diseases (Zhou et al., *Molecular Degeneration,* 2006, 1:17 doi:10.1186/1750-1326-1-17). LRRK2 has also been identified as a gene potentially associated with increased susceptibility to Crohn's disease and susceptibility to leprosy (Zhang et al., *New England J. Med. Vol.* 361 (2009) pp. 2609-2618.

LRRK2 has also been associated with the transition of mild cognitive impairment to Alzheimer's disease (WO2007/149789); L-Dopa induced dyskinesia (Hurley et al., *Eur. J. Neurosci.*, Vol. 26, 2007, pp. 171-177; CNS disorders associated with neuronal progenitor differentiation (Milosevic et al., *Neurodegen.*, Vol. 4, 2009, p. 25); cancers such as kidney, breast, prostate, blood and lung cancers and acute myelogenous leukemia (WO2011/038572); papillary renal and thyroid carcinomas (Looyenga et al., www.pnas.org/cgi/doi/10.1073/pnas.1012500108); multiple myeloma (Chapman et al., *Nature Vol.* 471, 2011, pp. 467-472); amyotrophic lateral sclerosis (Shtilbans et al., *Amyotrophic Lateral Sclerosis* "Early Online 2011, pp. 1-7); rheumatoid arthritis (Nakamura et al., *DNA Res.* Vol. 13(4), 2006, pp. 169-183); and ankylosing spondylytis (Danoy et al., *PLoS Genetics*, Vol. 6(12), 2010, e1001195, pp. 1-5).

Accordingly, compounds and compositions effective at modulating LRRK2 activity and usable as PET ligands may help in developing and providing treatment for neurodegenerative diseases such as Parkinson's disease and Lewie body dementia, for CNS disorders such as Alzheimer's disease and L-Dopa induced dyskinesia, for cancers such as kidney, breast, prostate, blood, papillary and lung cancers, acute myelogenous leukemia and multiple myeloma, and for inflammatory diseases such as leprosy, Crohn's disease, amyotrophic lateral sclerosis, rheumatoid arthritis, and ankylosing spondylytis.

SUMMARY OF THE INVENTION

The invention provides a method for positron emission tomography (PET) imaging of LRRK2 in central nervous system (CNS) or bain tissue of a subject, the method comprising:

administering a compound of formula I, formula II or formula III, or a pharmaceutically acceptable salt thereof to the subject, wherein the compound includes at least one $C^{11}$ or $F^{18}$ label thereon;

allowing the compound to penetrate into the CNS or brain tissue of the subject; and collecting aPET image of the CNS or brain tissue of the subject.

The invention also provides and pharmaceutical compositions comprising the compounds, methods of using the compounds, and methods of preparing the compounds.

DESCRIPTION OF THE DRAWINGS

FIG. 1: PET imaging in CNS-POC in Pgp/bcrp KO mice with $F^{18}$-labeled (3-(2-fluoroethoxy)-4-(4-(methylamino)-5-(trifluoromethyl)pyrimidin-2-ylamino)phenyl)(morpholino) methanone ((3-(2-$^{18}$F-ethoxy)-4-((4-(methylamino)-5-(trifluoromethyl)pyrimidin-2-yl)amino)phenyl)(morpholino) methanone).

FIG. 2A is a graphical representation of brain uptake in mice (% injected dose per gram of tissue vs time) for three radiolabeled analogs of the compound G1023 ((3-methoxy-4-((4-(methylamino)-5-(trifluoromethyl)pyrimidin-2-yl) amino)phenyl)(morpholino) methanone).

FIG. 2B is a graphical representation of brain uptake in mice (% injected dose per gram of tissue vs time) for three radiolabeled analogs of the compound G7915 ((4-((4-(ethylamino)-5-(trifluoromethyl)pyrimidin-2-yl)amino)-2-fluoro-5-methoxyphenyl)(morpholino)methanone).

FIG. 2C is a graphical representation of brain uptake in mice (% injected dose per gram of tissue vs time) for two radiolabeled analogs of the compound G4337 ((4-((4-(cyclopropylamino)-5-(trifluoromethyl)pyrimidin-2-yl)amino)-2-fluoro-5-methoxyphenyl)(morpholino)methanone).

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl means a moiety of the formula —R'—$SO_2$—R" where where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively.

"Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, —CH$_2$CH$_2$F, —CD$_2$CD$_2$F, —CH$_2$CD$_2$F, —CH$_2$F, —CD$_2$F, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Parkinson's disease" means a degenerative disorder of the central nervous system that impairs motor skills, speech, and/or cognitive function. Symptoms of Parkinson's disease may include, for example, muscle rigidity, tremor, slowing of physical movement (bradykinesia) and loss of physical movement (akinesia).

"Lewie body disease" also called "Lewie body dementia", diffuse Lewy body disease", cortical Lewie body disease", means a neurogenerative disorder characterized anatomically by the presence of Lewie bodies in the brain.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this Application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium (D) and tritium (T), and the carbon atoms are meant to include $C^{13}$ and $C^{14}$ isotopes.

PET Ligand Compounds for LRRK2

The invention provides a method for positron emission tomography (PET) imaging of LRRK2 in tissue of a subject, the method comprising:

administering a compound of formula I, formula II or formula III, or a pharmaceutically acceptable salt thereof to the subject, wherein the compound includes at least one $C^{11}$ or $F^{18}$ label thereon;

allowing the compound to penetrate into the CNS or brain tissue of the subject; and collecting a PET image of the CNS or brain tissue of the subject.

In certain embodiments, the compound is of formula I.
In certain embodiments, the compound is of formula II.
In certain embodiments, the compound is of formula III.
In certain embodiments, the PET imaging is carried out in central nervous system (CNS) or brain tissue of a subject.
In certain embodiments, the PET imaging is carried out in central nervous system (CNS) tissue of a subject.
In certain embodiments, the PET imaging is carried out in brain tissue of a subject.

The method may further comprise introducing at least one $C^{11}$ or $F^{18}$ label onto the compound of formula I, formula II or formula III.

In one embodiment, the compounds used in the subject method are labeled with $F^{18}$.
In one embodiment, the compounds used in the subject method are labeled with $C^{11}$.
In one embodiment, the compounds used in the subject method are labeled with $F^{18}$ or $^{11}C$ on a $C_{1-6}$alkoxy moiety.
In one embodiment, the compounds used in the subject method are labeled with $F^{18}$ on a $C_{1-6}$alkoxy moiety.
In one embodiment, the compounds used in the subject method are labeled with $C^{11}$ on a $C_{1-6}$alkoxy moiety.
In one embodiment, the compounds used in the subject method are labeled with $F^{18}$ on a methoxy or ethoxy moiety.
In one embodiment, the compounds used in the subject method are labeled with $F^{18}$ on a methoxy or ethoxy moiety which may additionally include deuterium replacements to hydrogen.
In one embodiment, the compounds used in the subject method are labeled with $F^{18}$ on a methoxy moiety.
In one embodiment, the compounds used in the subject method are labeled with $F^{18}$ on an ethoxy moiety.
In one embodiment, the compounds used in the subject method are labeled with $C^{11}$ on a methoxy moiety.

The invention also provides a compound of formula I, II or III, or a pharmaceutical salt thereof, wherein the compound includes at least one $C^{11}$ or $F^{18}$ label thereon.

In certain embodiments, the invention provides a compound of formula I, or a pharmaceutical salt thereof, wherein the compound includes at least one $C^{11}$ or $F^{18}$ label thereon.

In certain embodiments, the invention provides a compound of formula II, or a pharmaceutical salt thereof, wherein the compound includes at least one $C^{11}$ or $F^{18}$ label thereon.

In certain embodiments, the invention provides a compound of formula III, or a pharmaceutical salt thereof, wherein the compound includes at least one $C^{11}$ or $F^{18}$ label thereon.

In certain embodiments, the invention provides a compound of formula I, II or III, or a pharmaceutical salt thereof, wherein the compound includes $-O^{11}CH_3$, $-CH_2CH_2{}^{18}F$, $-CD_2CD_2{}^{18}F$, $-CH_2CD_2{}^{18}F$, $-CH_2{}^{18}F$, or $-CD_2{}^{18}F$ thereon.

In certain embodiments, the invention provides a compound of formula I, II or III, or a pharmaceutical salt thereof, wherein the compound includes a $-O^{11}CH_3$ group thereon.

In certain embodiments, the invention provides a compound of formula I, II or III, or a pharmaceutical salt thereof, wherein the compound includes a $-CH_2CH_2{}^{18}F$ group thereon.

In certain embodiments, the invention provides a compound of formula I, II or III, or a pharmaceutical salt thereof, wherein the compound includes a $-CD_2CD_2{}^{18}F$ group thereon.

In certain embodiments, the invention provides a compound of formula I, II or III, or a pharmaceutical salt thereof, wherein the compound includes a $-CH_2CD_2{}^{18}F$ group thereon.

In certain embodiments, the invention provides a compound of formula I, II or III, or a pharmaceutical salt thereof, wherein the compound includes a $-CH_2{}^{18}F$ group thereon.

In certain embodiments, the invention provides a compound of formula I, II or III, or a pharmaceutical salt thereof, wherein the compound includes a $-CD_2{}^{18}F$ group thereon.

In one embodiment the PET ligand compound includes a $C_{1-6}$alkoxy moiety capable of being labeled with $C^{11}$, or a fluoro-$C_{1-6}$alkoxy moiety capable of being labeled with $F^{18}$.

In one embodiment, the LRRK2 PET ligand compound is of formula I:

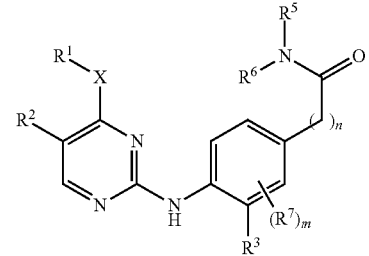

I or pharmaceutically acceptable salts thereof,
wherein:
m is from 0 to 3;
X is: $-NR^a-$; $-O-$; or $-S(O)_r-$ wherein r is from 0 to 2 and $R^a$ is hydrogen or $C_{1-6}$alkyl;
$R^1$ is: $C_{1-6}$alkyl; halo-$C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl or halo; $C_{3-6}$cycloalkyl-$C_{1-6}$alkyl wherein the $C_{3-6}$cycloalkyl portion is optionally substituted with $C_{1-6}$alkyl; tetrahydropyranyl; tetrahydrofuranyl; tetrahydrofuranyl-$C_{1-6}$alkyl; oxetanyl; or oxetan-$C_{1-6}$alkyl;

or $R^1$ and $R^a$ together with the atoms to which they are attached may form a three to six membered ring that may optionally include an additional heteroatom selected from O, N and S, and which is substituted with oxo, halo or $C_{1-6}$alkyl;

$R^2$ is: halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; acetyl; oxetanyl; or oxetan-$C_{1-6}$alkyl;

R$^3$ is: —OR$^4$; halo; cyano; C$_{1-6}$alkyl; halo-C$_{1-6}$alkyl; C$_{3-6}$cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl;

R$^4$ is: hydrogen; C$_{1-6}$alkyl; halo-C$_{1-6}$alkyl; C$_{1-6}$alkoxy-C$_{1-6}$alkyl; C$_{3-6}$cycloalkyl optionally substituted with C$_{1-6}$alkyl or halo; C$_{3-6}$cycloalkyl-C$_{1-6}$alkyl wherein the C$_{3-6}$cycloalkyl portion is optionally substituted with C$_{1-6}$alkyl or halo; tetrahydrofuranyl; tetrahydrofuranyl-C$_{1-6}$alkyl; oxetanyl; or oxetan-C$_{1-6}$alkyl;

n is 0 or 1;

R$^5$ is: hydrogen; or C$_{1-6}$alkyl.

R$^6$ is: hydrogen; C$_{1-6}$alkyl; C$_{1-6}$alkoxy-C$_{1-6}$alkyl; hydroxy-C$_{1-6}$alkyl; amino-C$_{1-6}$alkyl; C$_{3-6}$cycloalkyl; C$_{3-6}$cycloalkyl-C$_{1-6}$alkyl; heterocyclyl; or heterocyclyl-C$_{1-6}$alkyl; wherein the C$_{3-6}$cycloalkyl, C$_{3-6}$cycloalkyl-C$_{1-6}$alkyl, heterocyclyl and heterocyclyl-C$_{1-6}$alkyl each may be optionally substituted with one, two, three or four groups selected from: C$_{1-6}$alkyl; halo-C$_{1-6}$alkyl; C$_{1-6}$alkoxy; halo-C$_{1-6}$alkoxy; hydroxy; hydroxy-C$_{1-6}$alkyl; halo; nitrile; C$_{1-6}$alkyl-carbonyl; C$_{1-6}$alkyl-sulfonyl; C$_{3-6}$cycloalkyl; C$_{3-6}$cycloalkyl-C$_{1-6}$alkyl; C$_{3-6}$cycloalkyl-carbonyl; amino; or heterocyclyl; or two of the groups together with the atoms to which they are attached may form a five or six-membered ring;

or R$^5$ and R$^6$ together with the nitrogen atom to which they are attached form a three- to seven-membered ring that optionally includes an additional heteroatom selected from O, N and S(O)$_n$, and which is optionally substituted with one, two, three or four groups independently selected from: C$_{1-6}$alkyl; halo-C$_{1-6}$alkyl; C$_{1-6}$alkoxy; halo-C$_{1-6}$alkoxy; hydroxy; C$_{1-6}$alkoxy-C$_{1-6}$alkyl; hydroxy-C$_{1-6}$alkyl; halo, nitrile; C$_{1-6}$alkyl-carbonyl; C$_{1-6}$alkyl-sulfonyl; C$_{3-6}$cycloalkyl; C$_{3-6}$cycloalkyl-C$_{1-6}$alkyl; C$_{3-6}$cycloalkyl-carbonyl; amino; or heterocyclyl; or two of the groups together with the atoms to which they are attached may form a five or six-membered ring; and R$^7$ is: halo; C$_{1-6}$alkyl; C$_{1-6}$alkoxy; halo-C$_{1-6}$alkyl; or halo-C$_{1-6}$alkoxy.

In certain embodiments of formula I, n is 0.

In certain embodiments of formula I, n is 1.

In certain embodiments of formula I, m is from 0 to 2.

In certain embodiments of formula I, m is 0 or 1.

In certain embodiments of formula I, m is 0.

In certain embodiments of formula I, m is 1.

In certain embodiments of formula I, r is 0.

In certain embodiments of formula I, r is 2.

In certain embodiments of formula I, X is —NR$^a$— or —O—.

In certain embodiments of formula I, X is —NR$^a$.

In certain embodiments of formula I, X is —O—.

In certain embodiments of formula I, X is —S(O)$_n$—.

In certain embodiments of formula I, X is —NH— or —O—.

In certain embodiments of formula I, R$^a$ is hydrogen.

In certain embodiments of formula I, R$^a$ is C$_{1-6}$alkyl.

In certain embodiments of formula I, R$^1$ is: C$_{1-6}$alkyl; halo-C$_{1-6}$alkyl; C$_{1-6}$alkoxy-C$_{1-6}$alkyl; amino-C$_{1-6}$alkyl; C$_{1-6}$alkylsulfonyl-C$_{1-6}$alkyl; C$_{3-6}$cycloalkyl; or C$_{3-6}$cycloalkyl-C$_{1-6}$alkyl.

In certain embodiments of formula I, R$^1$ is: C$_{1-6}$alkyl; C$_{3-6}$cycloalkyl optionally substituted with C$_{1-6}$alkyl; or C$_{3-6}$cycloalkyl-C$_{1-6}$alkyl wherein the C$_{3-6}$cycloalkyl portion is optionally substituted with C$_{1-6}$alkyl.

In certain embodiments of formula I, R$^1$ is: C$_{1-6}$alkyl; halo-C$_{1-6}$alkyl; C$_{1-6}$alkoxy-C$_{1-6}$alkyl; amino-C$_{1-6}$alkyl; C$_{1-6}$alkylsulfonyl-C$_{1-6}$alkyl; tetrahydrofuranyl; tetrahydrofuranyl-C$_{1-6}$alkyl; oxetanyl; or oxetan-C$_{1-6}$alkyl.

In certain embodiments of formula I, R$^1$ is: C$_{1-6}$alkyl; halo-C$_{1-6}$alkyl; C$_{1-6}$alkoxy-C$_{1-6}$alkyl; amino-C$_{1-6}$alkyl; or C$_{1-6}$alkylsulfonyl-C$_{1-6}$alkyl.

In certain embodiments of formula I, R$^1$ is C$_{1-6}$alkyl.

In certain embodiments of formula I, R$^1$ is halo-C$_{1-6}$alkyl.

In certain embodiments of formula I, R$^1$ is C$_{1-6}$alkoxy-C$_{1-6}$alkyl.

In certain embodiments of formula I, R$^1$ is amino-C$_{1-6}$alkyl.

In certain embodiments of formula I, R$^1$ is C$_{1-6}$alkylsulfonyl-C$_{1-6}$alkyl optionally substituted with C$_{1-6}$alkyl.

In certain embodiments of formula I, R$^1$ is C$_{3-6}$cycloalkyl optionally substituted with C$_{1-6}$alkyl.

In certain embodiments of formula I, R$^1$ is C$_{3-6}$cycloalkyl-C$_{1-6}$alkyl wherein the C$_{3-6}$cycloalkyl portion is optionally substituted with C$_{1-6}$alkyl.

In certain embodiments of formula I, R$^1$ is tetrahydropyranyl.

In certain embodiments of formula I, R$^1$ is tetrahydrofuranyl.

In certain embodiments of formula I, R$^1$ is tetrahydrofuranyl-C$_{1-6}$alkyl; oxetanyl.

In certain embodiments of formula I, R$^1$ is or oxetan-C$_{1-6}$alkyl.

In certain embodiments of formula I, R$^1$ is: methyl; ethyl; n-propyl; isopropyl; isobutyl; 3,3-dimethylpropyl; cyclopropyl; cyclobutyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl.

In certain embodiments of formula I, R$^1$ is: methyl; ethyl; n-propyl; isopropyl; isobutyl; 3,3-dimethylpropyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl.

In certain embodiments of formula I, R$^1$ is: methyl; ethyl; n-propyl; isopropyl; isobutyl; 3,3-dimethylpropyl; cyclopentyl; cyclohexyl; cyclopentylmethyl; methoxyethyl; oxetanyl; or tetrahydrofuranylmethyl.

In certain embodiments of formula I, R$^1$ is: methyl; ethyl; n-propyl; isopropyl; or isobutyl.

In certain embodiments of formula I, R$^1$ is methyl or ethyl.

In certain embodiments of formula I, R$^1$ is methyl.

In certain embodiments of formula I, R$^1$ is ethyl.

In certain embodiments of formula I, R$^1$ is: cyclopropyl; cyclobutyl; cyclopentyl; cyclohexyl; cyclopropylmethyl; cyclobutylmethyl; cyclopentylmethyl; or cyclopropylethyl.

In certain embodiments of formula I, R$^1$ is: cyclopropyl.

In certain embodiments of formula I, R$^1$ is: cyclopentyl; cyclohexyl; or cyclopentylmethyl.

In certain embodiments of formula I, R$^2$ is: halo; C$_{1-6}$alkoxy; halo-C$_{1-6}$alkyl; halo-C$_{1-6}$alkoxy; C$_{3-6}$cycloalkyl wherein the C$_{3-6}$cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl.

In certain embodiments of formula I, R$^2$ is: halo; C$_{1-6}$alkoxy; halo-C$_{1-6}$alkyl; cyano; C$_{2-6}$alkynyl; C$_{2-6}$alkenyl; C$_{3-6}$cycloalkyl; or C$_{3-6}$cycloalkyl-C$_{1-6}$alkyl.

In certain embodiments of formula I, R$^2$ is: halo; C$_{1-6}$alkoxy; halo-C$_{1-6}$alkyl; cyano; C$_{3-6}$cycloalkyl; or C$_{3-6}$cycloalkyl-C$_{1-6}$alkyl.

In certain embodiments of formula I, R$^2$ is: halo; C$_{1-6}$alkoxy; halo-C$_{1-6}$alkyl; C$_{3-6}$cycloalkyl; or C$_{3-6}$cycloalkyl-C$_{1-6}$alkyl.

In certain embodiments of formula I, $R^2$ is: halo; halo-$C_{1-6}$alkyl; or cyano.

In certain embodiments of formula I, $R^2$ is: halo; or halo-$C_{1-6}$alkyl.

In certain embodiments of formula I, $R^2$ is halo.

In certain embodiments of formula I, $R^2$ is $C_{1-6}$alkoxy.

In certain embodiments of formula I, $R^2$ is halo-$C_{1-6}$alkoxy.

In certain embodiments of formula I, $R^2$ is halo-$C_{1-6}$alkyl.

In certain embodiments of formula I, $R^2$ is $C_{3-6}$cycloalkyl.

In certain embodiments of formula I, $R^2$ is $C_{3-6}$cycloalkyl-$C_{1-6}$alkyl.

In certain embodiments of formula I, $R^2$ is tetrahydrofuranyl.

In certain embodiments of formula I, $R^2$ is tetrahydrofuranyl-$C_{1-6}$alkyl.

In certain embodiments of formula I, $R^2$ is oxetanyl.

In certain embodiments of formula I, $R^2$ is oxetan-$C_{1-6}$alkyl.

In certain embodiments of formula I, $R^2$ is halo, trifluoromethyl or cyano.

In certain embodiments of formula I, $R^2$ is chloro, trifluoromethyl or cyano.

In certain embodiments of formula I, $R^2$ is fluoro, chloro or bromo.

In certain embodiments of formula I, $R^2$ is chloro.

In certain embodiments of formula I, $R^2$ is fluoro.

In certain embodiments of formula I, $R^2$ is $F^{18}$-fluoro.

In certain embodiments of formula I, $R^2$ is bromo.

In certain embodiments of formula I, $R^2$ is trifluoromethyl.

In certain embodiments of formula I, $R^2$ is trifluoromethyl wherein one of the fluoro groups is $F^{18}$.

In certain embodiments of formula I, $R^2$ is methoxy.

In certain embodiments of formula I, $R^2$ is cyano.

In certain embodiments of formula I, $R^2$ is $C_{2-6}$alkynyl.

In certain embodiments of formula I, $R^2$ is $C_{2-6}$alkenyl.

In certain embodiments of formula I, $R^3$ is $—OR^4$.

In certain embodiments of formula I, $R^3$ is: $C_{1-6}$alkyl; or halo-$C_{1-6}$alkyl.

In certain embodiments of formula I, $R^3$ is: halo; or $—OR^4$.

In certain embodiments of formula I, $R^3$ is: halo; $C_{1-6}$alkoxy; halo-$C_{1-6}$alkoxy; $C_{3-6}$cycloalkyloxy; or $C_{3-6}$cycloalkyl-$C_{1-6}$alkyloxy.

In certain embodiments of formula I, $R^3$ is: $C_{1-6}$alkoxy; halo-$C_{1-6}$alkoxy; $C_{3-6}$cycloalkyloxy; or $C_{3-6}$cycloalkyl-$C_{1-6}$alkyloxy.

In certain embodiments of formula I, $R^3$ is: halo; $C_{1-6}$alkoxy; cyano; or halo-$C_{1-6}$alkoxy.

In certain embodiments of formula I, $R^3$ is: halo; $C_{1-6}$alkoxy; or halo-$C_{1-6}$alkoxy.

In certain embodiments of formula I, $R^3$ is: methoxy; halo; trifluoromethoxy; difluoromethoxy; 2-halo-ethoxy or 2,2,2-trihaloethoxy.

In certain embodiments of formula I, $R^3$ is: methoxy; or halo.

In certain embodiments of formula I, $R^3$ is: methoxy; chloro; or fluoro.

In certain embodiments of formula I, $R^3$ is methoxy.

In certain embodiments of formula I, $R^3$ is chloro.

In certain embodiments of formula I, $R^3$ is fluoro.

In certain embodiments of formula I, $R^3$ is: $C_{1-6}$alkoxy; cyano; or halo-$C_{1-6}$alkoxy.

In certain embodiments of formula I, $R^3$ is: $C_{1-6}$alkoxy; or halo-$C_{1-6}$alkoxy.

In certain embodiments of formula I, $R^3$ is $C_{1-6}$alkoxy.

In certain embodiments of formula I, $R^3$ is $C_{1-6}$alkoxy with a $F^{18}$ or $^{11}C$ atom thereon.

In certain embodiments of formula I, $R^3$ is $C_{1-6}$alkoxy wherein at least one carbon is $C^{11}$.

In certain embodiments of formula I, $R^3$ is $C_{1-6}$alkyl wherein at least one carbon is $C^{11}$.

In certain embodiments of formula I, $R^3$ is $C^{11}$methoxy.

In certain embodiments of formula I, $R^3$ is $C^{11}$methyl.

In certain embodiments of formula I, $R^3$ is halo-$C_{1-6}$alkyl wherein at least one halo is $F^{18}$.

In certain embodiments of formula I, $R^3$ is halo-$C_{1-6}$alkoxy.

In certain embodiments of formula I, $R^3$ is halo-$C_{1-6}$alkoxy wherein at least one halo is $F^{18}$.

In certain embodiments of formula I, $R^3$ is fluoromethoxy.

In certain embodiments of formula I, $R^3$ is 2-fluoroethoxy.

In certain embodiments of formula I, $R^3$ is fluoro-di-deuteromethoxy ($FCD_2O—$).

In certain embodiments of formula I, $R^3$ is 2-fluoro-tetra-deuteroethoxy ($FCD_2CD_2O—$).

In certain embodiments of formula I, $R^3$ is $F^{18}$fluoromethoxy ($F^{18}CH_2O—$).

In certain embodiments of formula I, $R^3$ is 2-$F^{18}$fluoroethoxy ($F^{18}CH_2CH_2O—$).

In certain embodiments of formula I, $R^3$ is $F^{18}$fluoro-di-deuteromethoxy ($F^{18}CD_2O—$).

In certain embodiments of formula I, $R^3$ is 2-$F^{18}$fluoro-tetra-deuteroethoxy ($F^{18}CD_2CD_2O—$).

In certain embodiments of formula I, $R^3$ is $—O^{11}CH_3$, $—CH_2CH_2^{18}F$, $—CD_2CD_2^{18}F$, $—CH_2CD_2^{18}F$, $—CH_2^{18}F$, or $—CD_2^{18}F$.

In certain embodiments of formula I, $R^3$ is $F^{18}$.

In certain embodiments of formula I, $R^3$ is cyano.

In certain embodiments of formula I, $R^3$ is $C_{3-6}$cycloalkyl.

In certain embodiments of formula I, $R^3$ is $C_{3-6}$cycloalkyl-$C_{1-6}$alkyl.

In certain embodiments of formula I, $R^3$ is tetrahydrofuranyl. In certain embodiments of formula I, $R^3$ is tetrahydrofuranyl-$C_{1-6}$alkyl.

In certain embodiments of formula I, $R^3$ is oxetanyl.

In certain embodiments of formula I, $R^3$ is oxetan-$C_{1-6}$alkyl.

In certain embodiments of formula I, $R^4$ is: $C_{1-6}$alkyl; halo-$C_{1-6}$alkyl; $C_{1-6}$alkoxy-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydro furanyl-$C_{1-6}$alkyl; oxetanyl; or oxetan-$C_{1-6}$alkyl;

In certain embodiments of formula I, $R^4$ is: $C_{1-6}$alkyl; halo-$C_{1-6}$alkyl; $C_{1-6}$alkoxy-$C_{1-6}$alkyl; $C_{3-6}$cycloalkyl; or $C_{3-6}$cycloalkyl-$C_{1-6}$alkyl.

In certain embodiments of formula I, $R^4$ is: $C_{1-6}$alkyl; halo-$C_{1-6}$alkyl; or $C_{3-6}$cycloalkyl.

In certain embodiments of formula I, $R^4$ is $C_{1-6}$alkyl.

In certain embodiments of formula I, $R^4$ is halo-$C_{1-6}$alkyl.

In certain embodiments of formula I, $R^4$ is $C_{1-6}$alkoxy-$C_{1-6}$alkyl.

In certain embodiments of formula I, $R^4$ is $C_{3-6}$cycloalkyl.

In certain embodiments of formula I, $R^4$ is $C_{3-6}$cycloalkyl-$C_{1-6}$alkyl.

In certain embodiments of formula I, $R^4$ is tetrahydrofuranyl.

In certain embodiments of formula I, $R^4$ is tetrahydrofuranyl-$C_{1-6}$alkyl.

In certain embodiments of formula I, $R^4$ is oxetanyl.

In certain embodiments of formula I, $R^4$ is or oxetan-$C_{1-6}$alkyl.

In certain embodiments of formula I, $R^4$ is: methyl; ethyl; isopropyl; cyclopropyl; cyclobutyl; cyclopropylmethyl; cyclobutylmethyl; 2-haloethyl; or 2,2,2-trihaloethyl.

In certain embodiments of formula I, $R^4$ is methyl.
In certain embodiments of formula I, $R^5$ is hydrogen.
In certain embodiments of formula I, $R^5$ is $C_{1-6}$alkyl.
In certain embodiments of formula I, $R^5$ is methyl.
In certain embodiments of formula I, $R^5$ is ethyl.
In certain embodiments of formula I, $R^6$ is hydrogen.
In certain embodiments of formula I, $R^6$ is $C_{1-6}$alkyl.
In certain embodiments of formula I, $R^6$ is $C_{1-6}$alkoxy-$C_{1-6}$alkyl.
In certain embodiments of formula I, $R^6$ is hydroxy-$C_{1-6}$alkyl.
In certain embodiments of formula I, $R^6$ is amino-$C_{1-6}$alkyl.

In certain embodiments of formula I, $R^6$ is $C_{3-6}$cycloalkyl optionally substituted with one, two or three groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo; nitrile; $C_{1-6}$alkyl-carbonyl; $C_{1-6}$alkyl-sulfonyl; $C_{3-6}$cycloalkyl; $C_{3-6}$cycloalkyl-$C_{1-6}$alkyl; $C_{3-6}$cycloalkyl-carbonyl; amino; or heterocyclyl; or two of the groups together with the atoms to which they are attached may form a five or six-membered ring.

In certain embodiments of formula I, $R^6$ is $C_{3-6}$cycloalkyl-$C_{1-6}$alkyl wherein the $C_{3-6}$cycloalkyl portion thereof is optionally substituted with one, two or three groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo; nitrile; $C_{1-6}$alkyl-carbonyl; $C_{1-6}$alkyl-sulfonyl; $C_{3-6}$cycloalkyl; $C_{3-6}$cycloalkyl-$C_{1-6}$alkyl; $C_{3-6}$cycloalkyl-carbonyl; amino; or heterocyclyl; or two of the groups together with the atoms to which they are attached may form a five or six-membered ring.

In embodiments of formula I wherein $R^6$ is heterocyclyl, such heterocycle may be: azetidinyl; pyrrolidinyl; piperidinyl; piperazinyl; morpholinyl; thiomorpholinyl; 3-oxa-8-aza-bicyclo[3.2.1]oct-8-yl; 2-oxa-5-aza-bicyclo[2.2.1]hept-5-yl; or 8-oxa-3-aza-bicyclo[3.2.1]oct-3-yl; each optionally substituted as defined herein.

In embodiments of formula I wherein $R^6$ is heterocyclyl, such heterocycle may be: azetidinyl; pyrrolidinyl; piperidinyl; piperazinyl; or morpholinyl; each optionally substituted as defined herein, i.e., such heterocycyl is optionally substituted with one, two or three groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo; nitrile; $C_{1-6}$alkyl-carbonyl; $C_{1-6}$alkyl-sulfonyl; $C_{3-6}$cycloalkyl; $C_{3-6}$cycloalkyl-$C_{1-6}$alkyl; $C_{3-6}$cycloalkyl-carbonyl; amino; or heterocyclyl; or two of the groups together with the atoms to which they are attached may form a five or six-membered ring.

In certain embodiments of formula I, $R^6$ is heterocyclyl optionally substituted with one, two or three groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo; nitrile; $C_{1-6}$alkyl-carbonyl; $C_{1-6}$alkyl-sulfonyl; $C_{3-6}$cycloalkyl; $C_{3-6}$cycloalkyl-$C_{1-6}$alkyl; $C_{3-6}$cycloalkyl-carbonyl; amino; or heterocyclyl; or two of the groups together with the atoms to which they are attached may form a five or six-membered ring.

In embodiments of formula I wherein $R^6$ is heterocyclyl-$C_{1-6}$alkyl, the heterocyclyl portion thereof may be: azetidinyl; pyrrolidinyl; piperidinyl; piperazinyl; morpholinyl; thiomorpholinyl; 3-oxa-8-aza-bicyclo[3.2.1]oct-8-yl; 2-oxa-5-aza-bicyclo[2.2.1]hept-5-yl; or 8-oxa-3-aza-bicyclo[3.2.1]oct-3-yl; each optionally substituted as defined herein, i.e., such heterocycyl portion is optionally substituted with one, two or three groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo; nitrile; $C_{1-6}$alkyl-carbonyl; $C_{1-6}$alkyl-sulfonyl; $C_{3-6}$cycloalkyl; $C_{3-6}$cycloalkyl-$C_{1-6}$alkyl; $C_{3-6}$cycloalkyl-carbonyl; amino; or heterocyclyl; or two of the groups together with the atoms to which they are attached may form a five or six-membered ring.

In embodiments of formula I wherein $R^6$ is heterocyclyl-$C_{1-6}$alkyl, the heterocyclyl portion thereof may be: azetidinyl; pyrrolidinyl; piperidinyl; piperazinyl; or morpholinyl; each optionally substituted as defined herein.

In certain embodiments of formula I, $R^6$ is heterocyclyl-$C_{1-6}$alkyl wherein the heterocyclyl portion thereof is optionally substituted with one, two or three groups independently selected from: $C_{1-6}$alkyl; halo-$C_{1-6}$alkyl; $C_{1-6}$alkoxy; halo-$C_{1-6}$alkoxy; hydroxy; hydroxy-$C_{1-6}$alkyl; halo; nitrile; $C_{1-6}$alkyl-carbonyl; $C_{1-6}$alkyl-sulfonyl; $C_{3-6}$cycloalkyl; $C_{3-6}$cycloalkyl-$C_{1-6}$alkyl; $C_{3-6}$cycloalkyl-carbonyl; amino; or heterocyclyl; or two of the groups together with the atoms to which they are attached may form a five or six-membered ring.

In certain embodiments of formula I, $R^6$ is: hydrogen; methyl; ethyl; isopropyl; or cyclopropyl.

In certain embodiments of formula I, $R^6$ is: hydrogen; methyl; ethyl; isopropyl; 2-amino-propyl; oxetan-3-yl; 2-methoxy-ethyl; 2-hydroxy-ethyl; cyclopropyl; piperidin-4-yl; 1-methyl-piperidin-4-yl; tert-butyl; 2-hydroxy-2-methyl-propyl; cyclobutyl; 1-methyl-cyclobutyl; 2-hydroxy-propyl; 1-cyano-cyclopropyl; 3,3-difluoro-cyclobutyl; cyclopropylmethyl; 3-fluoro-cyclobutyl; or 2,2-difluoroethyl;

In certain embodiments of formula I, $R^6$ is hydrogen.
In certain embodiments of formula I, $R^6$ is methyl.
In certain embodiments of formula I, $R^6$ is ethyl.
In certain embodiments of formula I, $R^6$ is isopropyl.
In certain embodiments of formula I, $R^6$ is 2-amino-propyl.
In certain embodiments of formula I, $R^6$ is oxetan-3-yl.
In certain embodiments of formula I, $R^6$ is 2-methoxy-ethyl.
In certain embodiments of formula I, $R^6$ is 2-hydroxy-ethyl.
In certain embodiments of formula I, $R^6$ is cyclopropyl.
In certain embodiments of formula I, $R^6$ is piperidin-4-yl.
In certain embodiments of formula I, $R^6$ is 1-methyl-piperidin-4-yl.
In certain embodiments of formula I, $R^6$ is tert-butyl.
In certain embodiments of formula I, $R^6$ is 2-hydroxy-2-methyl-propyl.
In certain embodiments of formula I, $R^6$ is cyclobutyl.
In certain embodiments of formula I, $R^6$ is 1-methyl-cyclobutyl.
In certain embodiments of formula I, $R^6$ is 2-hydroxy-propyl.
In certain embodiments of formula I, $R^6$ is 1-cyano-cyclopropyl.
In certain embodiments of formula I, $R^6$ is 3,3-difluoro-cyclobutyl.
In certain embodiments of formula I, $R^6$ is cyclopropylmethyl.
In certain embodiments of formula I, $R^6$ is 3-fluoro-cyclobutyl.
In certain embodiments of formula I, $R^6$ is 2,2-difluoroethyl.

In certain embodiments of formula I, $R^5$ and $R^6$ together with the nitrogen atom to which they are attached form a three- to seven-membered ring that is optionally includes an additional heteroatom selected from O, N and S(O)$_n$, and which is optionally substituted with one, two or three groups independently selected from $C_{1-6}$alkyl, halo-$C_{1-6}$alkyl, $C_{1-6}$alkoxy, halo-$C_{1-6}$alkoxy, hydroxy, hydroxy-$C_{1-6}$alkyl, halo, nitrile, $C_{1-6}$alkyl-carbonyl, $C_{1-6}$alkyl-sulfonyl, $C_{3-6}$cycloalkyl, $C_{3-6}$cycloalkyl-$C_{1-6}$alkyl, $C_{3-6}$cycloalkyl-carbonyl, or heterocyclyl, or two of the groups together with the atoms to which they are attached may form a five or six-membered ring.

In embodiments of formula I wherein $R^5$ and $R^6$ together with the nitrogen atom to which they are attached form a three- to seven-membered ring that is optionally includes an additional heteroatom selected from O, N and S(O)$_n$, such ring may be: azetidinyl; pyrrolidinyl; piperidinyl; piperazinyl; morpholinyl; thiomorpholinyl; azepinyl; 3-oxa-8-azabicyclo[3.2.1]oct-8-yl; 2-oxa-5-aza-bicyclo[2.2.1]hept-5-yl; or 8-oxa-3-aza-bicyclo[3.2.1]oct-3-yl; each optionally substituted as defined herein.

In embodiments of formula I wherein $R^5$ and $R^6$ together with the nitrogen atom to which they are attached form a three- to seven-membered ring that is optionally includes an additional heteroatom selected from O, N and S(O)$_n$, such ring may be: azetidinyl; pyrrolidinyl; piperidinyl; piperazinyl; or morpholinyl; each optionally substituted as defined herein.

In certain embodiments of formula I, $R^5$ and $R^6$ together with the nitrogen atom to which they are attached form a morpholinyl group that is optionally substituted once or twice with groups independently selected from $C_{1-6}$alkyl, halo-$C_{1-6}$alkyl, $C_{1-6}$alkoxy, halo-$C_{1-6}$alkoxy, hydroxy, hydroxy-$C_{1-6}$alkyl, halo, nitrile, $C_{1-6}$alkyl-carbonyl, $C_{1-6}$alkyl-sulfonyl, $C_{3-6}$cycloalkyl, $C_{3-6}$cycloalkyl-$C_{1-6}$alkyl, $C_{3-6}$cycloalkyl-carbonyl, amino, or heterocyclyl, or the two groups together with the atoms to which they are attached may form a five or six-membered ring.

In certain embodiments of formula I, $R^5$ and $R^6$ together with the nitrogen atom to which they are attached form a morpholinyl group.

In certain embodiments of formula I, $R^5$ and $R^6$ together with the nitrogen atom to which they are attached form a piperidinyl group that is optionally substituted once or twice with groups independently selected from $C_{1-6}$alkyl, halo-$C_{1-6}$alkyl, $C_{1-6}$alkoxy, halo-$C_{1-6}$alkoxy, hydroxy, hydroxy-$C_{1-6}$alkyl, halo, nitrile, $C_{1-6}$alkyl-carbonyl, $C_{1-6}$alkyl-sulfonyl, $C_{3-6}$cycloalkyl, $C_{3-6}$cycloalkyl-$C_{1-6}$alkyl, $C_{3-6}$cycloalkyl-carbonyl, amino, or heterocyclyl, or the two groups together with the atoms to which they are attached may form a five or six-membered ring.

In certain embodiments of formula I, $R^5$ and $R^6$ together with the nitrogen atom to which they are attached form a piperazinyl group that is optionally substituted once or twice with groups independently selected from $C_{1-6}$alkyl, halo-$C_{1-6}$alkyl, $C_{1-6}$alkoxy, halo-$C_{1-6}$alkoxy, hydroxy, hydroxy-$C_{1-6}$alkyl, halo, nitrile, $C_{1-6}$alkyl-carbonyl, $C_{1-6}$alkyl-sulfonyl, $C_{3-6}$cycloalkyl, $C_{3-6}$cycloalkyl-$C_{1-6}$alkyl, $C_{3-6}$cycloalkyl-carbonyl, amino, or heterocyclyl, or the two groups together with the atoms to which they are attached may form a five or six-membered ring.

In certain embodiments of formula I, $R^5$ and $R^6$ together with the nitrogen atom to which they are attached form a pyrrolidinyl group that is optionally substituted once or twice with groups independently selected from $C_{1-6}$alkyl, halo-$C_{1-6}$alkyl, $C_{1-6}$alkoxy, halo-$C_{1-6}$alkoxy, hydroxy, hydroxy-$C_{1-6}$alkyl, halo, nitrile, $C_{1-6}$alkyl-carbonyl, $C_{1-6}$alkyl-sulfonyl, $C_{3-6}$cycloalkyl, $C_{3-6}$cycloalkyl-$C_{1-6}$alkyl, $C_{3-6}$cycloalkyl-carbonyl, amino, or heterocyclyl, or the two groups together with the atoms to which they are attached may form a five or six-membered ring.

In certain embodiments of formula I, $R^5$ and $R^6$ together with the nitrogen atom to which they are attached form a group selected from: morpholin-4-yl; 4-hydroxy-piperidin-1-yl; octahydro-pyrido[1,2-a]pyrazin-2-yl; 2-hydroxy-piperidin-1-yl; 4,4-dimethyl-piperidin-1-yl; 3,5-dimethyl-piperidin-1-yl; 1-hydroxy-1-methyl-ethyl)-piperidin-1-yl; 3-hydroxy-pyrrolidin-1-yl; 4-methyl-piperidin-1-yl; piperidin-1-yl; azetidin-1-yl; 4,4-difluoro-piperidin-1-yl; 3-methyl-piperidin-1-yl; 4-methoxy-piperidin-1-yl; 3,3-difluoro-piperidin-1-yl; 4-cyano-piperidin-1-yl; 4-fluoro-piperidin-1-yl; 3-methoxy-piperidin-1-yl; 4-ethyl-piperazin-1-yl; 4-acetyl-piperazin-1-yl; 3-trifluoromethyl-piperidin-1-yl; 4-tert-butyl-piperidin-1-yl; 2-hydroxy-ethyl)-piperazin-1-yl; 2-methyl-pyrrolidin-1-yl; 4-hydroxymethyl-piperidin-1-yl; 2-methyl-piperidin-1-yl; pyrrolidin-1-yl; 4-methanesulfonyl-piperazin-1-yl; 3-trifluoromethyl-pyrrolidin-1-yl; 4-(2,2,2-trifluoro-ethyl)-piperazin-1-yl; 2-methyl-morpholin-4-yl; (2,6-dimethyl-morpholin-4-yl; 2,2-diethyl-morpholin-4-yl; 3-hydroxymethyl-morpholin-4-yl; 2-isobutyl-morpholin-4-yl; 2-hydroxymethyl-morpholin-4-yl; 3,3-dimethyl-morpholin-4-yl; 4-methyl-piperazin-1-yl; 4-isopropyl-piperazin-1-yl; piperazin-1-yl; 3-oxa-8-aza-bicyclo[3.2.1]oct-8-yl; (S)-3-methyl-morpholin-4-yl; 2-oxa-5-aza-bicyclo[2.2.1]hept-5-yl; 8-oxa-3-aza-bicyclo[3.2.1]oct-3-yl; (R)-3-methyl-morpholin-4-yl; 4-cyclopropanecarbonyl-piperazin-1-yl; 4-(1-hydroxy-1-methyl-ethyl)-piperidin-1-yl; 4-cyclobutyl-piperazin-1-yl; (R)-3-hydroxy-pyrrolidin-1-yl; 4-oxetan-3-yl-piperazin-1-yl; 3-morpholin-4-yl-azetidin-1-yl; 4-(1-methyl-piperidin-4-yl)-piperazin-1-yl; 3,3-difluoro-azetidin-1-yl; 4-dimethylamino-piperidin-1-yl; 4-piperidin-4-yl-piperazin-1-yl; (4,4-difluoro-piperidin-1-yl; (3-morpholin-4-yl-azetidin-1-yl; 2-oxa-6-aza-spiro[3.3]hept-6-yl; 2-oxa-5-aza-bicyclo[2.2.1]hept-5-yl); 4-methoxy-piperidin-1-yl); [1,4]oxazepan-4-yl; 2R,6S)-2,6-dimethyl-morpholin-4-yl; 3-hydroxy-azetidin-1-yl; 3-cyano-pyrrolidin-1-yl; 3,5-dimethyl-piperazin-1-yl; (3R,5S)-dimethyl-piperazin-1-yl; 3-Fluoro-pyrrolidin-1-yl; (S)-3-Fluoro-pyrrolidin-1-yl; piperazin-1-yl; 3,3-Difluoro-pyrrolidin-1-yl; 3,3-Difluoro-azetidin-1-yl; 2,2,6,6-tetrafluoro-morpholin-4-yl; 2-methoxymethyl-pyrrolidin-1-yl; (S)-2-methoxymethyl-pyrrolidin-1-yl; (1S,4S)-2-oxa-5-azabicyclo[2.2.1]heptan-5-yl; (3S,4S)-3,4-difluoropyrrolidin-1-yl; 3,4-difluoropyrrolidin-1-yl; and 3-methoxypyrrolidin-1-yl.

In certain embodiments of formula I, $R^5$ and $R^6$ together with the nitrogen atom to which they are attached form a group selected from: morpholin-4-yl; 4-hydroxy-piperidin-1-yl; octahydro-pyrido[1,2-a]pyrazin-2-yl; 2-hydroxy-piperidin-1-yl; 4,4-dimethyl-piperidin-1-yl; 3,5-dimethyl-piperidin-1-yl; 1-hydroxy-1-methyl-ethyl)-piperidin-1-yl; 3-hydroxy-pyrrolidin-1-yl; 4-methyl-piperidin-1-yl; piperidin-1-yl; azetidin-1-yl; 4,4-difluoro-piperidin-1-yl; 3-methyl-piperidin-1-yl; 4-methoxy-piperidin-1-yl; 3,3-difluoro-piperidin-1-yl; 4-cyano-piperidin-1-yl; 4-fluoro-piperidin-1-yl; 3-methoxy-piperidin-1-yl; 4-ethyl-piperazin-1-yl; 4-acetyl-piperazin-1-yl; 3-trifluoromethyl-piperidin-1-yl; 4-tert-butyl-piperidin-1-yl; 2-hydroxy-ethyl)-piperazin-1-yl; 2-methyl-pyrrolidin-1-yl; 4-hydroxymethyl-piperidin-1-yl; 2-methyl-piperidin-1-yl; pyrrolidin-1-yl; 4-methanesulfonyl-piperazin-1-yl; 3-trifluoromethyl-pyrrolidin-1-yl; 4-(2,2,2-trifluoro-ethyl)-piperazin-1-yl; 2-methyl-morpholin-4-yl; (2,6-dimethyl-morpholin-4-yl; 2,2-diethyl-morpholin-4-yl; 3-hydroxymethyl-morpholin-4-yl; 2-isobutyl-morpholin-4-yl; 2-hydroxymethyl-morpholin-4-yl; 3,3-dimethyl-morpholin-4-yl; 4-methyl-piperazin-1-yl; 4-isopropyl-piperazin-1- yl; piperazin-1-yl; 3-oxa-8-aza-bicyclo[3.2.1]oct-8-yl; (S)-3-methyl-morpholin-4-yl; 2-oxa-5-aza-bicyclo[2.2.1]hept-5-yl; 8-oxa-3-aza-bicyclo[3.2.1]oct-3-yl; (R)-3-methyl-morpholin-4-yl; 4-cyclopropanecarbonyl-piperazin-1-yl; 4-(1-hydroxy-1-methyl-ethyl)-piperidin-1-yl; 4-cyclobutyl-piperazin-1-yl; (R)-3-hydroxy-pyrrolidin-1-yl; 4-oxetan-3-yl-piperazin-1-yl; 3-morpholin-4-yl-azetidin-1-yl; 4-(1-methyl-piperidin-4-yl)-piperazin-1-yl; 3,3-difluoro-azetidin-1-yl; 4-dimethylamino-piperidin-1-yl; and 4-piperidin-4-yl-piperazin-1-yl.

In certain embodiments of formula I, $R^5$ and $R^6$ together with the nitrogen atom to which they are attached form morpholin-4-yl.

In certain embodiments of formula I, $R^5$ and $R^6$ together with the nitrogen atom to which they are attached form 4-hydroxy-piperidin-1-yl.

In certain embodiments of formula I, $R^5$ and $R^6$ together with the nitrogen atom to which they are attached form octahydro-pyrido[1,2-a]pyrazin-2-yl.

In certain embodiments of formula I, $R^5$ and $R^6$ together with the nitrogen atom to which they are attached form 2-hydroxy-piperidin-1-yl.

In certain embodiments of formula I, $R^5$ and $R^6$ together with the nitrogen atom to which they are attached form 4,4-dimethyl-piperidin-1-yl.

In certain embodiments of formula I, $R^5$ and $R^6$ together with the nitrogen atom to which they are attached form 3,5-dimethyl-piperidin-1-yl.

In certain embodiments of formula I, $R^5$ and $R^6$ together with the nitrogen atom to which they are attached form 1-hydroxy-1-methyl-ethyl)-piperidin-1-yl.

In certain embodiments of formula I, $R^5$ and $R^6$ together with the nitrogen atom to which they are attached form 3-hydroxy-pyrrolidin-1-yl.

In certain embodiments of formula I, $R^5$ and $R^6$ together with the nitrogen atom to which they are attached form 4-methyl-piperidin-1-yl.

In certain embodiments of formula I, $R^5$ and $R^6$ together with the nitrogen atom to which they are attached form piperidin-1-yl.

In certain embodiments of formula I, $R^5$ and $R^6$ together with the nitrogen atom to which they are attached form azetidin-1-yl.

In certain embodiments of formula I, $R^5$ and $R^6$ together with the nitrogen atom to which they are attached form 4,4-difluoro-piperidin-1-yl.

In certain embodiments of formula I, $R^5$ and $R^6$ together with the nitrogen atom to which they are attached form 3-methyl-piperidin-1-yl.

In certain embodiments of formula I, $R^5$ and $R^6$ together with the nitrogen atom to which they are attached form 4-methoxy-piperidin-1-yl.

In certain embodiments of formula I, $R^5$ and $R^6$ together with the nitrogen atom to which they are attached form 3,3-difluoro-piperidin-1-yl.

In certain embodiments of formula I, $R^5$ and $R^6$ together with the nitrogen atom to which they are attached form 4-cyano-piperidin-1-yl.

In certain embodiments of formula I, $R^5$ and $R^6$ together with the nitrogen atom to which they are attached form 4-fluoro-piperidin-1-yl.

In certain embodiments of formula I, $R^5$ and $R^6$ together with the nitrogen atom to which they are attached form 3-methoxy-piperidin-1-yl.

In certain embodiments of formula I, $R^5$ and $R^6$ together with the nitrogen atom to which they are attached form 4-ethyl-piperazin-1-yl.

In certain embodiments of formula I, $R^5$ and $R^6$ together with the nitrogen atom to which they are attached form 4-acetyl-piperazin-1-yl.

In certain embodiments of formula I, $R^5$ and $R^6$ together with the nitrogen atom to which they are attached form 3-trifluoromethyl-piperidin-1-yl.

In certain embodiments of formula I, $R^5$ and $R^6$ together with the nitrogen atom to which they are attached form 4-tert-butyl-piperidin-1-yl.

In certain embodiments of formula I, $R^5$ and $R^6$ together with the nitrogen atom to which they are attached form.

In certain embodiments of formula I, $R^5$ and $R^6$ together with the nitrogen atom to which they are attached form 2-hydroxy-ethyl)-piperazin-1-yl.

In certain embodiments of formula I, $R^5$ and $R^6$ together with the nitrogen atom to which they are attached form 2-methyl-pyrrolidin-1-yl.

In certain embodiments of formula I, $R^5$ and $R^6$ together with the nitrogen atom to which they are attached form 4-hydroxymethyl-piperidin-1-yl.

In certain embodiments of formula I, $R^5$ and $R^6$ together with the nitrogen atom to which they are attached form 2-methyl-piperidin-1-yl.

In certain embodiments of formula I, $R^5$ and $R^6$ together with the nitrogen atom to which they are attached form pyrrolidin-1-yl.

In certain embodiments of formula I, $R^5$ and $R^6$ together with the nitrogen atom to which they are attached form 4-methanesulfonyl-piperazin-1-yl.

In certain embodiments of formula I, $R^5$ and $R^6$ together with the nitrogen atom to which they are attached form 3-trifluoromethyl-pyrrolidin-1-yl.

In certain embodiments of formula I, $R^5$ and $R^6$ together with the nitrogen atom to which they are attached form 4-(2,2,2-trifluoro-ethyl)-piperazin-1-yl.

In certain embodiments of formula I, $R^5$ and $R^6$ together with the nitrogen atom to which they are attached form 2-methyl-morpholin-4-yl.

In certain embodiments of formula I, $R^5$ and $R^6$ together with the nitrogen atom to which they are attached form (2,6-dimethyl-morpholin-4-yl.

In certain embodiments of formula I, $R^5$ and $R^6$ together with the nitrogen atom to which they are attached form 2,2-diethyl-morpholin-4-yl.

In certain embodiments of formula I, $R^5$ and $R^6$ together with the nitrogen atom to which they are attached form 3-hydroxymethyl-morpholin-4-yl.

In certain embodiments of formula I, $R^5$ and $R^6$ together with the nitrogen atom to which they are attached form 2-isobutyl-morpholin-4-yl.

In certain embodiments of formula I, $R^5$ and $R^6$ together with the nitrogen atom to which they are attached form 2-hydroxymethyl-morpholin-4-yl.

In certain embodiments of formula I, $R^5$ and $R^6$ together with the nitrogen atom to which they are attached form 3,3-dimethyl-morpholin-4-yl.

In certain embodiments of formula I, $R^5$ and $R^6$ together with the nitrogen atom to which they are attached form 4-methyl-piperazin-1-yl.

In certain embodiments of formula I, $R^5$ and $R^6$ together with the nitrogen atom to which they are attached form 4-isopropyl-piperazin-1-yl.

In certain embodiments of formula I, $R^5$ and $R^6$ together with the nitrogen atom to which they are attached form piperazin-1-yl.

In certain embodiments of formula I, $R^5$ and $R^6$ together with the nitrogen atom to which they are attached form 3-oxa-8-aza-bicyclo[3.2.1]oct-8-yl.

In certain embodiments of formula I, $R^5$ and $R^6$ together with the nitrogen atom to which they are attached form (S)-3-methyl-morpholin-4-yl.

In certain embodiments of formula I, $R^5$ and $R^6$ together with the nitrogen atom to which they are attached form 2-oxa-5-aza-bicyclo[2.2.1]hept-5-yl.

In certain embodiments of formula I, $R^5$ and $R^6$ together with the nitrogen atom to which they are attached form 8-oxa-3-aza-bicyclo[3.2.1]oct-3-yl.

In certain embodiments of formula I, $R^5$ and $R^6$ together with the nitrogen atom to which they are attached form (R)-3-methyl-morpholin-4-yl.

In certain embodiments of formula I, $R^5$ and $R^6$ together with the nitrogen atom to which they are attached form 4-cyclopropanecarbonyl-piperazin-1-yl.

In certain embodiments of formula I, $R^5$ and $R^6$ together with the nitrogen atom to which they are attached form 4-(1-hydroxy-1-methyl-ethyl)-piperidin-1-yl.

In certain embodiments of formula I, $R^5$ and $R^6$ together with the nitrogen atom to which they are attached form 4-cyclobutyl-piperazin-1-yl.

In certain embodiments of formula I, $R^5$ and $R^6$ together with the nitrogen atom to which they are attached form (R)-3-hydroxy-pyrrolidin-1-yl.

In certain embodiments of formula I, $R^5$ and $R^6$ together with the nitrogen atom to which they are attached form 4-oxetan-3-yl-piperazin-1-yl.

In certain embodiments of formula I, $R^5$ and $R^6$ together with the nitrogen atom to which they are attached form 3-morpholin-4-yl-azetidin-1-yl.

In certain embodiments of formula I, $R^5$ and $R^6$ together with the nitrogen atom to which they are attached form 4-(1-methyl-piperidin-4-yl)-piperazin-1-yl.

In certain embodiments of formula I, $R^5$ and $R^6$ together with the nitrogen atom to which they are attached form 3,3-difluoro-azetidin-1-yl.

In certain embodiments of formula I, $R^5$ and $R^6$ together with the nitrogen atom to which they are attached form 4-dimethylamino-piperidin-1-yl.

In certain embodiments of formula I, $R^5$ and $R^6$ together with the nitrogen atom to which they are attached form 4-piperidin-4-yl-piperazin-1-yl.

In certain embodiments of formula I, $R^5$ and $R^6$ together with the nitrogen atom to which they are attached form (4,4-difluoro-piperidin-1-yl.

In certain embodiments of formula I, $R^5$ and $R^6$ together with the nitrogen atom to which they are attached form (3-morpholin-4-yl-azetidin-1-yl.

In certain embodiments of formula I, $R^5$ and $R^6$ together with the nitrogen atom to which they are attached form 2-oxa-6-aza-spiro[3.3]hept-6-yl.

In certain embodiments of formula I, $R^5$ and $R^6$ together with the nitrogen atom to which they are attached form 2-oxa-5-aza-bicyclo[2.2.1]hept-5-yl). In certain embodiments of formula I, $R^5$ and $R^6$ together with the nitrogen atom to which they are attached form 4-methoxy-piperidin-1-yl).

In certain embodiments of formula I, $R^5$ and $R^6$ together with the nitrogen atom to which they are attached form [1,4]oxazepan-4-yl.

In certain embodiments of formula I, $R^5$ and $R^6$ together with the nitrogen atom to which they are attached form 2R,6S)-2,6-dimethyl-morpholin-4-yl.

In certain embodiments of formula I, $R^5$ and $R^6$ together with the nitrogen atom to which they are attached form 3-hydroxy-azetidin-1-yl.

In certain embodiments of formula I, $R^5$ and $R^6$ together with the nitrogen atom to which they are attached form 3-cyano-pyrrolidin-1-yl.

In certain embodiments of formula I, $R^5$ and $R^6$ together with the nitrogen atom to which they are attached form 3,5-dimethyl-piperazin-1-yl.

In certain embodiments of formula I, $R^5$ and $R^6$ together with the nitrogen atom to which they are attached form (3R, 5S)-dimethyl-piperazin-1-yl.

In certain embodiments of formula I, $R^5$ and $R^6$ together with the nitrogen atom to which they are attached form 3-Fluoro-pyrrolidin-1-yl.

In certain embodiments of formula I, $R^5$ and $R^6$ together with the nitrogen atom to which they are attached form (S)-3-Fluoro-pyrrolidin-1-yl.

In certain embodiments of formula I, $R^5$ and $R^6$ together with the nitrogen atom to which they are attached form piperazin-1-yl.

In certain embodiments of formula I, $R^5$ and $R^6$ together with the nitrogen atom to which they are attached form 3,3-difluoro-pyrrolidin-1-yl.

In certain embodiments of formula I, $R^5$ and $R^6$ together with the nitrogen atom to which they are attached form 3,3-difluoro-azetidin-1-yl.

In certain embodiments of formula I, $R^5$ and $R^6$ together with the nitrogen atom to which they are attached form 2,2,6,6-tetrafluoro-morpholin-4-yl.

In certain embodiments of formula I, $R^5$ and $R^6$ together with the nitrogen atom to which they are attached form 2-methoxymethyl-pyrrolidin-1-yl. In certain embodiments of formula I, $R^5$ and $R^6$ together with the nitrogen atom to which they are attached form (S)-2-methoxymethyl-pyrrolidin-1-yl.

In certain embodiments of formula I, $R^5$ and $R^6$ together with the nitrogen atom to which they are attached form (1S, 4S)-2-oxa-5-azabicyclo[2.2.1]heptan-5-yl.

In certain embodiments of formula I, $R^5$ and $R^6$ together with the nitrogen atom to which they are attached form (3S, 4S)-3,4-difluoropyrrolidin-1-yl; 3,4-difluoropyrrolidin-1-yl; and 3-methoxypyrrolidin-1-yl.

In certain embodiments of formula I, $R^7$ is halo.
In certain embodiments of formula I, $R^7$ is $C_{1-6}$alkyl.
In certain embodiments of formula I, $R^7$ is $C_{1-6}$alkoxy.
In certain embodiments of formula I, $R^7$ is halo-$C_{1-6}$alkyl.
In certain embodiments of formula I, $R^7$ is halo-$C_{1-6}$alkoxy.
In certain embodiments of formula I, $R^7$ is halo or methoxy.
In certain embodiments of formula I, $R^7$ is fluoro, chloro or methoxy.
In certain embodiments of formula I, $R^7$ is fluoro or chloro.
In certain embodiments of formula I, $R^7$ is methoxy.
In certain embodiments of formula I, $R^7$ is chloro.
In certain embodiments of formula I, $R^7$ is fluoro.
In certain embodiments of formula I, $R^7$ is $C_{1-6}$alkoxy wherein at least one carbon is $C^{11}$.
In certain embodiments of formula I, $R^7$ is $C_{1-6}$alkyl wherein at least one carbon is $C^{11}$.
In certain embodiments of formula I, $R^7$ is $C^{11}$methoxy.
In certain embodiments of formula I, $R^7$ is $C^{11}$methyl.
In certain embodiments of formula I, $R^7$ is halo-$C_{1-6}$alkyl wherein at least one halo is $F^{18}$.
In certain embodiments of formula I, $R^7$ is halo-$C_{1-6}$alkoxy.
In certain embodiments of formula I, $R^7$ is halo-$C_{1-6}$alkoxy wherein at least one halo is $F^{18}$.

In certain embodiments of formula I, $R^7$ is fluoromethoxy.
In certain embodiments of formula I, $R^7$ is 2-fluoroethoxy.
In certain embodiments of formula I, $R^7$ is fluoro-di-deuteromethoxy ($FCD_2O-$).
In certain embodiments of formula I, $R^7$ is 2-fluoro-tetra-deuteroethoxy ($FCD_2CD_2O-$).
In certain embodiments of formula I, $R^7$ is $F^{18}$fluoromethoxy ($F^{18}CH_2O-$).
In certain embodiments of formula I, $R^7$ is 2-$F^{18}$fluoroethoxy ($F^{18}CH_2CH_2O-$).
In certain embodiments of formula I, $R^7$ is $F^{18}$fluoro-di-deuteromethoxy ($F^{18}CD_2O-$).
In certain embodiments of formula I, $R^7$ is 2-$F^{18}$fluoro-tetra-deuteroethoxy ($F^{18}CD_2CD_2O-$).
In certain embodiments of formula I, $R^7$ is $-O^{11}CH_3$, $-CH_2CH_2{}^{18}F$, $-CD_2CD_2{}^{18}F$, $-CH_2CD_2{}^{18}F$, $-CH_2{}^{18}F$, or $-CD_2{}^{18}F$
In certain embodiments of formula I, $R^7$ is $F^{18}$.
In certain embodiments of formula I, the subject compound may be selected from:
 ((3-$^{11}$Cmethoxy-4-((4-(methylamino)-5-(trifluoromethyl)pyrimidin-2-yl)amino)phenyl)(morpholino)methanone);
 (4-((4-(ethylamino)-5-(trifluoromethyl)pyrimidin-2-yl)amino)-2-fluoro-5-(2-$^{18}$Fluoro-ethoxy)phenyl)(morpholino)methanone;
 (4-((4-(ethylamino)-5-(trifluoromethyl)pyrimidin-2-yl)amino)-2-fluoro-5-($^{18}$Fluoro-methoxy)phenyl)(morpholino)methanone;
 (4-((4-(ethylamino)-5-(trifluoromethyl)pyrimidin-2-yl)amino)-2-fluoro-5-$^{11}$Cmethoxyphenyl)(morpholino)methanone;
 (4-((4-(ethylamino)-5-(trifluoromethyl)pyrimidin-2-yl)amino)-2-fluoro-5-(2-$^{18}$Fluoro-ethoxy)phenyl)(morpholino)methanone;
 (4-((4-(ethylamino)-5-(trifluoromethyl)pyrimidin-2-yl)amino)-2-fluoro-5-(2-$^{18}$Fluoro-methoxy)phenyl)(morpholino)methanone;
 (4-(4-(cyclopropylamino)-5-(trifluoromethyl)pyrimidin-2-ylamino)-2-fluoro-5-(2-$^{18}$Fluoro-ethoxy)phenyl)(morpholino) methanone; and
 (4-(4-(cyclopropylamino)-5-(trifluoromethyl)pyrimidin-2-ylamino)-2-fluoro-5-(2-$^{18}$Fluoro-methoxy)phenyl)(morpholino)methanone.
In certain embodiments the LRRK2 PET ligand compound is of formula II:

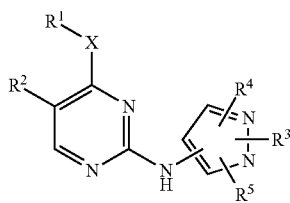

II or pharmaceutically acceptable salts thereof,
wherein:
X is: $-NR^a-$; or $-O-$ wherein $R^a$ is hydrogen or $C_{1-6}$alkyl;
$R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted one or more times with $C_{1-6}$alkyl; $C_{3-6}$cycloalkyl-$C_{1-6}$alkyl wherein the $C_{3-6}$cycloalkyl portion is optionally substituted one or more times with $C_{1-6}$alkyl; heterocyclyl optionally substituted one or more times with $R^7$; or heterocyclyl-$C_{1-6}$alkyl optionally substituted one or more times with $R^7$;
or X and $R^1$ together form $C_{1-6}$alkyl; $C_{1-6}$alkoxy-$C_{1-6}$alkyl; $C_{3-6}$cycloalkyl optionally substituted one or more times with $R^6$; or $C_{3-6}$cycloalkyl-$C_{1-6}$alkyl wherein the $C_{3-6}$cycloalkyl portion is optionally substituted one or more times with $R^6$;
or $R^1$ and $R^a$ together with the atoms to which they are attached may form a three- to six-membered heterocyclic ring optionally substituted one or more times with $R^7$;
$R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; $-OR^b$ wherein $R^b$ is $C_{1-6}$alkyl, $C_{3-6}$cycloalkyl optionally substituted one or more times with $R^6$, or $C_{3-6}$cycloalkyl-$C_{1-6}$alkyl wherein the $C_{3-6}$cycloalkyl portion is optionally substituted one or more times with $R^6$; or $-C(O)-R^c$ wherein $R^c$ is $C_{1-6}$alkyl, $C_{1-6}$alkoxy, amino, or heterocyclyl optionally substituted one or more times with $R^7$;
$R^3$ is: hydrogen; $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonyl $C_{1-6}$alkyl; amino-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; $C_{3-6}$cycloalkyl-sulfonyl wherein the $C_{3-6}$cycloalkyl portion is optionally substituted one or more times with $R^6$; heterocyclyl optionally substituted one or more times with $R^7$; heterocyclyl-$C_{1-6}$alkyl wherein the heterocyclyl portion is optionally substituted one or more times with $R^7$; aryl optionally substituted one or more times with $R^8$; aryl-$C_{1-6}$alkyl wherein the aryl portion is optionally substituted one or more times with $R^8$; heteroaryl optionally substituted one or more times with $R^8$; heteroaryl-$C_{1-6}$alkyl wherein the heteroaryl portion is optionally substituted one or more times with $R^8$; or $-Y-C(O)-R^d$;
Y is $C_{2-6}$alkylene or a bond;
$R^d$ is $C_{1-6}$alkyl, $C_{1-6}$alkoxy, amino, $C_{1-6}$alkyl-amino, di-$C_{1-6}$alkyl-amino, halo-$C_{1-6}$alkyl-amino, di-halo-$C_{1-6}$alkyl-amino, halo-$C_{1-6}$alkyl, hydroxy-$C_{1-6}$alkyl, hydroxy, $C_{1-6}$alkoxy-$C_{1-6}$alkyl, cyano-$C_{1-6}$alkyl, $C_{1-6}$alkyl-sulfonyl$C_{1-6}$alkyl, amino-$C_{1-6}$alkyl, $C_{3-6}$cycloalkyl optionally substituted one or more times with $R^6$, $C_{3-6}$cycloalkyl-$C_{1-6}$alkyl wherein the $C_{3-6}$cycloalkyl portion is optionally substituted one or more times with $R^6$ heterocyclyl optionally substituted one or more times with $R^7$, or heterocyclyl-$C_{1-6}$alkyl wherein the heterocyclyl portion is optionally substituted one or more times with $R^7$;
$R^4$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy; $C_{1-6}$alkoxy-$C_{1-6}$alkyl; hydroxy-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; or $-Y-C(O)-R^d$;
$R^5$ is: hydrogen; or $C_{1-6}$alkyl;
each $R^6$ is independently: $C_{1-6}$alkyl; halo-$C_{1-6}$alkyl; $C_{1-6}$alkoxy; oxo; cyano; halo; or $Y-C(O)-R^d$;
each $R^7$ is independently: $C_{1-6}$alkyl; halo-$C_{1-6}$alkyl; halo; oxo; $C_{1-6}$alkoxy; $C_{1-6}$alkylsulfonyl; $C_{1-6}$alkoxy-$C_{1-6}$alkyl; cyano; $-Y-C(O)-R^d$; heterocyclyl; heterocyclyl-$C_{1-6}$alkyl; $C_{3-6}$cycloalkyl; $C_{3-6}$cycloalkyl-$C_{1-6}$alkyl; or $C_{3-6}$cycloalkylsulfonyl; and
each $R^8$ is independently: oxo; $C_{1-6}$alkyl; halo-$C_{1-6}$alkyl; halo; $C_{1-6}$alkyl-sulfonyl; $C_{1-6}$alkoxy; $C_{1-6}$alkoxy-$C_{1-6}$alkyl;

cyano; heterocyclyl; heterocyclyl-$C_{1-6}$alkyl; —Y—C(O)—$R^d$; $C_{3-6}$cycloalkyl, $C_{3-6}$cycloalkyl-$C_{1-6}$alkyl, or $C_{3-6}$cycloalkyl-sulfonyl.

In certain embodiments of formula II, X is —$NR^a$— or —O—.

In certain embodiments of formula II, X is —$NR^a$.

In certain embodiments of formula II, X is —O—.

In certain embodiments of formula II, X is —NH— or —O—.

In certain embodiments of formula II, X is —NH—.

In certain embodiments of formula II, X is —O—.

In certain embodiments of formula II, $R^a$ is hydrogen.

In certain embodiments of formula II, $R^a$ is $C_{1-6}$alkyl.

In certain embodiments of formula II, $R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; or heterocyclyl-$C_{1-6}$alkyl.

In certain embodiments of formula II, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; $C_{3-6}$cycloalkyl; or $C_{3-6}$cycloalkyl-$C_{1-6}$alkyl.

In certain embodiments of formula II, $R^1$ is: $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl.

In certain embodiments of formula II, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; tetrahydrofuranyl; tetrahydro furanyl-$C_{1-6}$alkyl; oxetanyl; or oxetan-$C_{1-6}$alkyl.

In certain embodiments of formula II, $R^1$ is: $C_{1-6}$alkyl; halo-$C_{1-6}$alkyl; $C_{1-6}$alkoxy-$C_{1-6}$alkyl; amino-$C_{1-6}$alkyl; or $C_{1-6}$alkylsulfonyl-$C_{1-6}$alkyl.

In certain embodiments of formula II, $R^1$ is $C_{1-6}$alkyl or halo-$C_{1-6}$alkyl.

In certain embodiments of formula II, $R^1$ is $C_{1-6}$alkyl.

In certain embodiments of formula II, $R^1$ is halo-$C_{1-6}$alkyl.

In certain embodiments of formula II, $R^1$ is $C_{1-6}$alkoxy-$C_{1-6}$alkyl.

In certain embodiments of formula II, $R^1$ is amino-$C_{1-6}$alkyl.

In certain embodiments of formula II, $R^1$ is $C_{1-6}$alkylsulfonyl-$C_{1-6}$alkyl.

In certain embodiments of formula II, $R^1$ is $C_{3-6}$cycloalkyl optionally substituted with $C_{1-6}$alkyl.

In certain embodiments of formula II, $R^1$ is $C_{3-6}$cycloalkyl-$C_{1-6}$alkyl wherein the $C_{3-6}$cycloalkyl portion is optionally substituted with $C_{1-6}$alkyl.

In certain embodiments of formula II, $R^1$ is heterocyclyl or heterocyclyl-$C_{1-6}$alkyl.

In embodiments of formula II wherein $R^1$ is heterocyclyl or heterocyclyl-$C_{1-6}$alkyl, such heterocyclyl may be piperidinyl, piperazinyl, morpholinyl, tetrahydropyranyl, pyrrolidinyl, tetrahydrofuranyl or oxetanyl, each optionally substituted as defined herein.

In embodiments of formula II wherein $R^1$ is heterocyclyl or heterocyclyl-$C_{1-6}$alkyl, such heterocyclyl may be tetrahydropyranyl, piperidinyl, tetrahydrofuranyl or oxetanyl, each optionally substituted as defined herein.

In certain embodiments of formula II, $R^1$ is tetrahydrofuranyl.

In certain embodiments of formula II, $R^1$ is tetrahydropyranyl.

In certain embodiments of formula II, $R^1$ is tetrahydrofuranyl-$C_{1-6}$alkyl or oxetanyl.

In certain embodiments of formula II, $R^1$ is tetrahydrofuranyl-$C_{1-6}$alkyl.

In certain embodiments of formula II, $R^1$ is oxetanyl.

In certain embodiments of formula II, $R^1$ is or oxetan-$C_{1-6}$alkyl.

In certain embodiments of formula II, $R^1$ is: methyl; ethyl; n-propyl; isopropyl; isobutyl; 3,3-dimethylpropyl; cyclopropyl; cyclobutyl; cyclopentyl; cyclohexyl; cyclopropylmethyl; cyclobutylmethyl; cyclopentylmethyl; cyclopropylethyl; methoxyethyl; oxetanyl; tetrahydropyranyl; 2,2-difluoroethyl; or tetrahydrofuranylmethyl.

In certain embodiments of formula II, $R^1$ is: methyl; ethyl; n-propyl; isopropyl; isobutyl; 3,3-dimethylpropyl; cyclopentyl; cyclohexyl; cyclopropylmethyl; cyclobutylmethyl; cyclopentylmethyl; cyclopropylethyl; methoxyethyl; oxetanyl; tetrahydropyranyl; 2,2-difluoroethyl; or tetrahydrofuranylmethyl.

In certain embodiments of formula II, $R^1$ is: methyl; ethyl; n-propyl; isopropyl; isobutyl; 3,3-dimethylpropyl; cyclopentyl; cyclohexyl; cyclopentylmethyl; methoxyethyl; oxetanyl; tetrahydropyranyl; or tetrahydrofuranylmethyl.

In certain embodiments of formula II, $R^1$ is 2,2-difluoroethyl.

In certain embodiments of formula II, $R^1$ is: methyl; ethyl; n-propyl; isopropyl; or isobutyl.

In certain embodiments of formula II, $R^1$ is methyl or ethyl.

In certain embodiments of formula II, $R^1$ is methyl.

In certain embodiments of formula II, $R^1$ is ethyl.

In certain embodiments of formula II, $R^1$ is: cyclopropyl; cyclobutyl; cyclopentyl; cyclohexyl; cyclopropylmethyl; cyclobutylmethyl; cyclopentylmethyl; or cyclopropylethyl.

In certain embodiments of formula II, $R^1$ is: cyclopentyl; cyclohexyl; or cyclopentylmethyl.

In certain embodiments of formula II, $R^1$ is: cyclopropyl.

In certain embodiments of formula II, $R^1$ and $R^a$ together with the atoms to which they are attached may form a three- to six-membered heterocyclic ring.

In certain embodiments of formula II, $R^1$ and $R^a$ together with the atoms to which they are attached may form a three-membered heterocyclic ring.

In certain embodiments of formula II, $R^1$ and $R^a$ together with the atoms to which they are attached may form a four-membered heterocyclic ring.

In certain embodiments of formula II, $R^1$ and $R^a$ together with the atoms to which they are attached may form a five-membered heterocyclic ring.

In certain embodiments of formula II, $R^1$ and $R^a$ together with the atoms to which they are attached may form a six-membered heterocyclic ring.

In certain embodiments of formula II, X and $R^1$ together form $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl.

In certain embodiments of formula II, X and $R^1$ together form $C_{1-6}$alkyl.

In certain embodiments of formula II, X and $R^1$ together form $C_{3-6}$cycloalkyl optionally substituted with $C_{1-6}$alkyl.

In certain embodiments of formula II, X and $R^1$ together form $C_{3-6}$cycloalkyl-$C_{1-6}$alkyl wherein the $C_{3-6}$cycloalkyl portion is optionally substituted with $C_{1-6}$alkyl.

In certain embodiments of formula II, $R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; —$OR^b$ wherein $R^b$ is $C_{1-6}$alkyl, $C_{3-6}$cycloalkyl optionally substituted with $C_{1-6}$alkyl, or $C_{3-6}$cycloalkyl- $C_{1-6}$alkyl wherein the $C_{3-6}$cycloalkyl portion is optionally substituted with $C_{1-6}$alkyl; or —C(O)—R$^c$.

In certain embodiments of formula II, R$^2$ is: halo; $C_{1-6}$alkoxy; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; oxetanyl; or oxetan-$C_{1-6}$alkyl.

In certain embodiments of formula II, R$^2$ is: halo; $C_{1-6}$alkoxy; halo-$C_{1-6}$alkyl; cyano; $C_{2-6}$alkynyl; $C_{2-6}$alkenyl; $C_{3-6}$cycloalkyl; or $C_{3-6}$cycloalkyl-$C_{1-6}$alkyl.

In certain embodiments of formula II, R$^2$ is: halo; $C_{1-6}$alkoxy; halo-$C_{1-6}$alkyl; cyano; $C_{3-6}$cycloalkyl; or $C_{3-6}$cycloalkyl-$C_{1-6}$alkyl.

In certain embodiments of formula II, R$^2$ is: halo; $C_{1-6}$alkoxy; halo-$C_{1-6}$alkyl; $C_{3-6}$cycloalkyl; or $C_{3-6}$cycloalkyl-$C_{1-6}$alkyl.

In certain embodiments of formula II, R$^2$ is: halo; halo-$C_{1-6}$alkyl or cyano. In certain embodiments of formula II, R$^2$ is: fluoro; bromo; chloro; iodo; trifluoromethyl; or cyano.

In certain embodiments of formula II, R$^2$ is: chloro; trifluoromethyl; or cyano.

In certain embodiments of formula II, R$^2$ is: halo; or halo-$C_{1-6}$alkyl.

In certain embodiments of formula II, R$^2$ is $C_{1-6}$alkyl.

In certain embodiments of formula II, R$^2$ is halo.

In certain embodiments of formula II, R$^2$ is $C_{1-6}$alkoxy.

In certain embodiments of formula II, R$^2$ is halo-$C_{1-6}$alkoxy.

In certain embodiments of formula II, R$^2$ is halo-$C_{1-6}$alkyl.

In certain embodiments of formula II, R$^2$ is $C_{3-6}$cycloalkyl.

In certain embodiments of formula II, R$^2$ is $C_{3-6}$cycloalkyl-$C_{1-6}$alkyl.

In certain embodiments of formula II, R$^2$ is tetrahydrofuranyl.

In certain embodiments of formula II, R$^2$ is tetrahydrofuranyl-$C_{1-6}$alkyl.

In certain embodiments of formula II, R$^2$ is oxetanyl.

In certain embodiments of formula II, R$^2$ is oxetan-$C_{1-6}$alkyl.

In certain embodiments of formula II, R$^2$ is fluoro, chloro or bromo.

In certain embodiments of formula II, R$^2$ is chloro.

In certain embodiments of formula II, R$^2$ is fluoro.

In certain embodiments of formula II, R$^2$ is bromo.

In certain embodiments of formula II, R$^2$ is bromo.

In certain embodiments of formula II, R$^2$ is iodo.

In certain embodiments of formula II, R$^2$ is trifluoromethyl.

In certain embodiments of formula II, R$^2$ is methoxy.

In certain embodiments of formula II, R$^2$ is cyano.

In certain embodiments of formula II, R$^2$ is $C_{2-6}$alkynyl.

In certain embodiments of formula II, R$^2$ is $C_{2-6}$alkenyl.

In certain embodiments of formula II, R$^2$ is —OR$^b$ wherein R$^b$ is $C_{1-6}$alkyl, $C_{3-6}$cycloalkyl optionally substituted with $C_{1-6}$alkyl, or $C_{3-6}$cycloalkyl-$C_{1-6}$alkyl wherein the $C_{3-6}$cycloalkyl portion is optionally substituted with $C_{1-6}$alkyl.

In certain embodiments of formula I, R$^2$ is —C(O)—R$^c$ wherein R$^c$ is $C_{1-6}$alkyl, $C_{1-6}$alkoxy, amino, or heterocyclyl.

In certain embodiments of formula II, R$^3$ is: $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonyl$C_{1-6}$alkyl; amino-$C_{1-6}$alkyl; $C_{3-6}$cycloalkyl optionally substituted one or more times with R$^6$; $C_{3-6}$cycloalkyl-$C_{1-6}$alkyl wherein the $C_{3-6}$cycloalkyl portion is optionally substituted one or more times with R$^6$; heterocyclyl optionally substituted one or more times with R$^7$; heterocyclyl-$C_{1-6}$alkyl wherein the heterocyclyl portion is optionally substituted one or more times with R$^7$; aryl optionally substituted one or more times with R$^8$; heteroaryl optionally substituted one or more times with R$^8$; or —Y—C(O)—R$^d$.

In certain embodiments of formula II, R$^3$ is: hydrogen; $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonylalkyl; amino-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; heterocyclyl-$C_{1-6}$alkyl; aryl; heteroaryl; or —C(O)—R$^c$.

In certain embodiments of formula II, R$^3$ is: $C_{1-6}$alkyl; halo-$C_{1-6}$alkyl; hydroxy-$C_{1-6}$alkyl; $C_{1-6}$alkoxy-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; heterocyclyl-$C_{1-6}$alkyl; or —C(O)—R$^b$ wherein R$^b$ is $C_{1-6}$alkyl, $C_{1-6}$alkoxy, amino, or heterocyclyl.

In certain embodiments of formula II, R$^3$ is: $C_{1-6}$alkyl; hydroxy-$C_{1-6}$alkyl; $C_{1-6}$alkoxy-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; heterocyclyl-$C_{1-6}$alkyl; or —C(O)—R$^c$ wherein R$^c$ is $C_{1-6}$alkyl, $C_{1-6}$alkoxy, amino, or heterocyclyl.

In certain embodiments of formula II, R$^3$ is: $C_{1-6}$alkyl; hydroxy-$C_{1-6}$alkyl; $C_{1-6}$alkoxy-$C_{1-6}$alkyl; $C_{3-6}$cycloalkyl optionally substituted one or more times with R$^6$; $C_{3-6}$cycloalkyl-$C_{1-6}$alkyl wherein the $C_{3-6}$cycloalkyl portion is optionally substituted one or more times with R$^6$; heterocyclyl optionally substituted one or more times with R$^7$; heterocyclyl-$C_{1-6}$alkyl wherein the heterocyclyl portion is optionally substituted one or more times with R$^7$; or —C(O)—R$^d$.

In certain embodiments of formula II, R$^3$ is: $C_{1-6}$alkyl; hydroxy-$C_{1-6}$alkyl; $C_{1-6}$alkoxy-$C_{1-6}$alkyl; heterocyclyl; heterocyclyl-$C_{1-6}$alkyl; or —C(O)—R$^c$ wherein R$^c$ is $C_{1-6}$alkyl, $C_{1-6}$alkoxy, amino, or heterocyclyl.

In certain embodiments of formula II, R$^3$ is: $C_{1-6}$alkyl; hydroxy-$C_{1-6}$alkyl; $C_{1-6}$alkoxy-$C_{1-6}$alkyl; heterocyclyl; or heterocyclyl-$C_{1-6}$alkyl.

In certain embodiments of formula II, R$^3$ is: $C_{1-6}$alkyl; hydroxy-$C_{1-6}$alkyl; or $C_{1-6}$alkoxy-$C_{1-6}$alkyl.

In embodiments of formula II wherein R$^3$ is heterocyclyl or heterocyclyl-$C_{1-6}$alkyl, such heterocyclyl may be piperidinyl, piperazinyl, morpholinyl, tetrahydropyranyl, pyrrolidinyl, tetrahydrofuranyl or oxetanyl.

In embodiments of formula II wherein R$^3$ is heterocyclyl or heterocyclyl-$C_{1-6}$alkyl, such heterocyclyl may be piperidinyl, piperazinyl, morpholinyl, tetrahydropyranyl, pyrrolidinyl, azetidinyl, tetrahydrofuranyl or oxetanyl, each optionally substituted one or more times, or one or two times, with R$^7$ as defined herein.

In embodiments of formula II wherein R$^3$ is heterocyclyl or heterocyclyl-$C_{1-6}$alkyl, such heterocyclyl may be piperidinyl, morpholinyl, tetrahydropyranyl, tetrahydrofuranyl or oxetanyl.

In embodiments of formula II wherein R$^3$ is heterocyclyl or heterocyclyl-$C_{1-6}$alkyl, such heterocyclyl may be piperidinyl, pyrrolidinyl, azetidinyl, morpholinyl, tetrahydropyranyl, tetrahydrofuranyl or oxetanyl, each optionally substituted one or more times, or one or two times, with R$^7$ as defined herein.

In certain embodiments of formula II, R$^3$ is: methyl; ethyl; n-propyl; isopropyl; 2-methoxy-ethyl; oxetan-3-yl; 2-(morpholin-4-yl)-ethyl; 2-hydroxy-2-methyl-propan-1-yl; tetrahydropyran-4-yl; or morpholin-4-yl-carbonyl.

In certain embodiments of formula I, $R^3$ is: methyl; ethyl; n-propyl; isopropyl; 2-methoxy-ethyl; oxetan-3-yl; 2-(morpholin-4-yl)-ethyl; 2-hydroxy-2-methyl-propan-1-yl; or tetrahydropyran-4-yl.

In certain embodiments of formula II, $R^3$ is hydrogen.

In certain embodiments of formula II, $R^3$ is $C_{1-6}$alkyl.

In certain embodiments of formula II, $R^3$ is halo-$C_{1-6}$alkyl.

In certain embodiments of formula I, $R^3$ is halo-$C_{1-6}$alkyl wherein at least one halo is $F^{18}$.

In certain embodiments of formula I, $R^3$ is 2-fluoroethyl.

In certain embodiments of formula I, $R^3$ is 2-$F^{18}$fluoroethyl.

In certain embodiments of formula I, $R^3$ is 2-$F^{18}$fluoro-tetra-deuteroethyl ($F^{18}CD_2CD_2$-).

In certain embodiments of formula II, $R^3$ is $C_{2-6}$alkenyl.

In certain embodiments of formula II, $R^3$ is $C_{2-6}$alkynyl.

In certain embodiments of formula II, $R^3$ is hydroxy-$C_{1-6}$alkyl.

In certain embodiments of formula II, $R^3$ is $C_{1-6}$alkoxy-$C_{1-6}$alkyl.

In certain embodiments of formula II, $R^3$ is $C_{3-6}$cycloalkyl optionally substituted one or more times with $R^6$.

In certain embodiments of formula II, $R^3$ is $C_{3-6}$cycloalkyl optionally substituted with $C_{1-6}$alkyl.

In certain embodiments of formula II, $R^3$ is $C_{3-6}$cycloalkyl-$C_{1-6}$alkyl wherein the $C_{3-6}$cycloalkyl portion is optionally substituted one or more times with $R^6$.

In certain embodiments of formula II, $R^3$ is $C_{3-6}$cycloalkyl-$C_{1-6}$alkyl wherein the $C_{3-6}$cycloalkyl portion is optionally substituted with $C_{1-6}$alkyl.

In certain embodiments of formula II, $R^3$ is heterocyclyl optionally substituted one or more times with $R^7$.

In certain embodiments of formula II, $R^3$ is heterocyclyl.

In certain embodiments of formula II, $R^3$ is heterocyclyl-$C_{1-6}$alkyl wherein the heterocyclyl portion is optionally substituted one or more times with $R^7$.

In certain embodiments of formula II, $R^3$ is heterocyclyl-$C_{1-6}$alkyl.

In certain embodiments of formula II, $R^3$ is —C(O)—$R^c$.

In certain embodiments of formula II, $R^3$ is cyano-$C_{1-6}$alkyl.

In certain embodiments of formula II, $R^3$ is $C_{1-6}$alkylsulfonyl.

In certain embodiments of formula II, $R^3$ is $C_{1-6}$alkylsulfonyl-$C_{1-6}$alkyl.

In certain embodiments of formula II, $R^3$ is amino-$C_{1-6}$alkyl.

In certain embodiments of formula II, $R^3$ is aryl optionally substituted one or more times with $R^8$.

In certain embodiments of formula II, $R^3$ is aryl.

In certain embodiments of formula II, $R^3$ is phenyl optionally substituted one or more times, or one or two times, with $R^8$.

In certain embodiments of formula II, $R^3$ is heteroaryl optionally substituted one or more times, or one or two times, with $R^8$.

In certain embodiments of formula II, $R^3$ is heteroaryl.

In certain embodiments of formula II, $R^3$ is $C_{3-6}$cycloalkylsulfonyl wherein the $C_{3-6}$cycloalkyl portion is optionally substituted one or more times with $R^6$.

In certain embodiments of formula II, $R^3$ is: hydrogen; methyl; ethyl; propyl; isopropyl; butyl; cyclopropyl; cyclopropylmethyl; cyclobutyl; methanesulfonyl; ethylsulfonyl; cyclopropylsulfonyl; sec-butylsulfonyl; morpholin-4-yl-ethyl; oxetan-3-yl; 2-methoxyethyl; 2-hydroxy-2-methyl-propyl; 3-hydroxy-2-methyl-propan-2-yl; 2-methoxy-propyl; tetrahydro-2H-pyran-4-yl; tetrahydrofuran-3-yl; 2,6-dimethyltetrahydro-2H-pyran-4-yl; tetrahydro-2H-pyran-3-yl); phenyl; 4-(methylsulfonyl)phenyl); 4-cyano-phenyl; 4-fluoro-phenyl; 4-chloro-phenyl; 3,5-difluorophenyl; 4-(dimethylamino-carbonyl)-phenyl); 4-(cyclopropylsulfonyl)phenyl; 2,2,2-trifluoroethyl; 2-fluoroethyl; difluoroethyl; 2-dimethyl-1,3-dioxan-5-yl; 1-methyl-cyclopropyl-carbonyl; 3-methylpyridin-4-yl; 2-methylpyridin-4-yl; pyridin-2-yl; pyrimidin-2-yl; pyrimidin-5-yl; pyridin-2-ylmethyl; 1-(pyridin-2-yl)ethyl; cyclopropylsulfonyl; 1-cyano-1-methyl-ethyl (also called 2-cyano-propan-2-yl); 2-cyanoethyl; 1-cyano-ethyl; 2-cyano-2-methyl-propyl; 1-(2,2,2-trifluoroethyl)piperidin-4-yl; 1-(methylsulfonyl)azetidin-3-yl; (3-methyloxetan-3-yl)methyl; (1S,5S)-8-oxabicyclo[3.2.1]octan-3-yl; 1-(oxetan-3-yl)piperidin-4-yl; 1-acetyl-piperidin-4-yl; 1-(cyclopropyl-carbonyl)-piperidin-4-yl; 1-methyl-piperidin-4-yl; 1-methyl-2-oxo-piperidin-5-yl; 2-oxo-piperidin-5-yl; 1-(isopropyl-carbonyl)-piperidin-4-yl; 1-(oxetan-3-yl)azetidin-3-yl; 1-(cyclopropyl-carbonyl)-piperidin-4-yl; 2-methoxycyclopentyl; 3-methoxycyclopentyl; 1-methoxy-2-methylpropan-2-yl; tetrahydro-2H-1,1-dioxothiopyran-4-yl; 3-fluoro-1-(oxetan-3-yl)piperidin-4-yl; 1-methoxypropan-2-yl; 1-(2,2,2-trifluoroethyl)azetidin-3-yl); 1-(oxetan-3-yl)pyrrolidin-3-yl; 1-isopropylazetidin-3-yl; 3-fluoro-1-methylpiperidin-4-yl; 1-ethyl-3-fluoropiperidin-4-yl; 1-methylpyrrolidin-3-yl; 2-methoxyethyl)piperidin-4-yl); 1-methyl-1-(methylamino-carbonyl)-ethyl; 2-methyl-2-morpholino-propyl; 4,4-difluorocyclohexyl; morpholin-4-yl-carbonyl; dimethylamino-carbonyl-methyl; methylamino-carbonyl-methyl; 1-methyl-1-(dimethylamino-carbonyl)-ethyl; pyrrolidin-'-yl-carbonyl; 1-cyano-cyclopropyl; 1-(pyrrolidin-1-yl-carbonyl)-ethyl; 1-(dimethylamino-carbonyl)-ethyl; 1-(methoxy-carbonyl)-ethyl; 1-(tert-butylamino-carbonyl)-1-methyl-ethyl; 1-(2,2,2-trifluoroethyllamino-carbonyl)-1-methyl-ethyl; 1-(ethylamino-carbonyl)-1-methyl-ethyl; 1-(cyclopropylmethylamino-carbonyl)-1-methyl-ethyl; 1-(ethylamino-carbonyl)-cyclobutyl; 1-(isopropylamino-carbonyl)-1-methyl-ethyl; 1-cyano-cyclobutyl; 2-methoxy-1-methyl-ethyl; 1-methyl-1-(methoxy-carbonyl)-ethyl; 2-methoxy-2-methyl-propan-1-yl; 1-(oxetan-3-yl)-pyrrolidin-3-yl; isopropylsulfonyl; butane-2-sulfonyl; 1-(2-fluoroethyl)-piperidin-4-yl; 3-fluoro-1-methyl-piperidin-4-yl; 1-ethyl-3-fluoro-piperidin-4-yl; pyridin-3-ylmethyl; 6-methyl-pyridin-2-ylmethyl; 2-(morpholin-1-yl)-1,1,dimethyl-ethyl; pyrimidin-2-yl-methyl; 3-fluoro-1-(oxetan-3-yl)-piperidin-4-yl; 1-(oxetan-3-yl)-piperidin-3-yl; 1-([1,3]Dioxolan-2-ylmethyl)-piperidin-4-yl; pyridazin-3-ylmethyl; piperidin-3-yl; pyrazin-2-ylmethyl; 2-hydroxy-3-methyl-butan-1-yl; 1-([1,3]Dioxolan-2-ylmethyl)-pyrrolidin-3-yl; pyrimidin-4-ylmethyl; 1-methyl-1H-pyrazol-3-ylmethyl; 1-methyl-1-(4H-[1,2,4]triazol-3-yl)-ethyl; 1-methyl-1-(5-methyl-4H-[1,2,4]triazol-3-yl)-ethyl; 3-fluoro-piperidin-4-yl; 2-hydroxy-cyclopentyl; dimethyl-[1,3]dioxan-5-yl, 2-(5-methyl-1,3,4-oxadiazol-2-yl)propan-2-yl; 2-(4-methyl-4H-1,2,4-triazol-3-yl)propan-2-yl; 2-(1-methyl-1H-1,2,4-triazol-3-yl)propan-2-yl; 2-(1-methyl-1H-pyrazol-4-yl)propan-2-yl; 2-(1-methyl-1H-pyrazol-3-yl)propan-2-yl; 2-(1-methyl-1H-pyrazol-5-yl; 2-(4H-1,2,4-triazol-3-yl)propan-2-yl; or 1-methyl-1H-pyrazole-4-yl.

In certain embodiments of formula II, $R^3$ is: methyl; ethyl; propyl; isopropyl; butyl; cyclopropyl; cyclopropylmethyl; cyclobutyl; methanesulfonyl; ethylsulfonyl; cyclopropylsulfonyl; sec-butylsulfonyl; morpholin-4-yl-ethyl; oxetan-3-yl; 2-methoxyethyl; 2-hydroxy-2-methyl-propyl; 3-hydroxy-2-methyl-propan-2-yl; 2-methoxy-propyl; tetrahydro-2H-pyran-4-yl; tetrahydrofuran-3-yl; 2,6-dimethyltetrahydro-2H-pyran-4-yl; tetrahydro-2H-pyran-3-yl); phenyl; 4-(methylsulfonyl)phenyl); 4-cyano-phenyl; 4-fluoro-phenyl; 4-chloro-phenyl; 3,5-difluorophenyl; 4-(dimethylamino-carbonyl)-phenyl); 4-(cyclopropylsulfonyl)phenyl; 2,2,2-trifluoroethyl; 2-fluoroethyl; difluoromethyl; 2-dimethyl-1,3-dioxan-5-yl; 1-methyl-cyclopropyl-carbonyl; 3-methylpyridin-4-yl; 2-methylpyridin-4-yl; pyridin-2-yl; pyrimidin-2-yl; pyrimidin-5-yl; pyridin-2-ylmethyl; 1-(pyridin-2-yl)ethyl; cyclopropylsulfonyl; 1-cyano-1-methyl-ethyl (also called 2-cyano-propan-2-yl); 2-cyano-ethyl; 1-cyano-ethyl; 2-cyano-2-methyl-propyl; 1-(2,2,2-trifluoroethyl)piperidin-4-yl; 1-(methylsulfonyl)azetidin-3-yl; (3-methyloxetan-3-yl)methyl; (1S,5S)-8-oxabicyclo[3.2.1]octan-3-yl; 1-(oxetan-3-yl)piperidin-4-yl; 1-acetyl-piperidin-4-yl; 1-(cyclopropyl-carbonyl)-piperidin-4-yl; 1-methyl-piperidin-4-yl; 1-methyl-2-oxo-piperidin-5-yl; 2-oxo-piperidin-5-yl; 1-(isopropyl-carbonyl)-piperidin-4-yl; 1-(oxetan-3-yl) azetidin-3-yl; 1-(cyclopropyl-carbonyl)-piperidin-4-yl; 2-methoxycyclopentyl; 3-methoxycyclopentyl; 1-methoxy-2-methylpropan-2-yl; tetrahydro-2H-1,1-dioxo-thiopyran-4-yl; 3-fluoro-1-(oxetan-3-yl)piperidin-4-yl; 1-methoxypropan-2-yl; 1-(2,2,2-trifluoroethyl)azetidin-3-yl); 1-(oxetan-3-yl)pyrrolidin-3-yl; 1-isopropylazetidin-3-yl; 3-fluoro-1-methylpiperidin-4-yl; 1-ethyl-3-fluoropiperidin-4-yl; 1-methylpyrrolidin-3-yl; 2-methoxyethyl)piperidin-4-yl); 1-methyl-1-(methylamino-carbonyl)-ethyl; 2-methyl-2-morpholino-propyl; 4,4-difluorocyclohexyl; morpholin-4-yl-carbonyl; dimethylamino-carbonyl-methyl; methylamino-carbonyl-methyl; 1-methyl-1-(dimethylamino-carbonyl)-ethyl; pyrrolidin-'-yl-carbonyl; 1-cyano-cyclopropyl; 1-(pyrrolidin-'-yl-carbonyl)-ethyl; 1-(dimethylamino-carbonyl)-ethyl; 1-(methoxy-carbonyl)-ethyl; 1-(tert-butylamino-carbonyl)-1-methyl-ethyl; 1-(2,2,2-trifluoro ethylamino-carbonyl)-1-methyl-ethyl; 1-(ethylamino-carbonyl)-1-methyl-ethyl; 1-(cyclopropylmethylamino-carbonyl)-1-methyl-ethyl; 1-(ethylamino-carbonyl)-cyclobutyl; 1-(isopropylamino-carbonyl)-1-methyl-ethyl; 1-cyano-cyclobutyl; 2-methoxy-1-methyl-ethyl; 1-methyl-1-(methoxy-carbonyl)-ethyl; 2-methoxy-2-methyl-propan-1-yl; 1-(oxetan-3-yl)-pyrrolidin-3-yl; isopropylsulfonyl; butane-2-sulfonyl; 1-(2-fluoro ethyl)-piperidin-4-yl; 3-fluoro-1-methyl-piperidin-4-yl; 1-ethyl-3-fluoro-piperidin-4-yl; pyridin-3-ylmethyl; 6-methyl-pyridin-2-ylmethyl; 2-(morpholin-1-yl)-1,1, dimethyl-ethyl; pyrimidin-2-yl-methyl; 3-fluoro-1-(oxetan-3-yl)-piperidin-4-yl; 1-(oxetan-3-yl)-piperidin-3-yl; 1-([1,3] Dioxolan-2-ylmethyl)-piperidin-4-yl; pyridazin-3-ylmethyl; piperidin-3-yl; pyrazin-2-ylmethyl; 2-hydroxy-3-methyl-butan-1-yl; 1-([1,3]Dioxolan-2-ylmethyl)-pyrrolidin-3-yl; pyrimidin-4-ylmethyl; 1-methyl-1H-pyrazol-3-ylmethyl; 1-methyl-1-(4H-[1,2,4]triazol-3-yl)-ethyl; 1-methyl-1-(5-methyl-4H-[1,2,4]triazol-3-yl)-ethyl; 3-fluoro-piperidin-4-yl; 2-hydroxy-cyclopentyl; dimethyl-[1,3]dioxan-5-yl; 2-(5-methyl-1,3,4-oxadiazol-2-yl)propan-2-yl; 2-(4-methyl-4H-1,2,4-triazol-3-yl)propan-2-yl; 2-(1-methyl-1H-1,2,4-triazol-3-yl)propan-2-yl; 2-(1-methyl-1H-pyrazol-4-yl) propan-2-yl; 2-(1-methyl-1H-pyrazol-3-yl)propan-2-yl; 2-(1-methyl-1H-pyrazol-5-yl; 2-(4H-1,2,4-triazol-3-yl)propan-2-yl; or 1-methyl-1H-pyrazole-4-yl.

In certain embodiments of formula II, $R^3$ is: hydrogen; methyl; ethyl; n-propyl; isopropyl; 2-methoxy-ethyl; oxetan-3-yl; 2-hydroxy-2-methyl-propan-1-yl; tetrahydropyran-4-yl; or morpholin-4-yl-carbonyl.

In certain embodiments of formula II, $R^3$ is: methyl; ethyl; n-propyl; isopropyl; 2-methoxy-ethyl; oxetan-3-yl; 2-hydroxy-2-methyl-propan-1-yl; or tetrahydropyran-4-yl.

In certain embodiments of formula II, $R^3$ is: methyl; ethyl; isopropyl; 2-methoxy-ethyl; oxetan-3-yl; or 2-hydroxy-2-methyl-propan-1-yl.

In certain embodiments of formula II, $R^3$ is: methyl; ethyl; or isopropyl.

In certain embodiments of formula II, $R^3$ is hydrogen.
In certain embodiments of formula II, $R^3$ is methyl.
In certain embodiments of formula II, $R^3$ is ethyl.
In certain embodiments of formula II, $R^3$ is n-propyl.
In certain embodiments of formula II, $R^3$ is isopropyl.
In certain embodiments of formula II, $R^3$ is 2-methoxy-ethyl.
In certain embodiments of formula II, $R^3$ is oxetan-3-yl.
In certain embodiments of formula II, $R^3$ is 2-hydroxy-2-methyl-propan-1-yl.
In certain embodiments of formula II, $R^3$ is tetrahydropyran-4-yl.
In certain embodiments of formula II, $R^3$ is morpholin-4-yl-carbonyl.
In certain embodiments of formula II, $R^3$ is butyl.
In certain embodiments of formula II, $R^3$ is cyclopropyl.
In certain embodiments of formula II, $R^3$ is cyclopropylmethyl.
In certain embodiments of formula II, $R^3$ is cyclobutyl.
In certain embodiments of formula II, $R^3$ is methanesulfonyl.
In certain embodiments of formula II, $R^3$ is ethylsulfonyl.
In certain embodiments of formula II, $R^3$ is cyclopropylsulfonyl.
In certain embodiments of formula II, $R^3$ is sec-butylsulfonyl.
In certain embodiments of formula II, $R^3$ is morpholin-4-yl-ethyl.
In certain embodiments of formula II, $R^3$ is 2-hydroxy-2-methyl-propyl.
In certain embodiments of formula II, $R^3$ is 3-hydroxy-2-methyl-propan-2-yl.
In certain embodiments of formula II, $R^3$ is 2-methoxypropyl.
In certain embodiments of formula II, $R^3$ is tetrahydro-2H-pyran-4-yl.
In certain embodiments of formula II, $R^3$ is tetrahydrofuran-3-yl.
In certain embodiments of formula II, $R^3$ is 2,6-dimethyltetrahydro-2H-pyran-4-yl.
In certain embodiments of formula II, $R^3$ is tetrahydro-2H-pyran-3-yl).
In certain embodiments of formula II, $R^3$ is phenyl.
In certain embodiments of formula II, $R^3$ is 4-(methylsulfonyl)phenyl).
In certain embodiments of formula II, $R^3$ is 4-cyano-phenyl.
In certain embodiments of formula II, $R^3$ is 4-fluoro-phenyl.
In certain embodiments of formula Iv, $R^3$ is 4-chloro-phenyl.
In certain embodiments of formula II, $R^3$ is 3,5-difluorophenyl.
In certain embodiments of formula II, $R^3$ is 4-(dimethylamino-carbonyl)-phenyl).
In certain embodiments of formula II, $R^3$ is 4-(cyclopropylsulfonyl)phenyl.
In certain embodiments of formula II, $R^3$ is 2,2,2-trifluoroethyl.
In certain embodiments of formula II, $R^3$ is 2-fluoroethyl.
In certain embodiments of formula II, $R^3$ is difluoromethyl.

In certain embodiments of formula II, $R^3$ is 2-dimethyl-1,3-dioxan-5-yl.

In certain embodiments of formula II, $R^3$ is 1-methyl-cyclopropyl-carbonyl.

In certain embodiments of formula II, $R^3$ is 3-methylpyridin-4-yl.

In certain embodiments of formula II, $R^3$ is 2-methylpyridin-4-yl.

In certain embodiments of formula II, $R^3$ is pyridin-2-yl.

In certain embodiments of formula II, $R^3$ is pyrimidin-2-yl.

In certain embodiments of formula II, $R^3$ is pyrimidin-5-yl.

In certain embodiments of formula II, $R^3$ is pyridin-2-ylmethyl.

In certain embodiments of formula II, $R^3$ is 1-(pyridin-2-yl)ethyl.

In certain embodiments of formula II, $R^3$ is cyclopropyl-sulfonyl.

In certain embodiments of formula II, $R^3$ is 1-cyano-1-methyl-ethyl (also called 2-cyano-propan-2-yl).

In certain embodiments of formula II, $R^3$ is 2-cyano-ethyl.

In certain embodiments of formula II, $R^3$ is 1-cyano-ethyl.

In certain embodiments of formula II, $R^3$ is 2-cyano-2-methyl-propyl.

In certain embodiments of formula II, $R^3$ is 1-(2,2,2-trifluoroethyl)piperidin-4-yl.

In certain embodiments of formula II, $R^3$ is 1-(methylsulfonyl)azetidin-3-yl.

In certain embodiments of formula II, $R^3$ is (3-methyloxetan-3-yl)methyl.

In certain embodiments of formula II, $R^3$ is (1S,5S)-8-oxabicyclo[3.2.1]octan-3-yl.

In certain embodiments of formula II, $R^3$ is 1-(oxetan-3-yl)piperidin-4-yl.

In certain embodiments of formula II, $R^3$ is 1-acetyl-piperidin-4-yl.

In certain embodiments of formula II, $R^3$ is 1-(cyclopropyl-carbonyl)-piperidin-4-yl.

In certain embodiments of formula II, $R^3$ is 1-methyl-piperidin-4-yl.

In certain embodiments of formula II, $R^3$ is 1-methyl-2-oxo-piperidin-5-yl.

In certain embodiments of formula II, $R^3$ is 2-oxo-piperidin-5-yl.

In certain embodiments of formula II, $R^3$ is 1-(isopropyl-carbonyl)-piperidin-4-yl.

In certain embodiments of formula II, $R^3$ is 1-(oxetan-3-yl)azetidin-3-yl.

In certain embodiments of formula II, $R^3$ is 1-(cyclopropyl-carbonyl)-piperidin-4-yl.

In certain embodiments of formula II, $R^3$ is 2-methoxycyclopentyl.

In certain embodiments of formula II, $R^3$ is 3-methoxycyclopentyl.

In certain embodiments of formula II, $R^3$ is 1-methoxy-2-methylpropan-2-yl.

In certain embodiments of formula II, $R^3$ is tetrahydro-2H-1,1-dioxo-thiopyran-4-yl.

In certain embodiments of formula II, $R^3$ is 3-fluoro-1-(oxetan-3-yl)piperidin-4-yl.

In certain embodiments of formula II, $R^3$ is 1-methoxypropan-2-yl.

In certain embodiments of formula II, $R^3$ is 1-(2,2,2-trifluoroethyl)azetidin-3-yl).

In certain embodiments of formula II, $R^3$ is 1-(oxetan-3-yl)pyrrolidin-3-yl.

In certain embodiments of formula II, $R^3$ is 1-isopropylazetidin-3-yl.

In certain embodiments of formula II, $R^3$ is 3-fluoro-1-methylpiperidin-4-yl.

In certain embodiments of formula II, $R^3$ is 1-ethyl-3-fluoropiperidin-4-yl.

In certain embodiments of formula II, $R^3$ is 1-methylpyrrolidin-3-yl.

In certain embodiments of formula II, $R^3$ is 2-methoxyethyl)piperidin-4-yl).

In certain embodiments of formula II, $R^3$ is 1-methyl-1-(methylamino-carbonyl)-ethyl.

In certain embodiments of formula II, $R^3$ is 2-methyl-2-morpholino-propyl.

In certain embodiments of formula II, $R^3$ is 4,4-difluoro-cyclohexyl.

In certain embodiments of formula II, $R^3$ is dimethylamino-carbonyl-methyl.

In certain embodiments of formula II, $R^3$ is methylamino-carbonyl-methyl.

In certain embodiments of formula II, $R^3$ is 1-methyl-1-(dimethylamino-carbonyl)-ethyl.

In certain embodiments of formula II, $R^3$ is pyrrolidin-'-yl-carbonyl.

In certain embodiments of formula II, $R^3$ is 1-cyano-cyclopropyl.

In certain embodiments of formula II, $R^3$ is 1-(pyrrolidin-1-yl-carbonyl)-ethyl.

In certain embodiments of formula II, $R^3$ is 1-(dimethylamino-carbonyl)-ethyl.

In certain embodiments of formula II, $R^3$ is 1-(methoxy-carbonyl)-ethyl.

In certain embodiments of formula II, $R^3$ is 1-(tert-butylamino-carbonyl)-1-methyl-ethyl.

In certain embodiments of formula II, $R^3$ is 1-(2,2,2-trifluoroethylamino-carbonyl)-1-methyl-ethyl.

In certain embodiments of formula II, $R^3$ is 1-(ethylamino-carbonyl)-1-methyl-ethyl.

In certain embodiments of formula II, $R^3$ is 1-(cyclopropylmethylamino-carbonyl)-1-methyl-ethyl.

In certain embodiments of formula II, $R^3$ is 1-(ethylamino-carbonyl)-cyclobutyl.

In certain embodiments of formula II, $R^3$ is 1-(isopropylamino-carbonyl)-1-methyl-ethyl.

In certain embodiments of formula II, $R^3$ is 1-cyano-cyclobutyl.

In certain embodiments of formula II, $R^3$ is dimethyl-[1,3]dioxan-5-yl.

In certain embodiments of formula II, $R^3$ is 2-methoxy-2-methyl-propan-1-yl.

In certain embodiments of formula II, $R^3$ is 2-methoxy-1-methyl-ethyl.

In certain embodiments of formula II, $R^3$ is 1-methyl-1-(methoxy-carbonyl)-ethyl.

In certain embodiments of formula II, $R^3$ is 1-oxetan-3-yl-pyrrolidin-3-yl.

In certain embodiments of formula II, $R^3$ is isopropylsulfonyl.

In certain embodiments of formula II, $R^3$ is butane-2-sulfonyl.

In certain embodiments of formula II, $R^3$ is 1-(2-fluoroethyl)-piperidin-4-yl.

In certain embodiments of formula II, $R^3$ is 3-fluoro-1-methyl-piperidin-4-yl.

In certain embodiments of formula II, $R^3$ is 1-ethyl-3-fluoro-piperidin-4-yl. In certain embodiments of formula II, $R^3$ is pyridin-3-ylmethyl.

In certain embodiments of formula II, $R^3$ is 6-methyl-pyridin-2-ylmethyl.

In certain embodiments of formula II, $R^3$ is 2-(morpholin-1-yl)-1,1,dimethyl-ethyl.

In certain embodiments of formula II, $R^3$ is pyrimidin-2-yl-methyl.

In certain embodiments of formula II, $R^3$ is 3-fluoro-1-(oxetan-3-yl)-piperidin-4-yl.

In certain embodiments of formula II, $R^3$ is 1-(oxetan-3-yl)-piperidin-3-yl.

In certain embodiments of formula II, $R^3$ is 1-([1,3]Dioxolan-2-ylmethyl)-piperidin-4-yl.

In certain embodiments of formula II, $R^3$ is pyridazin-3-ylmethyl.

In certain embodiments of formula II, $R^3$ is piperidin-3-yl.

In certain embodiments of formula II, $R^3$ is pyrazin-2-ylmethyl.

In certain embodiments of formula II, $R^3$ is 2-hydroxy-3-methyl-butan-1-yl.

In certain embodiments of formula II, $R^3$ is 1-([1,3]dioxolan-2-ylmethyl)-pyrrolidin-3-yl.

In certain embodiments of formula II, $R^3$ is pyrimidin-4-ylmethyl.

In certain embodiments of formula II, $R^3$ is 1-methyl-1H-pyrazol-3-ylmethyl.

In certain embodiments of formula II, $R^3$ is 1-methyl-1-(5-methyl-4H-[1,2,4]triazol-3-yl)-ethyl.

In certain embodiments of formula II, $R^3$ is 1-methyl-1-(4H-[1,2,4]triazol-3-yl)-ethyl.

In certain embodiments of formula II, $R^3$ is 3-fluoro-piperidin-4-yl; 2-hydroxy-cyclopentyl.

In certain embodiments of formula II, $R^3$ is 2-(5-methyl-1,3,4-oxadiazol-2-yl)propan-2-yl.

In certain embodiments of formula II, $R^3$ is 2-(4-methyl-4H-1,2,4-triazol-3-yl)propan-2-yl.

In certain embodiments of formula II, $R^3$ is 2-(1-methyl-1H-1,2,4-triazol-3-yl)propan-2-yl.

In certain embodiments of formula II, $R^3$ is 2-(1-methyl-1H-pyrazol-4-yl)propan-2-yl; 2-(1-methyl-1H-pyrazol-3-yl)propan-2-yl.

In certain embodiments of formula II, $R^3$ is 2-(1-methyl-1H-pyrazol-5-yl.

In certain embodiments of formula II, $R^3$ is 2-(4H-1,2,4-triazol-3-yl)propan-2-yl.

In certain embodiments of formula II, $R^3$ is 1-methyl-1H-pyrazole-4-yl.

In embodiments of formula II wherein $R^3$ is aryl, such aryl may be unsubstituted phenyl or phenyl substituted one or more times with $R^8$, or in certain embodiments, once, twice or three times with a group or groups independently selected from $C_{1-6}$alkyl, halo, halo-$C_{1-6}$alkyl, $C_{1-6}$alkoxy, hydroxy or cyano.

In embodiments of formula II wherein $R^3$ is heteroaryl or heteroaryl-$C_{1-6}$alkyl, such heteroaryl moiety may be pyrrolyl, pyrazolyl, imidazolyl, thiazolyl, oxazolyl, pyridinyl, pyrimidinyl, pyrazinyl, pyridazinyl, isoxazolyl, isothiazolyl, triazolyl, oxadiaolyl, thiadiazolyl or tetrazolyl, each being unsubstituted or substituted once or twice with $R^8$, or in certain embodiments, substituted once or twice with $C_{1-6}$alkyl.

In embodiments of formula II wherein $R^3$ is heteroaryl or heteroaryl-$C_{1-6}$alkyl, such heteroaryl moiety may be pyrazolyl, pyridinyl, pyrimidinyl, pyrazinyl, pyridazinyl, triazolyl or oxadiaolyl each being unsubstituted or substituted once or twice with $R^8$, or in certain embodiments, substituted once or twice with $C_{1-6}$alkyl.

In embodiments of formula II wherein $R^3$ is heteroaryl or heteroaryl-$C_{1-6}$alkyl, such heteroaryl moiety may be pyrrolyl, pyrazolyl, imidazolyl, thiazolyl, oxazolyl, pyridinyl, pyrimidinyl, pyrazinyl or pyridazinyl, each being unsubstituted or substituted one or more times with $R^8$.

In embodiments of formula II wherein $R^3$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^7$.

In embodiments of formula II wherein $R^3$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^7$.

In certain embodiments of formula II, $R^3$ is —Y—C(O)—$R^d$.

In certain embodiments of formula II, Y is a bond.
In certain embodiments of formula II, Y is $C_{2-6}$alkylene.
In certain embodiments of formula II, Y is isopropylidine.
In certain embodiments of formula II, Y is methylene.
In certain embodiments of formula II, Y is ethylene.
In certain embodiments of formula II, Y is —C(CH$_3$)$_2$—.
In certain embodiments of formula II, Y is —CH$_2$—.
In certain embodiments of formula II, Y is —CH(CH$_3$)—.
In certain embodiments of formula II, Y is —CH$_2$—C(CH$_3$)$_2$—.
In certain embodiments of formula II, Y is —C(CH$_3$)$_2$—CH$_2$—.

In certain embodiments of formula II, $R^d$ is $C_{1-6}$alkyl, $C_{1-6}$alkoxy, amino, or heterocyclyl.
In certain embodiments of formula II, $R^d$ is $C_{1-6}$alkyl.
In certain embodiments of formula II, $R^d$ is $C_{1-6}$alkoxy.
In certain embodiments of formula II, $R^d$ is amino.
In certain embodiments of formula II, $R^d$ is halo-$C_{1-6}$alkyl.
In certain embodiments of formula II, $R^d$ is hydroxy-$C_{1-6}$alkyl.
In certain embodiments of formula II, $R^d$ is $C_{1-6}$alkoxy-$C_{1-6}$alkyl.
In certain embodiments of formula II, $R^d$ is cyano-$C_{1-6}$alkyl.
In certain embodiments of formula II, $R^d$ is $C_{1-6}$alkylsulfonyl$C_{1-6}$alkyl.
In certain embodiments of formula II, $R^d$ is amino-$C_{1-6}$alkyl.
In certain embodiments of formula II, $R^d$ is $C_{3-6}$cycloalkyl optionally substituted one or more times with $R^6$.
In certain embodiments of formula II, $R^d$ is $C_{3-6}$cycloalkyl-$C_{1-6}$alkyl wherein the $C_{3-6}$cycloalkyl portion is optionally substituted one or more times with $R^6$.
In certain embodiments of formula II, $R^d$ is heterocyclyl optionally substituted one or more times with $R^7$.
In certain embodiments of formula II, $R^d$ is heterocyclyl-$C_{1-6}$alkyl wherein the heterocyclyl portion is optionally substituted one or more times with $R^7$.

In certain embodiments of formula II, $R^d$ is 1-methyl-cyclopropyl; methylamino; dimethylamino; pyrrolidin-1-yl; methoxy; cyclopropyl-methyl; ethyl; 2,2,2-trifluoro-ethyl; tert-butyl; or isopropyl.

In certain embodiments of formula II, $R^d$ is 1-methyl-cyclopropyl.
In certain embodiments of formula II, $R^d$ is methylamino.
In certain embodiments of formula II, $R^d$ is dimethylamino.
In certain embodiments of formula II, $R^d$ is pyrrolidin-1-yl.
In certain embodiments of formula II, $R^d$ is methoxy.
In certain embodiments of formula II, $R^d$ is cyclopropyl-methyl.
In certain embodiments of formula II, $R^d$ is ethyl.

In certain embodiments of formula II, $R^d$ is 2,2,2-trifluoroethyl.

In certain embodiments of formula II, $R^d$ is tert-butyl.

In certain embodiments of formula II, $R^d$ is isopropyl.

In embodiments of formula II wherein $R^d$ is heterocyclyl or heterocyclyl-$C_{1-6}$alkyl, such heterocyclyl may be piperidinyl, piperazinyl, morpholinyl, tetrahydropyranyl, pyrrolidinyl, azetidinyl, tetrahydrofuranyl or oxetanyl, each optionally substituted one or more times, or one or two times, with $R^7$ as defined herein.

In embodiments of formula II wherein $R^d$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^7$.

In embodiments of formula II wherein $R^d$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^7$.

In certain embodiments of formula II, $R^4$ is: hydrogen; $C_{1-6}$alkyl; halo; halo-$C_{1-6}$alkyl; $C_{1-6}$alkoxy-$C_{1-6}$alkyl; hydroxy-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; or —C(O)—$R^c$ wherein $R^c$ is $C_{1-6}$alkyl, $C_{1-6}$alkoxy, amino, or heterocyclyl.

In certain embodiments of formula II, $R^4$ is: $C_{1-6}$alkyl; halo; halo-$C_{1-6}$alkyl; $C_{1-6}$alkoxy-$C_{1-6}$alkyl; hydroxy-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; or —C(O)—$R^c$ wherein $R^c$ is $C_{1-6}$alkyl, $C_{1-6}$alkoxy, amino, or heterocyclyl.

In certain embodiments of formula II, $R^4$ is: hydrogen; $C_{1-6}$alkyl; halo; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; or —C(O)—$R^c$ wherein $R^c$ is $C_{1-6}$alkyl, $C_{1-6}$alkoxy, amino, or heterocyclyl.

In certain embodiments of formula II, $R^4$ is: hydrogen; $C_{1-6}$alkyl; halo; or $C_{3-6}$cycloalkyl optionally substituted with $C_{1-6}$alkyl.

In certain embodiments of formula II, $R^4$ is hydrogen or $C_{1-6}$alkyl.

In certain embodiments of formula II, $R^4$ is hydrogen.

In certain embodiments of formula II, $R^4$ is $C_{1-6}$alkyl.

In certain embodiments of formula II, $R^4$ is halo.

In certain embodiments of formula II, $R^4$ is cyano.

In certain embodiments of formula II, $R^4$ is halo-$C_{1-6}$alkyl.

In certain embodiments of formula II, $R^4$ is $C_{1-6}$alkoxy-$C_{1-6}$alkyl.

In certain embodiments of formula II, $R^4$ is hydroxy-$C_{1-6}$alkyl.

In certain embodiments of formula II, $R^4$ is $C_{3-6}$cycloalkyl optionally substituted with $C_{1-6}$alkyl.

In certain embodiments of formula II, $R^4$ is hydrogen or methyl.

In certain embodiments of formula II, $R^4$ is $C_{3-6}$cycloalkyl-$C_{1-6}$alkyl wherein the $C_{3-6}$cycloalkyl portion is optionally substituted with $C_{1-6}$alkyl.

In certain embodiments of formula II, $R^4$ is —C(O)—$R^c$ wherein $R^c$ is $C_{1-6}$alkyl, $C_{1-6}$alkoxy, amino, or heterocyclyl.

In certain embodiments of formula II, $R^4$ is —C(O)—$R^c$ wherein $R^c$ is heterocyclyl.

In embodiments of formula II wherein $R^c$ is heterocyclyl, such heterocyclyl may be pyrrolidinyl, piperidinyl, piperazinyl or morpholinyl.

In embodiments of formula II wherein $R^c$ is heterocyclyl, such heterocyclyl may be piperidinyl, piperazinyl or morpholinyl.

In certain embodiments of formula II, $R^4$ is: hydrogen; methyl; isopropyl; cyclopropyl; chloro; or morpholin-4-yl-carbonyl.

In certain embodiments of formula II, $R^4$ is: hydrogen; methyl; isopropyl; cyclopropyl; or chloro.

In certain embodiments of formula II, $R^4$ is hydrogen.

In certain embodiments of formula II, $R^4$ is methyl.

In certain embodiments of formula II, $R^4$ is isopropyl.

In certain embodiments of formula II, $R^4$ is cyclopropyl.

In certain embodiments of formula II, $R^4$ is chloro.

In certain embodiments of formula II, $R^4$ is morpholin-4-yl-carbonyl.

In certain embodiments of formula II, $R^4$ is 2-fluoro-ethyl.

In certain embodiments of formula II, $R^4$ is $C_{3-6}$cycloalkyl optionally substituted one or more times, or one or two times, with $R^6$.

In certain embodiments of formula II, $R^4$ is $C_{3-6}$cycloalkyl-$C_{1-6}$alkyl wherein the $C_{3-6}$cycloalkyl portion is optionally substituted one or more times, or one or two times, with $R^6$.

In certain embodiments of formula II, $R^4$ is —Y—C(O)—$R^d$.

In certain embodiments of formula II, or $R^3$ and $R^4$ together with the atoms to which they are attached may form a 5- or 6-membered ring that optionally includes a heteroatom selected from O, N and S.

In certain embodiments of formula II, $R^5$ is hydrogen.

In certain embodiments of formula II, $R^5$ is $C_{1-6}$alkyl.

In certain embodiments of formula II, $R^5$ is methyl.

In certain embodiments of formula II, each $R^6$ is independently $C_{1-6}$alkyl; halo-$C_{1-6}$alkyl; $C_{1-6}$alkoxy; cyano; or halo.

In certain embodiments of formula II, $R^6$ is $C_{1-6}$alkyl; halo-$C_{1-6}$alkyl; $C_{1-6}$alkoxy; or halo.

In certain embodiments of formula II, $R^6$ is $C_{1-6}$alkyl; halo-$C_{1-6}$alkyl; or halo.

In certain embodiments of formula II, $R^6$ is $C_{1-6}$alkyl.

In certain embodiments of formula II, $R^6$ is halo-$C_{1-6}$alkyl.

In certain embodiments of formula II, $R^6$ is $C_{1-6}$alkoxy.

In certain embodiments of formula II, $R^6$ is cyano.

In certain embodiments of formula II, $R^6$ is halo.

In certain embodiments of formula II, $R^6$ is Y—C(O)—$R^d$.

In certain embodiments of formula II, $R^6$ is oxo.

In certain embodiments of formula II, each $R^7$ is independently $C_{1-6}$alkyl; halo-$C_{1-6}$alkyl; halo; $C_{1-6}$alkylsulfonyl; $C_{1-6}$alkoxy-$C_{1-6}$alkyl; cyano; heterocyclyl; or $C_{3-6}$cycloalkylsulfonyl wherein the $C_{3-6}$cycloalkyl portion is optionally substituted one or more times with $R^6$.

In certain embodiments of formula II, $R^7$ is $C_{1-6}$alkyl.

In certain embodiments of formula II, $R^7$ is halo-$C_{1-6}$alkyl.

In certain embodiments of formula II, $R^7$ is halo.

In certain embodiments of formula II, $R^7$ is $C_{1-6}$alkylsulfonyl.

In certain embodiments of formula II, $R^7$ is $C_{1-6}$alkoxy-$C_{1-6}$alkyl.

In certain embodiments of formula II, $R^7$ is cyano.

In certain embodiments of formula II, $R^7$ is —Y—C(O)—$R^d$.

In certain embodiments of formula II, $R^7$ is heterocyclyl.

In certain embodiments of formula II, $R^7$ is $C_{3-6}$cycloalkylsulfonyl wherein the $C_{3-6}$cycloalkyl portion is optionally substituted one or more times with $R^6$.

In certain embodiments of formula II, $R^7$ is oxo.

In certain embodiments of formula II, $R^7$ is $C_{1-6}$alkoxy.

In certain embodiments of formula II, $R^7$ is heterocyclyl-$C_{1-6}$alkyl.

In certain embodiments of formula II, $R^7$ is $C_{3-6}$cycloalkyl.

In certain embodiments of formula II, $R^7$ is $C_{3-6}$cycloalkyl-$C_{1-6}$alkyl.

In embodiments of formula II wherein $R^7$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl.

In embodiments of formula II wherein $R^7$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl.

In certain embodiments of formula II, each $R^8$ is independently oxo; $C_{1-6}$alkyl; halo-$C_{1-6}$alkyl; halo; $C_{1-6}$alkoxy; $C_{1-6}$alkoxy-$C_{1-6}$alkyl; cyano; $C_{3-6}$cycloalkyl optionally substituted one or more times with $R^6$, $C_{3-6}$cycloalkyl-$C_{1-6}$alkyl wherein the $C_{3-6}$cycloalkyl portion is optionally substituted one or more times with $R^6$, or $C_{3-6}$cycloalkyl-sulfonyl wherein the $C_{3-6}$cycloalkyl portion is optionally substituted one or more times with $R^6$.

In certain embodiments of formula II, $R^8$ is oxo. In certain embodiments of formula II, $R^7$ is $C_{1-6}$alkyl.

In certain embodiments of formula II, $R^7$ is halo-$C_{1-6}$alkyl

In certain embodiments of formula II, $R^7$ is halo. In certain embodiments of formula II, $R^7$ is $C_{1-6}$alkoxy.

In certain embodiments of formula II, $R^7$ is $C_{1-6}$alkoxy-$C_{1-6}$alkyl.

In certain embodiments of formula II, $R^7$ is cyano.

In certain embodiments of formula II, $R^7$ is heterocyclyl.

In certain embodiments of formula II, $R^7$ is —Y—C(O)—$R^d$.

In certain embodiments of formula II, $R^7$ is $C_{3-6}$cycloalkyl optionally substituted one or more times with $R^6$.

In certain embodiments of formula II, $R^7$ is $C_{3-6}$cycloalkyl-$C_{1-6}$alkyl wherein the $C_{3-6}$cycloalkyl portion is optionally substituted one or more times with $R^6$.

In certain embodiments of formula II, $R^7$ is $C_{3-6}$cycloalkyl-sulfonyl wherein the $C_{3-6}$cycloalkyl portion is optionally substituted one or more times with $R^6$.

In certain embodiments of formula II, $R^8$ is oxo.

In certain embodiments of formula II, $R^8$ is $C_{1-6}$alkyl.

In certain embodiments of formula II, $R^8$ is halo-$C_{1-6}$alkyl.

In certain embodiments of formula II, $R^8$ is halo.

In certain embodiments of formula II, $R^8$ is $C_{1-6}$alkyl-sulfonyl.

In certain embodiments of formula II, $R^8$ is $C_{1-6}$alkoxy.

In certain embodiments of formula II, $R^8$ is $C_{1-6}$alkoxy-$C_{1-6}$alkyl.

In certain embodiments of formula II, $R^8$ is cyano; heterocyclyl.

In certain embodiments of formula II, $R^8$ is heterocyclyl-$C_{1-6}$alkyl.

In certain embodiments of formula II, $R^8$ is —Y—C(O)—$R^d$.

In certain embodiments of formula II, $R^8$ is $C_{3-6}$cycloalkyl.

In certain embodiments of formula II, $R^8$ is $C_{3-6}$cycloalkyl-$C_{1-6}$alkyl-$C_{3-6}$cycloalkyl-sulfonyl.

In embodiments of formula II wherein $R^8$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl.

In embodiments of formula II wherein $R^8$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl.

In another embodiment, the LRRK2 PET ligand compound is of formula III:

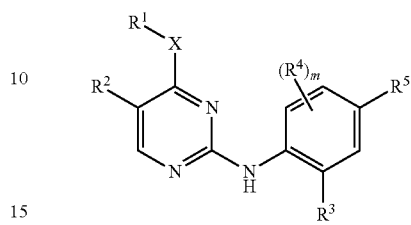

or pharmaceutically acceptable salts thereof,
wherein:
m is from 0 to 3;
X is: —$NR^a$—; —O—; or —$S(O)_r$— wherein r is from 0 to 2 and $R^a$ is hydrogen or $C_{1-6}$alkyl;
$R^1$ is: $C_{1-6}$alkyl; $C_{1-6}$alkenyl; $C_{1-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; oxetanyl; or oxetan-$C_{1-6}$alkyl;

or $R^1$ and $R^a$ together with the atoms to which they are attached may form a three to six membered ring that may optionally include an additional heteroatom selected from O, N and S, and which is substituted with oxo, halo or $C_{1-6}$alkyl;

$R^2$ is: halo; $C_{1-6}$alkoxy; cyano; $C_{1-6}$alkynyl; $C_{1-6}$alkenyl; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; acetyl; oxetanyl; or oxetan-$C_{1-6}$alkyl;

$R^3$ and $R^4$ each independently is: halo; $C_{1-6}$alkyl; $C_{1-6}$alkoxy; halo-$C_{1-6}$alkyl; or halo-$C_{1-6}$alkoxy; and $R^5$ is: $C_{1-6}$alkyl-sulfonyl; cyano; heterocyclyl; heterocyclyl-$C_{1-6}$alkyl; and carboxy.

In certain embodiments of formula III, $R^1$ and $R^a$ together with the atoms to which they are attached may form a three to six membered ring that may optionally include an additional heteroatom selected from O, N and S, and which may be optionally substituted with oxo, halo or $C_{1-6}$alkyl.

In certain embodiments of formula III, $R^1$ and $R^a$ together with the atoms to which they are attached form a five or six membered ring.

In certain embodiments of formula III, $R^1$ and $R^a$ together with the atoms to which they are attached form a pyrrolidinyl, piperidinyl or oxazoladinonyl group.

In certain embodiments of formula III, $R^2$ is acetyl.

In certain embodiments of formula III, when $R^1$ is cyclopropyl, cyclobutyl, cyclopropyl-$C_{1-6}$alkyl or cyclobutyl-$C_{1-6}$alkyl, then X is —O—.

In certain embodiments of formula III, m is from 0 to 2.

In certain embodiments of formula III, m is 0 or 1.

In certain embodiments of formula III, m is 0.

In certain embodiments of formula III, m is 1.

In certain embodiments of formula III, r is 0.

In certain embodiments of formula III, r is 2.

In certain embodiments of formula III, X is —$NR^a$— or —O—.

In certain embodiments of formula III, X is —NR$^a$.
In certain embodiments of formula III, X is —O—.
In certain embodiments of formula III, X is —S(O)$_n$—.
In certain embodiments of formula III, X is —NH— or —O—.

In certain embodiments of formula III, R$^a$ is hydrogen.
In certain embodiments of formula III, R$^a$ is C$_{1-6}$alkyl.
In certain embodiments of formula III, R$^1$ is: C$_{1-6}$alkyl; halo-C$_{1-6}$alkyl; C$_{1-6}$alkoxy-C$_{1-6}$alkyl; amino-C$_{1-6}$alkyl; C$_{1-6}$alkylsulfonyl-C$_{1-6}$alkyl; C$_{3-6}$cycloalkyl; or C$_{3-6}$cycloalkyl-C$_{1-6}$alkyl.

In certain embodiments of formula III, R$^1$ is: C$_{1-6}$alkyl; C$_{3-6}$cycloalkyl optionally substituted with C$_{1-6}$alkyl; or C$_{3-6}$cycloalkyl-C$_{1-6}$alkyl wherein the C$_{3-6}$cycloalkyl portion is optionally substituted with C$_{1-6}$alkyl.

In certain embodiments of formula III, R$^1$ is: C$_{1-6}$alkyl; halo-C$_{1-6}$alkyl; C$_{1-6}$alkoxy-C$_{1-6}$alkyl; amino-C$_{1-6}$alkyl; C$_{1-6}$alkylsulfonyl-C$_{1-6}$alkyl; tetrahydrofuranyl; tetrahydrofuranyl-C$_{1-6}$alkyl; oxetanyl; or oxetan-C$_{1-6}$alkyl.

In certain embodiments of formula III, R$^1$ is: C$_{1-6}$alkyl; halo-C$_{1-6}$alkyl; C$_{1-6}$alkoxy-C$_{1-6}$alkyl; amino-C$_{1-6}$alkyl; or C$_{1-6}$alkylsulfonyl-C$_{1-6}$alkyl.

In certain embodiments of formula III, R$^1$ is C$_{1-6}$alkyl.
In certain embodiments of formula III, R$^1$ is halo-C$_{1-6}$alkyl.
In certain embodiments of formula III, R$^1$ is C$_{1-6}$alkoxy-C$_{1-6}$alkyl.
In certain embodiments of formula III, R$^1$ is amino-C$_{1-6}$alkyl.
In certain embodiments of formula III, R$^1$ is C$_{1-6}$alkylsulfonyl-C$_{1-6}$alkyl optionally substituted with C$_{1-6}$alkyl.
In certain embodiments of formula III, R$^1$ is C$_{3-6}$cycloalkyl optionally substituted with C$_{1-6}$alkyl.
In certain embodiments of formula III, R$^1$ is C$_{3-6}$cycloalkyl-C$_{1-6}$alkyl wherein the C$_{3-6}$cycloalkyl portion is optionally substituted with C$_{1-6}$alkyl.
In certain embodiments of formula III, R$^1$ is tetrahydrofuranyl.
In certain embodiments of formula III, R$^1$ is tetrahydrofuranyl-C$_{1-6}$alkyl; oxetanyl.
In certain embodiments of formula III, R$^1$ is or oxetan-C$_{1-6}$alkyl.

In certain embodiments of formula III, R$^1$ is: methyl; ethyl; n-propyl; isopropyl; isobutyl; 3,3-dimethylpropyl; cyclopropyl; cyclobutyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl.

In certain embodiments of formula III, R$^1$ is: methyl; ethyl; n-propyl; isopropyl; isobutyl; 3,3-dimethylpropyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl.

In certain embodiments of formula III, R$^1$ is: methyl; ethyl; n-propyl; isopropyl; isobutyl; 3,3-dimethylpropyl; cyclopentyl; cyclohexyl; cyclopentylmethyl; methoxyethyl; oxetanyl; or tetrahydrofuranylmethyl.

In certain embodiments of formula III, R$^1$ is: methyl; ethyl; n-propyl; isopropyl; or isobutyl.

In certain embodiments of formula III, R$^1$ is methyl or ethyl.
In certain embodiments of formula III, R$^1$ is methyl.
In certain embodiments of formula III, R$^1$ is ethyl.
In certain embodiments of formula III, R$^1$ is: cyclopropyl; cyclobutyl; cyclopentyl; cyclohexyl; cyclopropylmethyl; cyclobutylmethyl; cyclopentylmethyl; or cyclopropylethyl.
In certain embodiments of formula III, R$^1$ is: cyclopropyl.

In certain embodiments of formula III, R$^1$ is: cyclopentyl; cyclohexyl; or cyclopentylmethyl.

In certain embodiments of formula III, R$^2$ is: halo; C$_{1-6}$alkoxy; halo-C$_{1-6}$alkyl; halo-C$_{1-6}$alkoxy; C$_{3-6}$cycloalkyl wherein the C$_{3-6}$cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl.

In certain embodiments of formula III, R$^2$ is: halo; C$_{1-6}$alkoxy; halo-C$_{1-6}$alkyl; cyano; C$_{1-6}$alkynyl; C$_{1-6}$alkenyl; C$_{3-6}$cycloalkyl; or C$_{3-6}$cycloalkyl-C$_{1-6}$alkyl.

In certain embodiments of formula III, R$^2$ is: halo; C$_{1-6}$alkoxy; halo-C$_{1-6}$alkyl; cyano; C$_{3-6}$cycloalkyl; or C$_{3-6}$cycloalkyl-C$_{1-6}$alkyl.

In certain embodiments of formula III, R$^2$ is: halo; C$_{1-6}$alkoxy; halo-C$_{1-6}$alkyl; C$_{3-6}$cycloalkyl; or C$_{3-6}$cycloalkyl-C$_{1-6}$alkyl.

In certain embodiments of formula III, R$^2$ is: halo; halo-C$_{1-6}$alkyl; or cyano.
In certain embodiments of formula III, R$^2$ is: halo; or halo-C$_{1-6}$alkyl.
In certain embodiments of formula III, R$^2$ is halo.
In certain embodiments of formula III, R$^2$ is C$_{1-6}$alkoxy.
In certain embodiments of formula III, R$^2$ is halo-C$_{1-6}$alkoxy.
In certain embodiments of formula III, R$^2$ is halo-C$_{1-6}$alkyl.
In certain embodiments of formula III, R$^2$ is C$_{3-6}$cycloalkyl.
In certain embodiments of formula III, R$^2$ is C$_{3-6}$cycloalkyl-C$_{1-6}$alkyl.
In certain embodiments of formula III, R$^2$ is tetrahydrofuranyl.
In certain embodiments of formula III, R$^2$ is tetrahydrofuranyl-C$_{1-6}$alkyl.
In certain embodiments of formula III, R$^2$ is oxetanyl.
In certain embodiments of formula III, R$^2$ is oxetan-C$_{1-6}$alkyl.
In certain embodiments of formula III, R$^2$ is halo, trifluoromethyl or cyano.
In certain embodiments of formula III, R$^2$ is chloro, trifluoromethyl or cyano.
In certain embodiments of formula III, R$^2$ is fluoro, chloro or bromo.
In certain embodiments of formula III, R$^2$ is chloro.
In certain embodiments of formula III, R$^2$ is fluoro.
In certain embodiments of formula III, R$^2$ is bromo.
In certain embodiments of formula III, R$^2$ is trifluoromethyl.
In certain embodiments of formula III, R$^2$ is methoxy.
In certain embodiments of formula III, R$^2$ is cyano.
In certain embodiments of formula III, R$^2$ is C$_{1-6}$alkynyl.
In certain embodiments of formula III, R$^2$ is C$_{1-6}$alkenyl.
In certain embodiments of formula III, R$^3$ is: C$_{1-6}$alkyl;
In certain embodiments of formula III, R$^3$ is halo.
In certain embodiments of formula III, R$^3$ is C$_{1-6}$alkyl.
In certain embodiments of formula III, R$^3$ is C$_{1-6}$alkoxy.
In certain embodiments of formula III, R$^3$ is halo-C$_{1-6}$alkyl.
In certain embodiments of formula III, R$^3$ is halo-C$_{1-6}$alkoxy.
In certain embodiments of formula III, R$^3$ is halo or methoxy.
In certain embodiments of formula III, R$^3$ is fluoro, chloro or methoxy.

In certain embodiments of formula III, $R^3$ is fluoro or chloro.

In certain embodiments of formula III, $R^3$ is methoxy.
In certain embodiments of formula III, $R^3$ is methyl
In certain embodiments of formula III, $R^3$ is chloro.
In certain embodiments of formula III, $R^3$ is fluoro.
In certain embodiments of formula III, $R^4$ is: $C_{1-6}$alkyl;
In certain embodiments of formula III, $R^4$ is halo.
In certain embodiments of formula III, $R^4$ is $C_{1-6}$alkyl.
In certain embodiments of formula III, $R^4$ is $C_{1-6}$alkoxy.
In certain embodiments of formula III, $R^4$ is halo-$C_{1-6}$alkyl.
In certain embodiments of formula III, $R^4$ is halo-$C_{1-6}$alkoxy.
In certain embodiments of formula III, $R^4$ is halo or methoxy.
In certain embodiments of formula III, $R^4$ is fluoro, chloro or methoxy.
In certain embodiments of formula III, $R^4$ is fluoro or chloro.
In certain embodiments of formula III, $R^4$ is methoxy.
In certain embodiments of formula III, $R^4$ is methyl
In certain embodiments of formula III, $R^4$ is chloro.
In certain embodiments of formula III, $R^4$ is fluoro.

The invention also provides LRRK2 PET ligand precursor compounds of formula IV:

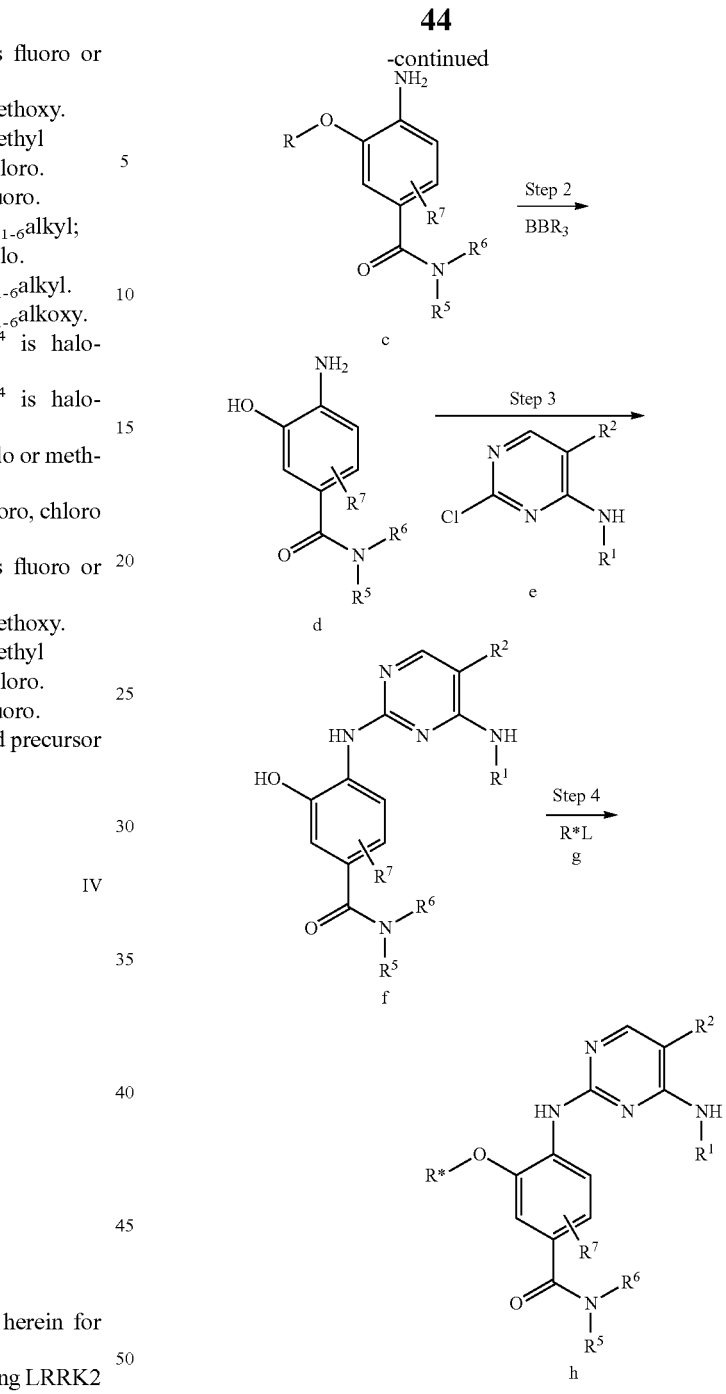

or pharmaceutically acceptable salts thereof,
wherein $R^1$, $R^2$, $R^5$, $R^6$, and $R^7$ are as defined herein for formula I.

The invention also provides a method of preparing LRRK2 PET ligands, shown in Scheme A wherein R is $C_{1-6}$alkyl, R* is $C_{1-6}$alkyl having a $^{11}$C- or $^{18}$F-atom thereon, L is a leaving group, and $R^1$, $R^2$, $R^5$, $R^6$ and $R^7$ are as described herein for Formula I.

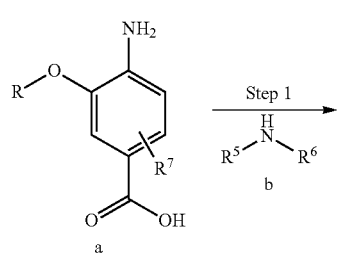

In step 1 of Scheme A, aryl acid compound a is reacted with amine b to provide aryl amide compound c. Amine b in many embodiments may be morpholine. Amide compound c is then de-alkylated in step 2 using boron tribromide or like reagent to afford phenol compound d. An alkylation reaction is then carried out in step 3 by treatment of compound d with pyrimidine compound e to yield aminopyrimidine compound f. In step 4 an O-alkylation is carried out by reacting radiolabeled alkylating agent g with aminopyrimidine compound f to give radiolabeled aminopyrimidine compound g in accordance with the invention. The group R* on alkylating agent may be a $C_{1-6}$alkoxy with a $F^{18}$ or $^{11}$C atom thereon such as —O$^{11}$CH$_3$, —CH$_2$CH$_2$$^{18}$F, —CD$_2$CD$_2$$^{18}$F, —CH$_2$CD$_2$$^{18}$F, —CH$_2$$^{18}$F, —CD$_2$$^{18}$F or the like, and leaving group L may be tosyl or the like.

The method thus may comprise reacting a compound of formula f with a radiolabeled alkylating agent g to provide a radiolabeled aminopyrimidine compound of formula h. The method may further comprise reacting a compound of formula d with a compound of formula e to provide the compound of formula f. The method may further comprise reacting a compound of formula c with boron tribromide to provide the compound of formula f. The method may further comprise reacting a compound of formula a with a compound of formula b to provide the compound of formula c.

Representative compounds in accordance with the methods of the invention are shown in Table 1 below, together with LRRK2 affinity (micromolar).

TABLE 1

| | Name | Structure | Ki μM |
|---|---|---|---|
| 1 | (4-(4-(cyclopropylamino)-5-(trifluoromethyl)pyrimidin-2-ylamino)-2-fluoro-5-(2-fluoroethoxy)phenyl)(morpholino)methanone | 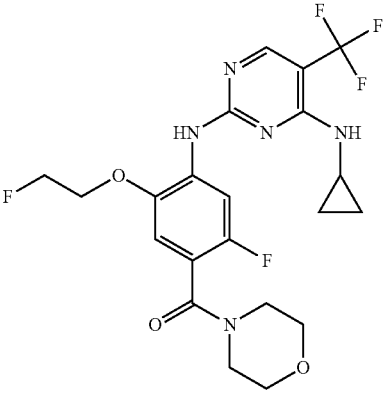 [SMILES: O=C(c1cc(OCCF)c(Nc2ncc(C(F)(F)F)c(NC3CC3)n2)cc1F)N1CCOCC1] | 0.0006 |
| 2 | (5-(fluoromethoxy)-2-methyl-4-(4-(methylamino)-5-(trifluoromethyl)pyrimidin-2-ylamino)phenyl)(morpholino)methanone | 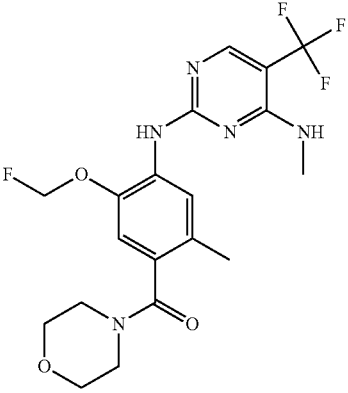 [SMILES: CNc1nc(Nc2cc(C)c(C(=O)N3CCOCC3)cc2OCF)ncc1C(F)(F)F] | 0.0010 |
| 3 | (3,3-difluoropyrrolidin-1-yl)(4-(4-(ethylamino)-5-(trifluoromethyl)pyrimidin-2-ylamino)-5-(2-fluoroethoxy)-2-methoxyphenyl)methanone | 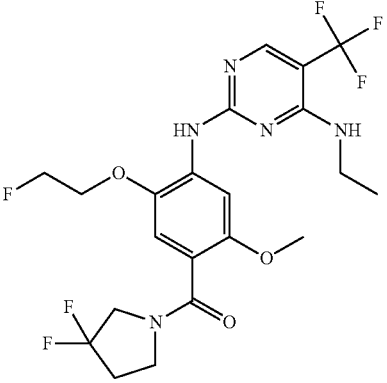 [SMILES: CCNc1nc(Nc2cc(OC)c(C(=O)N3CCC(F)(F)C3)cc2OCCF)ncc1C(F)(F)F] | 0.0010 |

TABLE 1-continued

| Name | Structure | Ki μM |
|---|---|---|
| 4 (5-chloro-4-(4-(ethylamino)-5-(trifluoromethyl)pyrimidin-2-ylamino)-2-(fluoromethoxy)phenyl)(morpholino)methanone | | 0.0015 |
| 5 (5-chloro-4-(4-(ethylamino)-5-(trifluoromethyl)pyrimidin-2-ylamino)-2-(fluoromethoxy)phenyl)(pyrrolidin-1-yl)methanone | | 0.0015 |
| 6 (3,3-difluoropyrrolidin-1-yl)(4-(4-(ethylamino)-5-(trifluoromethyl)pyrimidin-2-ylamino)-5-(fluoromethoxy)-2-methoxyphenyl)methanone | | 0.0004 |
| 7 (5-(fluoromethoxy)-2-methyl-4-(4-(methylamino)-5-(trifluoromethyl)pyrimidin-2-ylamino)phenyl)(pyrrolidin-1-yl)methanone | | 0.0007 |

TABLE 1-continued

| Name | Structure | Ki μM |
|---|---|---|
| 8 (3,3-difluoropyrrolidin-1-yl)(4-(4-(ethylamino)-5-(trifluoromethyl)pyrimidin-2-ylamino)-2,5-dimethoxyphenyl)methanone | | 0.0011 |
| 9 (3,3-difluoropyrrolidin-1-yl)(5-(2-fluoroethoxy)-2-methoxy-4-((4-(methylamino)-5-(trifluoromethyl)pyrimidin-2-yl)amino)phenyl)methanone | | 0.0015 |
| 10 N4-ethyl-N2-(5-fluoro-2-(2-fluoroethoxy)-4-(morpholinomethyl)phenyl)-5-(trifluoromethyl)pyrimidine-2,4-diamine | | 0.0015 |

TABLE 1-continued

| Name | Structure | Ki μM |
|---|---|---|
| 11 (5-(fluoromethoxy)-2-methoxy-4-(4-(methylamino)-5-(trifluoromethyl)pyrimidin-2-ylamino)phenyl)(piperidin-1-yl)methanone | | 0.0016 |
| 12 (4-(4-(ethylamino)-5-(trifluoromethyl)pyrimidin-2-ylamino)-2-fluoro-5-(2-fluoroethoxy)phenyl)(morpholino)methanone | | 0.0020 |
| 13 (5-(2-fluoroethoxy)-2-methyl-4-(4-(methylamino)-5-(trifluoromethyl)pyrimidin-2-ylamino)phenyl)(morpholino)methanone | | 0.0023 |
| 14 (5-(fluoromethoxy)-2-methoxy-4-(4-(methylamino)-5-(trifluoromethyl)pyrimidin-2-ylamino)phenyl)(pyrrolidin-1-yl)methanone | | 0.0032 |

TABLE 1-continued

| | Name | Structure | Ki μM |
|---|---|---|---|
| 15 | N2-(2-(2-fluoroethoxy)-4-(methylsulfonyl)phenyl)-N4-methyl-5-(trifluoromethyl)pyrimidine-2,4-diamine | 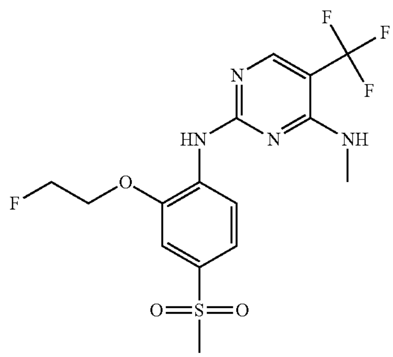 [SMILES: CNc1nc(Nc2ccc(S(C)(=O)=O)cc2OCCF)ncc1C(F)(F)F] | 0.0033 |
| 16 | (4-(4-(ethylamino)-5-(trifluoromethyl)pyrimidin-2-ylamino)-5-fluoro-2-(fluoromethoxy)phenyl)(pyrrolidin-1-yl)methanone | 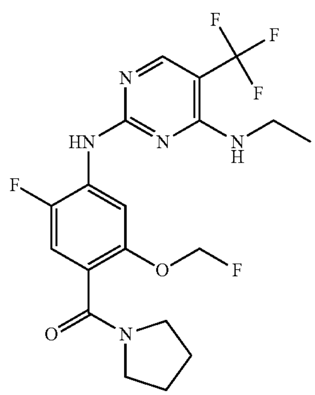 [SMILES: CCNc1nc(Nc2cc(OCF)c(C(=O)N3CCCC3)cc2F)ncc1C(F)(F)F] | 0.0034 |
| 17 | (2-fluoro-5-(2-fluoroethoxy)-4-(4-(methylamino)-5-trifluoromethyl)pyrimidin-2-ylamino)phenyl)(morpholino)methanone | 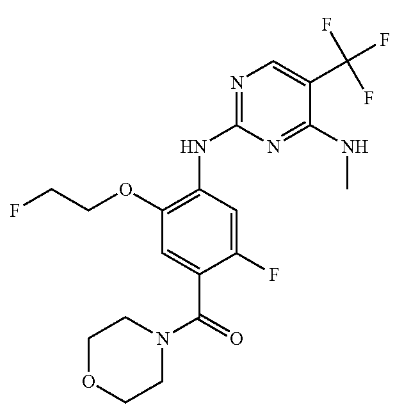 [SMILES: CNc1nc(Nc2cc(F)c(C(=O)N3CCOCC3)cc2OCCF)ncc1C(F)(F)F] | 0.0035 |
| 18 | N2-(5-fluoro-2-(2-fluoroethoxy)-4-(morpholinomethyl)phenyl)-N4-methyl-5-(trifluoromethyl)pyrimidine-2,4-diamine | 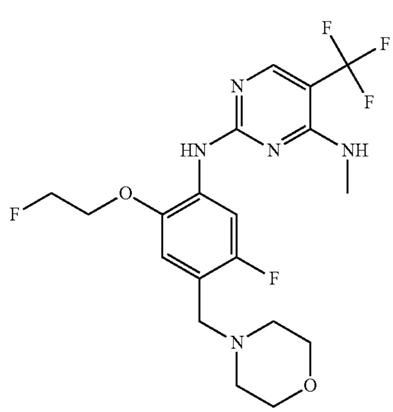 [SMILES: CNc1nc(Nc2cc(F)c(CN3CCOCC3)cc2OCCF)ncc1C(F)(F)F] | 0.0037 |

TABLE 1-continued

| Name | Structure | Ki μM |
|---|---|---|
| 19 5-(fluoromethoxy)-2-methoxy-N,N-dimethyl-4-(4-(methylamino)-5-(trifluoromethyl)pyrimidin-2-ylamino)benzamide | | 0.004 |
| 20 (5-(2-fluoroethoxy)-2-methoxy-4-(4-(methylamino)-5-(trifluoromethyl)pyrimidin-2-ylamino)phenyl)(pyrrolidin-1-yl)methanone | | 0.0047 |
| 21 N2-(2-(2-fluoroethoxy)-4-(morpholinomethyl)phenyl)-N4-methyl-5-(trifluoromethyl)pyrimidine-2,4-diamine | | 0.0066 |
| 22 (2-fluoro-5-(fluoromethoxy)-4-(4-(methylamino)-5-(trifluoromethyl)pyrimidin-2-ylamino)phenyl)(pyrrolidin-1-yl)methanone | | 0.0065 |

TABLE 1-continued

| Name | Structure | Ki μM |
|---|---|---|
| 23 5-chloro-N2-(2-(2-fluoroethoxy)-4-(morpholinomethyl)phenyl)-N4-methylpyrimidine-2,4-diamine | | 0.0089 |
| 24 (4-(5-chloro-4-methoxypyrimidin-2-ylamino)-5-(fluoromethoxy)-2-methylphenyl)(pyrrolidin-1-yl)methanone | | 0.011 |
| 25 5-chloro-N-(2-(2-fluoroethoxy)-4-(morpholinomethyl)phenyl)-4-methoxypyrimidin-2-amine | | 0.012 |
| 26 5-chloro-N-(2-(2-fluoroethoxy)-4-(methylsulfonyl)phenyl)-4-methoxypyrimidin-2-amine | | 0.012 |

TABLE 1-continued

| Name | Structure | Ki μM |
|---|---|---|
| 27 5-chloro-N2-(2-(2-fluoroethoxy)-4-(methylsulfonyl)phenyl)-N4-methylpyrimidine-2,4-diamine | | 0.012 |
| 28 (4-(5-chloro-4-methoxypyrimidin-2-ylamino)-3-(2-fluoroethoxy)phenyl)(morpholino)methanone | | 0.015 |
| 29 N2-(4-(2-fluoroethoxy)-6-morpholinopyridin-3-yl)-N4-methyl-5-(trifluoromethyl)pyrimidine-2,4-diamine | | 0.021 |
| 30 (3-(2-fluoroethoxy)-4-(4-(methylamino)-5-(trifluoromethyl)pyrimidin-2-ylamino)phenyl)(morpholino)methanone | | 0.0023 |

TABLE 1-continued

| Name | Structure | Ki μM |
|---|---|---|
| 31 N2-(1-(1-(2-fluoroethyl)piperidin-4-yl)-5-methyl-1H-pyrazol-4-yl)-N4-methyl-5-(trifluoromethyl)pyrimidine-2,4-diamine | | 0.0042 |
| 32 5-chloro-N-(1-(1-(2-fluoroethyl)piperidin-4-yl)-5-methyl-1H-pyrazol-4-yl)-4-methoxypyrimidin-2-amine | | 0.021 |
| 33 N2-(1-(1-(2-fluoroethyl)piperidin-4-yl)-3-methyl-1H-pyrazol-4-yl)-N4-methyl-5-(trifluoromethyl)pyrimidine-2,4-diamine | | 0.025 |
| 34 N2-(5-(fluoromethyl)-1-methyl-1H-pyrazol-4-yl)-N4-methyl-5-(trifluoromethyl)pyrimidine-2,4-diamine | | 0.024 |

TABLE 1-continued

| Name | Structure | Ki μM |
|---|---|---|
| 35 N2-(1-(2-fluoroethyl)-3-methyl-1H-pyrazol-4-yl)-N4-methyl-5-(trifluoromethyl)pyrimidine-2,4-diamine | | 0.0011 |
| 36 N2-(1-(2-fluoroethyl)-5-methyl-1H-pyrazol-4-yl)-N4-methyl-5-(trifluoromethyl)pyrimidine-2,4-diamine | | 0.0018 |
| 37 (3-(2-fluoroethoxy)-4-(4-(methylamino)-5-(trifluoromethyl)pyrimidin-2-ylamino)phenyl)(morpholino)methanone | | 0.0018 |
| 38 (3-methoxy-4-(4-(methylamino)-5-(trifluoromethyl)pyrimidin-2-ylamino)phenyl)(morpholino)methanone | | 0.0027 |

TABLE 1-continued

| Name | Structure | Ki μM |
|---|---|---|
| 39 (3-(2-fluoroethoxy)-4-((4-(methylamino)-5-(trifluoromethyl)pyrimidin-2-yl)amino)phenyl)(morpholino)methanone | 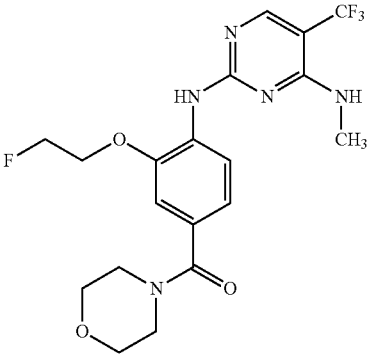 [SMILES: CNc1nc(Nc2ccc(C(=O)N3CCOCC3)cc2OCCF)ncc1C(F)(F)F] | |
| 40 (4-((5-chloro-4-methoxypyrimidin-2-yl)amino)-3-(2-fluoroethoxy)phenyl)(morpholino)methanone | 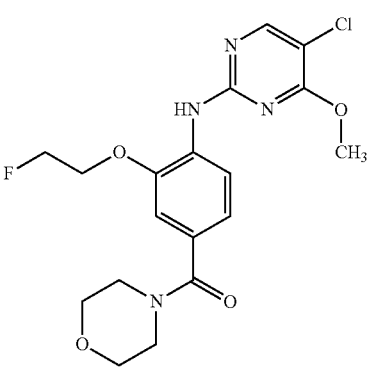 [SMILES: COc1nc(Nc2ccc(C(=O)N3CCOCC3)cc2OCCF)ncc1Cl] | 0.014 |
| 41 (5-chloro-2-(fluoromethoxy)-4-((4-(methylamino)-5-(trifluoromethyl)pyrimidin-2-yl)amino)phenyl)(morpholino)methanone | 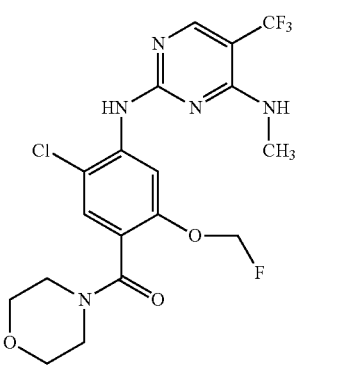 [SMILES: CNc1nc(Nc2cc(OCF)c(C(=O)N3CCOCC3)cc2Cl)ncc1C(F)(F)F] | |
| 42 N2-(1-(1-(2-fluoroethyl)piperidin-4-yl)-5-methyl-1H-pyrazol-4-yl)-N4-methyl-5-(trifluoromethyl)pyrimidine-2,4-diamine | 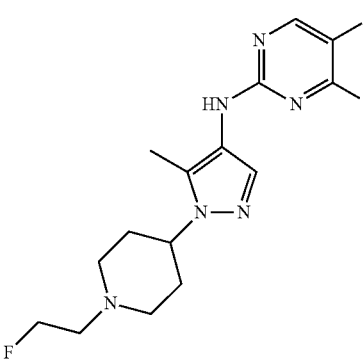 | |

TABLE 1-continued

| Name | Structure | Ki μM |
|---|---|---|
| 43 (3,3-difluoropyrrolidin-1-yl)(4-((4-(ethylamino)-5-(trifluoromethyl)pyrimidin-2-yl)amino)-5-(2-fluoroethoxy)-2-methoxyphenyl)methanone | | 0.047 |
| 44 (5-chloro-4-((4-(ethylamino)-5-(trifluoromethyl)pyrimidin-2-yl)amino)-2-(fluoromethoxy)phenyl)(morpholino)methanone | | 0.084 |
| 45 (4-((4-(ethylamino)-5-(trifluoromethyl)pyrimidin-2-yl)amino)-2-fluoro-5-methoxyphenyl)(morpholino)methanone | | |
| 46 (4-((4-(ethylamino)-5-(trifluoromethyl)pyrimidin-2-yl)amino)-2-fluoro-5-(fluoromethoxy)phenyl)(morpholino)methanone | | |

TABLE 1-continued

| Name | Structure | Ki µM |
|------|-----------|-------|
| 47 (2-fluoro-5-methoxy-4-((4-(methylamino)-5-(trifluoromethyl)pyrimidin-2-yl)amino)phenyl)(morpholino)methanone | | |
| 48 N2-(1-(2-fluoro-1,1,2,2-tetradeutero-ethyl)-5-methyl-1H-pyrazol-4-yl)-N4-methyl-5-(trifluoromethyl)pyrimidine-2,4-diamine | | 0.002 |
| 49 (4-(4-(cyclopropylamino)-5-(trifluoromethyl)pyrimidin-2-ylamino)-2-fluoro-5-(2-fluoromethoxy)phenyl)(morpholino)methanone | | |

Administration and Compositions

The invention includes compositions comprising at least one PET ligand compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the PET ligand compounds may be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of PET imaging will be able, without undue experimentation and in reliance upon personal knowledge and the disclosure of this Application, to ascertain an effective amount of the PET ligand compounds of the invention. PET ligand compounds of the invention may be administered as formulations including those suitable for oral or parenteral (including intramuscular, intraarterial, intrathecal, subcutaneous and intravenous) administration or in a form suitable for administration by inhalation or insufflation. PET ligand compounds of the invention may be administered together with one or more conventional adjuvants, carriers, or diluents. Formulations containing about one (1) milligram of active

EXAMPLES

Preparation 1:
2-chloro-5-fluoro-N-methylpyrimidin-4-amine

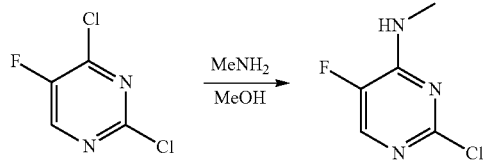

To a 250 mL round bottom flask equipped with a stir bar was added 9.0 g 5-fluoro-2,4-dichloro-pyrimidine, 40 mL methanol and 15 mL of 8M methylamine in ethanol. The reaction heated up (mild exo-therm) and was allowed to stir at room temperature for ~30 minutes. A check by TLC (1:1 EtOAc:heptane) and LCMS showed complete reaction. The reaction was concentrated down to give 9.77 g crude material which was purified on a silica column running a gradient of 1% to 10% MeOH in DCM over 35 minutes to give 6.77 g pure 2-chloro-5-fluoro-N-methylpyrimidin-4-amine.

The same method was used to make the compounds shown in Table 1 below, using the appropriate commercially available substituted 2,4-dichloro-pyrimidines and amines.

TABLE 2

| | | |
|---|---|---|
| 1 | 2-chloro-5-chloro-N-methylpyrimidin-4-amine | 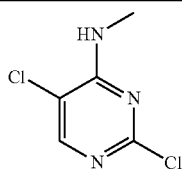 |
| 2 | 2-chloro-5-bromo-N-methylpyrimidin-4-amine | 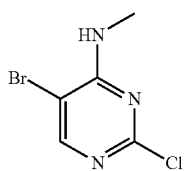 |
| 3 | 2-chloro-5-trifluoromethyl-N-methylpyrimidin-4-amine | 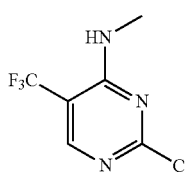 |
| 4 | 2-chloro-N-cyclopropyl-5-(trifluoromethyl)pyrimidin-4-amine | 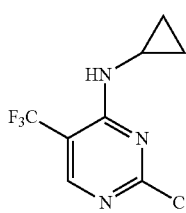 |

Example 1

(3-(2-fluoroethoxy)-4-(4-(methylamino)-5-(trifluoromethyl)pyrimidin-2-ylamino)phenyl)(morpholino)methanone

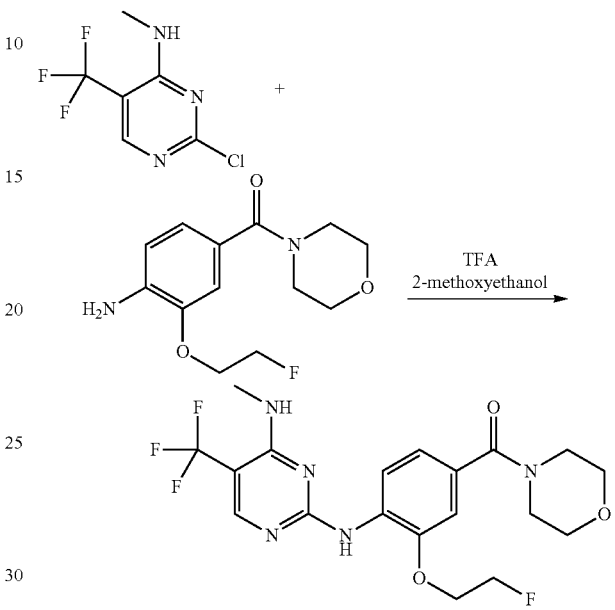

A mixture of 2-chloro-N-methyl-5-(trifluoromethyl)pyrimidin-4-amine (0.10 g, 0.47 mmol), (4-amino-3-(2-fluoroethoxy)phenyl)(morpholino)methanone (0.13 g, 0.47 mmol), trifluoroacetic acid (0.07 mL, 0.9 mmol) in 2-methoxyethanol (2.5 mL) was stirred at 95° C. for 6 hours. The reaction was the concentrated. The crude product was purified by reverse phase HPLC to give the title compound (61 mg, 29%).

Similarly prepared were:

[3-Methoxy-4-(4-methylamino-5-trifluoromethyl-pyrimidin-2-ylamino)-phenyl]-morpholin-4-yl-methanone; $^1$H NMR (400 MHz, DMSO) δ 8.31 (d, 1H), 8.19 (s, 1H), 8.07 (s, 1H), 7.21 (d, 1H), 7.07 (s, 1H), 7.02 (d, 1H), 3.90 (s, 3H), 3.56 (d, 9H), 2.92 (d, 3H); and

[4-(5-Chloro-4-methylamino-pyrimidin-2-ylamino)-3-hydroxy-phenyl]-morpholin-4-yl-methanone; $^1$H NMR (400 MHz, DMSO) δ 8.18 (d, J=8.3 Hz, 1H), 7.95 (s, 1H), 7.86 (s, 1H), 7.32 (d, J=4.6 Hz, 1H), 6.92-6.80 (m, 2H), 3.54 (d, J=36.7 Hz, 8H), 2.91 (d, J=4.6 Hz, 3H).

Example 2

Radiolabeling

The radiolabeling of LRRK2 ligand consisted of two steps as follows (Scheme 1): Step 1. [$^{18}$F]fluoride was incorporated to $^{18}$F-alkyl-R2 by nucleophilic substitution using R1-alkyl-R2 as a starting material (R1,2=p-toluenesulfonyl, methylsulfonyl, trifluormethylsulfonyl, halide; alkyl=methyl, ethyl, propyl. Step 2. The precursor (P) phenol is alkylated with $^{18}$F-alkyl-R2 (for example, $^{18}$F-alkyltosylate such as $^{18}$F-ethyl tosylate, $^{18}$F-methyl tosylate) to afford desired product. The crude product is purified by HPLC and formulated for injection. Preparation of such $^{18}$F-alkylating agents is well known and is described by Muschio et al., J. Labeled Compounds and Radiopharmaceuticals, 2005:48:735-747; Lu et al., J. Labeled Compounds and Radiopharmaceuticals, 2004: 47:289-297; and others.

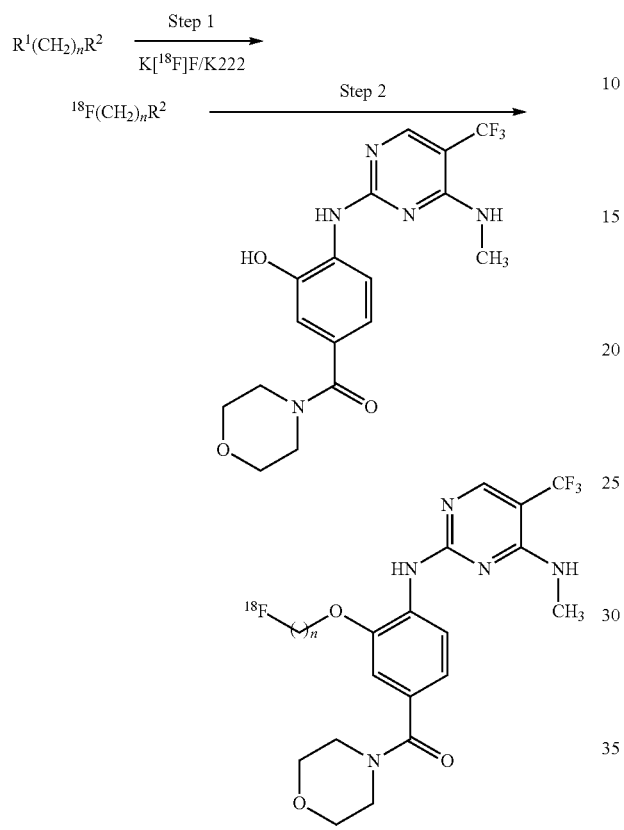

Preparation of [$^{18}$F]fluoroethyl-G1023 ((3-(2-$^{18}$Fluoroethoxy)-4-(4-(methylamino)-5-(trifluoromethyl)pyrimidin-2-ylamino)phenyl)(morpholino)methanone Step 1: 2-$^{18}$F-Ethylene glycol $^{18}$F-fluoride was loaded onto QMA cartridge and eluted with 1 mL of solution containing K222 ("Kryptofix 222" 4,7,13,16,21,24-hexaoxa-1,10-diazabicyclo[8.8.8]-hexacosane, 5 mg) and $K_2CO_3$ (0.5 mg) in water/ACN 1:1. The cartridge was washed with ACN (1 mL) and the K$^{18}$F/K222 complex was eluted using ACN (4×0.5 mL). Ethylene glycol ditosylate (1.5 mg) was added in 0.3 mL ACN and the mixture was heated to 110-120° C. for 15 min. The reaction mixture was cooled bellow 60° C. before opening the vessel. ACN was evaporated MeCN to ~100 uL using microwave heating to give $^{18}$F-ethylene tosylate (MW: 20 W, 60° C., 300 ccm). Precursor for G1023 43-hydroxy-4-((4-(methylamino)-5-(trifluoromethyl)pyrimidin-2-yl)amino)phenyl)(morpholino)methanone, 2 mg) was added in 300 uL DMF containing 10 mg of $K_2CO_3$ and the reaction mixture was heated using microwave heater MW: 40 W, 100° C., 400-600 s. The reaction mixture was diluted with $H_2O$ (2 mL) and delivered to HPLC loop. The collected fractions containing the product were diluted with $H_2O$ (10 mL), loaded on HLB plus cartridge, rinsed with $H_2O$ (6 mL), eluted with EtOH (3 mL), and evaporated to near dryness using microwave heater (MW: 40 W, 90° C., 800 ccm). The product was dissolved at concentration 50 mCi/mL with 10 mg/mL gentisic acid, pH5.5 and formulate for injection with 50% PEG-400, 50% $H_2O$.

Example 3

Preparation of (4-(4-(cyclopropylamino)-5-(trifluoromethyl)pyrimidin-2-ylamino)-2-fluoro-5-(2-$^{18}$F-methoxy)phenyl)(morpholino)methanone The procedure of Example 3 is shown in Scheme II.

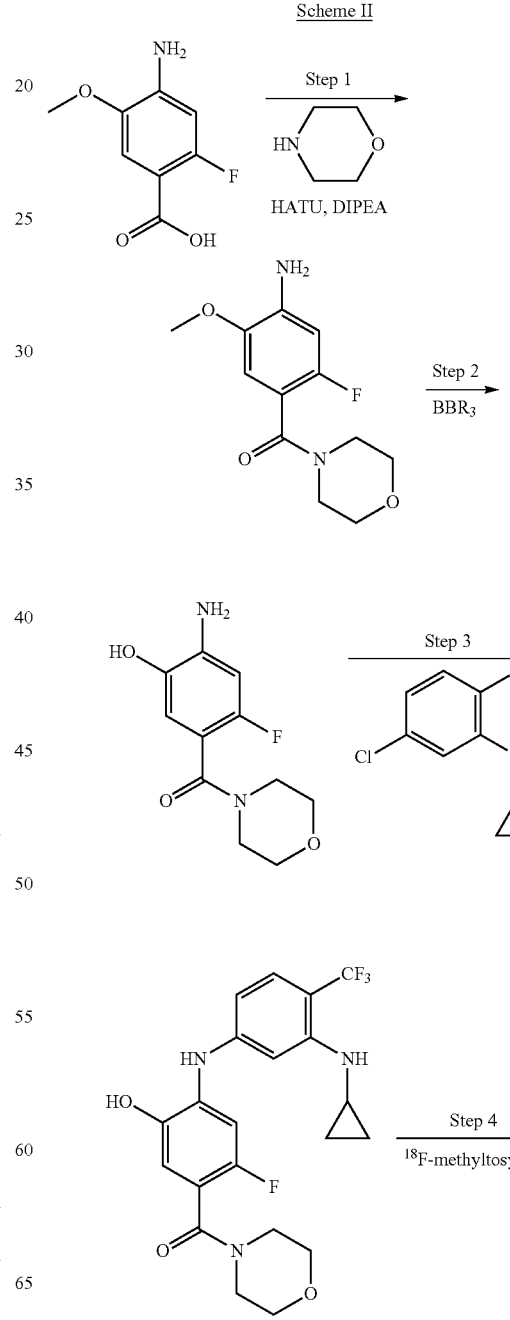

-continued

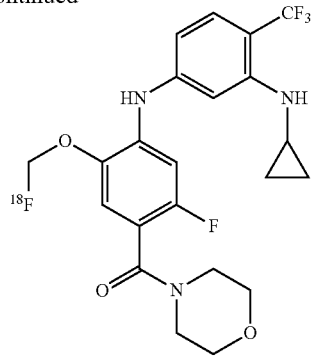

Step 1: (4-Amino-2-fluoro-5-methoxyphenyl)(morpholino)methanone

A mixture of 4-amino-2-fluoro-5-methoxybenzoic acid (600 mg, 3.24 mmol), morpholine (564 mg, 6.48 mmol), HATU ((O-(7-azabenzotriazol-1-yl)-N,N,N',N'-tetramethyluronium hexafluorophosphate, 1.85 g, 4.86 mmol), DIPEA (diisopropyl ethylamine, 836 mg, 6.48 mmol), and $CH_2Cl_2$ (20 mL) was stirred at room temperature for 6 h. The solvent was removed under reduced pressure and the residue was purified by silica-gel column chromatography to afford the title compound (560 mg, 68%).

Step 2: (4-Amino-2-fluoro-5-hydroxyphenyl)(morpholino)methanone

A mixture of (4-amino-2-fluoro-5-methoxyphenyl)(morpholino)methanone (260 mg, 1.02 mmol), $BBr_3$ (1.28 g, 5.10 mmol), and $CH_2Cl_2$ (15 mL) was stirred at 0° C. for 2 h. The reaction was quenched by water at 0° C. The resulting mixture was extracted with EtOAc. The combined organic layer was washed with brine (20 mL), dried over sodium sulfate, and concentrated under reduced pressure. Silica-gel column chromatography afforded the title product as yellow solid (200 mg, 81%).

Step 3: (4-(4-(Cyclopropylamino)-5-(trifluoromethyl)pyrimidin-2-ylamino)-2-fluoro-5-hydroxyphenyl)(morpholino)methanone A mixture of (4-amino-2-fluoro-5-hydroxyphenyl)(morpholino)methanone (200 mg, 0.83 mmol), 2-chloro-N-cyclopropyl-5-(trifluoromethyl)pyrimidin-4-amine (198 mg, 0.83 mmol), concentrated HCl (0.1 mL), and n-BuOH (10 mL) was stirred at 100° C. for 10 h. The mixture was concentrated under reduced pressure and the residue was purified by rp-HPLC to afford the title compound as white solid (125 mg, 34%); $^1$H NMR (500 MHz, DMSO) δ 8.55-8.49 (m, 1H), 8.26 (s, 1H), 8.18-8.08 (m, 1H), 7.45 (br s, 1H), 6.77 (d, J=7.0 Hz, 1H), 3.62-3.53 (m, 4H), 3.48-3.46 (m, 2H), 3.30-3.11 (m, 2H), 2.84-2.82 (m, 1H), 0.84-0.78 (m, 2H), 0.75-0.68 (m, 2H); LCMS: m/z=442.3 [M+H]$^+$.

Step 4: (4-(4-(Cyclopropylamino)-5-(trifluoromethyl)pyrimidin-2-ylamino)-2-fluoro-5-(2-$^{18}$F-methoxy)phenyl)(morpholino)methanone $^{18}$F-methyltosylate was dissolved in 0.4 ml of DMF and added into a reaction vial containing (4-(4-(cyclopropylamino)-5-(trifluoromethyl)pyrimidin-2-ylamino)-2-fluoro-5-hydroxyphenyl)(morpholino)methanone (1 mg) and $K_2CO_3$ (30 mg). The reaction mixture was heated to 120° C. for 10 min using microwave heater set to 40 W. The reaction mixture was diluted with 2.0 mL of 1% acetic acid and delivered to semi-preparative HPLC system (Luna 5µ C18 100 A, 250 mm×10 mm column, flow rate 3 ml/min) and eluted with following acetonitrile (ACN)/formic acid. The collected fractions were diluted 10 fold with water and passed through a Strata-X (60 mg) SPE which was then rinsed with another 8 ml of water and dried by passing 1000 ccm of nitrogen through the SPE for 3 minutes. The product was eluted from the SPE using ethanol (3 ml) which was subsequently evaporated. The product was formulated in 1:1 PEG400/sterile water for injection, for iv injection.

Example 3

MicroPET Imaging

Mice were anesthetized with approx. 3% sevoflurane to effect and injected i.v. via the tail vein with 0.2-0.3 mCi of $^{18}$F-radiolabeled tracer in isotonic solution. The PET imaging was performed on an Inveon PET/CT scanner. Animals were placed head-first, prone position on the scanner bed and static or dynamic scans were acquired. Dynamic data were acquired for 0-120 min post tracer injection. Body temperature was measured by a rectal probe and maintained with warm air. Full-body iterative image reconstructions were obtained using maximum a posteriori algorithm (MAP, hyperparameter beta=0.05) and corrected for signal attenuation using the tissue density obtained from CT. Projections were created with IRW software (Siemens Preclinical Solutions) and used to obtain quantitative activity levels in each organ of interest using region-of-interest analysis.

Radiolabeled Compound Uptake and Imaging Results

Images of obtained with [$^{18}$F]fluoroethyl-G1023 ((3-hydroxy-4-((4-(methylamino)-5-(trifluoromethyl)pyrimidin-2-yl)amino)phenyl)(morpholino)methanone using 30 min dynamic scan and kinetic analysis, as well as brain uptake (% injected dose per gram of tissue vs time) for several dosages, and the parametric plot with Vt (Logan) 0-3 ml/g, are shown in FIG. 1.

FIG. 2A illustrates brain uptake (% injected dose per gram of tissue vs time) in mice for radiolabeled compounds ((3-$^{11}$Cmethoxy-4-((4-(methylamino)-5-(trifluoromethyl)pyrimidin-2-yl)amino)phenyl)(morpholino) methanone), (4-((4-(ethylamino)-5-(trifluoromethyl)pyrimidin-2-yl)amino)-2-fluoro-5-(2-$^{18}$F-ethoxy)phenyl)(morpholino)methanone and (4-((4-(ethylamino)-5-(trifluoromethyl)pyrimidin-2-yl) amino)-2-fluoro-5-($^{18}$F-methoxy)phenyl)(morpholino) methanone.

FIG. 2B illustrates brain uptake (% injected dose per gram of tissue vs time) in mice for radiolabeled compounds (4-((4-(ethylamino)-5-(trifluoromethyl)pyrimidin-2-yl)amino)-2-fluoro-5-$^{11}$Cmethoxyphenyl)(morpholino)methanone, (4-((4-(ethylamino)-5-(trifluoromethyl)pyrimidin-2-yl)amino)-2-fluoro-5-(2-$^{18}$F-ethoxy)phenyl)(morpholino)methanone and (4-((4-(ethylamino)-5-(trifluoromethyl)pyrimidin-2-yl) amino)-2-fluoro-5-(2-$^{18}$F-methoxy)phenyl)(morpholino) methanone.

FIG. 2C illustrates brain uptake (% injected dose per gram of tissue vs time) in mice for radiolabeled compounds (4-(4-(cyclopropylamino)-5-(trifluoromethyl)pyrimidin-2-ylamino)-2-fluoro-5-(2-$^{18}$F-ethoxy)phenyl)(morpholino) methanone and (4-(4-(cyclopropylamino)-5-(trifluoromethyl)pyrimidin-2-ylamino)-2-fluoro-5-(2-$^{18}$F-methoxy) phenyl)(morpholino)methanone.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for positron emission tomography (PET) imaging of LRRK2 in tissue of a subject, the method comprising:
   administering to the subject a compound of formula I, or a pharmaceutically acceptable salt thereof,

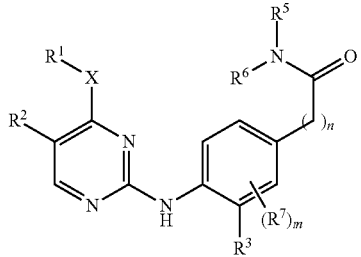

I wherein:
   m is from 0 to 3;
   X is: —NR$^a$—; —O—; or —S(O)$_r$— wherein r is from 0 to 2 and R$^a$ is hydrogen or C$_{1-6}$alkyl;
   R$^1$ is: C$_{1-6}$alkyl; halo-C$_{1-6}$alkyl; C$_{2-6}$alkenyl; C$_{2-6}$alkynyl; halo-C$_{1-6}$alkyl; C$_{1-6}$alkoxy-C$_{1-6}$alkyl; hydroxy-C$_{1-6}$alkyl; amino-C$_{1-6}$alkyl; C$_{1-6}$alkylsulfonyl-C$_{1-6}$alkyl; C$_{3-6}$cycloalkyl optionally substituted with C$_{1-6}$alkyl or halo; C$_{3-6}$cycloalkyl-C$_{1-6}$alkyl wherein the C$_{3-6}$cycloalkyl portion is optionally substituted with C$_{1-6}$alkyl; tetrahydropyranyl; tetrahydrofuranyl; tetrahydrofuranyl-C$_{1-6}$alkyl; oxetanyl; or oxetan-C$_{1-6}$alkyl;
   or R$^1$ and R$^a$ together with the atoms to which they are attached may form a three to six membered ring that may optionally include an additional heteroatom selected from O, N and S and which is substituted with oxo, halo or C$_{1-6}$alkyl;
   R$^2$ is: halo; C$_{1-6}$alkoxy; cyano; C$_{2-6}$alkynyl; C$_{2-6}$alkenyl; halo-C$_{1-6}$alkyl; halo-C$_{1-6}$alkoxy; C$_{3-6}$cycloalkyl wherein the C$_{3-6}$cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; acetyl; oxetanyl; or oxetan-C$_{1-6}$alkyl;
   R$^3$ is: —OR$^4$; halo; cyano; C$_{1-6}$alkyl; halo-C$_{1-6}$alkyl; C$_{3-6}$cycloalkyl optionally substituted with C$_{1-6}$alkyl; C$_{3-6cycloalkyl-C1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; oxetanyl; or oxetan-C$_{1-6}$alkyl;
   R$^4$ is: hydrogen; C$_{1-6}$alkyl; halo-C$_{1-6}$alkyl; C$_{1-6}$alkoxy-C$_{1-6}$alkyl; C$_{3-6}$cycloalkyl optionally substituted with C$_{1-6}$alkyl or halo; C$_{3-6}$cycloalkyl-C$_{1-6}$alkyl wherein the C$_{3-6}$cycloalkyl portion is optionally substituted with C$_{1-6}$alkyl or halo; C$_{3-6}$cycloalkyl-C$_{1-6}$alkyl wherein the C$_{3-6}$cycloalkyl portion is optionally substituted with C$_{1-6}$alkyl or halo; tetrahydrofuranyl; tetrahydrofuranyl-C$_{1-6}$alkyl; oxetanyl; or oxetan-C$_{1-6}$alkyl;
   R$^5$ is: hydrogen; or C$_{1-6}$alkyl;
   n is 0 or 1;
   R$^6$ is: hydrogen; C$_{1-6}$alkyl; C$_{1-6}$alkoxy-C$_{1-6}$alkyl; hydroxy-C$_{1-6}$alkyl; amino-C$_{1-6}$alkyl; C$_{3-6}$cycloalkyl; C$_{3-6}$cycloalkyl-C$_{1-6}$alkyl; heterocyclyl; or heterocyclyl-C$_{1-6}$alkyl; wherein the C$_{3-6}$cycloalkyl, C$_{3-6}$cycloalkyl-C$_{1-6}$alkyl, heterocyclyl and heterocyclyl-C$_{1-6}$alkyl each may be optionally substituted with one, two, three or four groups groups independently selected from: C$_{1-6}$alkyl; halo-C$_{1-6}$alkyl; C$_{1-6}$alkoxy; halo-C$_{1-6}$alkoxy; hydroxy; hydroxy-C$_{1-6}$alkyl; halo; Nitrile; C$_{1-6}$alkyl-carbonyl; C$_{1-6}$alkyl-sulfonyl; C$_{3-6}$cycloalkyl; C$_{3-6}$cycloalkyl-C$_{1-6}$alkyl; C$_{3-6}$cycloalkyl-carbonyl; amino; or heterocyclyl; or two of the groups together with the atoms to which they are attached may form a five or six-membered ring;
   or R$^5$ and R$^6$ together with the nitrogen atom to which they are attached form a three- to seven-membered ring that optionally includes an additional heteroatom selected from O N and S(O)$_n$, and which is optionally substituted with one, two, three or four groups independently selected from: C$_{1-6}$alkyl; halo-C$_{1-6}$alkyl; C$_{1-6}$alkoxy; halo-C$_{1-6}$alkoxy; hydroxy; C$_{1-6}$alkoxy-C$_{1-6}$alkyl; hydroxy-C$_{1-6}$alkyl; halo, nitrile; C$_{1-6}$alkyl-carbonyl; C$_{1-6}$alkyl-sulfonyl; C$_{3-6}$cycloalky; C$_{3-6}$cycloalkyl-C$_{1-6}$alkyl; C$_{3-6}$cycloalkyl-carbonyl; amino; or heterocyclyl; or two of the groups together with the atoms to which they are attached may form a five or six-membered ring; and
   R$^7$ is: halo; C$_{1-6}$alkyl; C$_{1-6}$alkoxy; halo-C$_{1-6}$alkyl; or halo-C$_{1-6}$alkoxy;
wherein the compound includes at least one $^{11}$C or $^{18}$F label thereon;
   allowing the compound to penetrate into the tissue of the subject; and
   collecting a PET image of the CNS or brain tissue of the subject.

2. The method of claim 1, wherein the compound is labeled with $^{18}$F.

3. The method of claim 1, wherein the compound is labeled with $^{11}$C.

4. The method of claim 1, wherein the compound is labeled with $^{18}$F on a C$_{1-6}$ alkoxy moiety.

5. The method of claim 1, wherein the compound is labeled with $^{11}$C on a C$_{1-6}$alkoxy moiety.

6. The method of claim 1, wherein n is 0.

7. The method of claim 6, wherein m is 0 or 1.

8. The method of claim 7, wherein R$^3$ is C$_{1-6}$alkoxy with a $^{18}$F atom thereon.

9. The method of claim 8, wherein R$^2$ is trifluoromethyl.

10. The method of claim 1, wherein R$^7$ is fluoro.

11. The method of claim 10, wherein R$^1$ is cyclopropyl.

12. The method of claim 1, wherein the compound of formula I is selected from:
   (4-(4-(cyclopropylamino)-5-(trifluoromethyl)pyrimidin-2-ylamino)-2-fluoro-5-(2-fluoroethoxy)phenyl)(morpholino)methanone;
   (5-(fluoromethoxy)-2-methyl-4-(4-(methylamino)-5-(trifluoromethyl)pyrimidin-2-ylamino)phenyl)(morpholino)methanone;
   (3,3-difluoropyrrolidin-1-yl)(4-(4-(ethylamino)-5-(trifluoromethyl)pyrimidin-2-ylamino)-5-(2-fluoroethoxy)-2-methoxyphenyl)methanone;
   (5-chloro-4-(4-(ethylamino)-5-(trifluoromethyl)pyrimidin-2-ylamino)-2-(fluoromethoxy)phenyl)(morpholino)methanone;

(5-chloro-4-(4-(ethylamino)-5-(trifluoromethyl)pyrimidin-2-ylamino)-2-(fluoromethoxy)phenyl)(pyrrolidin-1-yl)methanone;

(3,3-difluoropyrrolidin-1-yl)(4-(4-(ethylamino)-5-(trifluoromethyl)pyrimidin-2-ylamino)-5-(fluoromethoxy)-2-methoxyphenyl)methanone;

(5-(fluoromethoxy)-2-methyl-4-(4-(methylamino)-5-(trifluoromethyl)pyrimidin-2-ylamino)phenyl)(pyrrolidin-1-yl)methanone;

(3,3-difluoropyrrolidin-1-yl)(4-(4-(ethylamino)-5-(trifluoromethyl)pyrimidin-2-ylamino)-2,5-dimethoxyphenyl)methanone;

(5-(fluoromethoxy)-2-methoxy-4-(4-(methylamino)-5-(trifluoromethyl)pyrimidin-2-ylamino)phenyl)(piperidin-1-yl)methanone;

(4-(4-(ethylamino)-5-(trifluoromethyl)pyrimidin-2-ylamino)-2-fluoro-5-(2-fluoroethoxy)phenyl)(morpholino)methanone;

(5-(2-fluoroethoxy)-2-methyl-4-(4-(methylamino)-5-(trifluoromethyl)pyrimidin-2-ylamino)phenyl)(morpholino)methanone;

(5-(fluoromethoxy)-2-methoxy-4-(4-(methylamino)-5-(trifluoromethyl)pyrimidin-2-ylamino)phenyl)(pyrrolidin-1-yl)methanone;

(4-(4-(ethylamino)-5-(trifluoromethyl)pyrimidin-2-ylamino)-5-fluoro-2-(fluoromethoxy)phenyl)(pyrrolidin-1-yl)methanone;

(2-fluoro-5-(2-fluoroethoxy)-4-(4-(methylamino)-5-(trifluoromethyl)pyrimidin-2-ylamino)phenyl)(morpholino)methanone;

5-(fluoromethoxy)-2-methoxy-N,N-dimethyl-4-(4-(methylamino)-5-(trifluoromethyl)pyrimidin-2-ylamino)benzamide;

(5-(2-fluoroethoxy)-2-methoxy-4-(4-(methylamino)-5-(trifluoromethyl)pyrimidin-2-ylamino)phenyl)(pyrrolidin-1-yl)methanone;

(2-fluoro-5-(fluoromethoxy)-4-(4-(methylamino)-5-(trifluoromethyl)pyrimidin-2-ylamino)phenyl)(pyrrolidin-1-yl)methanone;

(4-(5-chloro-4-methoxypyrimidin-2-ylamino)-5-(fluoromethoxy)-2-methylphenyl)(pyrrolidin-1-yl)methanone;

(4-(5-chloro-4-methoxypyrimidin-2-ylamino)-3-(2-fluoroethoxy)phenyl)(morpholino)methanone;

(3-(2-fluoroethoxy)-4-(4-(methylamino)-5-(trifluoromethyl)pyrimidin-2-ylamino)phenyl)(morpholino)methanone;

(3-(2-fluoroethoxy)-4-(4-(methylamino)-5-(trifluoromethyl)pyrimidin-2-ylamino)phenyl)(morpholino)methanone; and (3-methoxy-4-(4-(methylamino)-5-(trifluoromethyl)pyrimidin-2-ylamino)phenyl)(morpholino)methanone.

* * * * *